(12) United States Patent
Parham et al.

(10) Patent No.: US 10,600,970 B2
(45) Date of Patent: Mar. 24, 2020

(54) CARBAZOLES WITH TWO DIBENZOFURAN OR DIBENZOTHIOPHENE SUBSTITUENTS

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Tobias Grossmann, Darmstadt (DE); Jonas Valentin Kroeber, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 95 days.

(21) Appl. No.: 15/539,177

(22) PCT Filed: Nov. 24, 2015

(86) PCT No.: PCT/EP2015/002360
§ 371 (c)(1),
(2) Date: Jun. 23, 2017

(87) PCT Pub. No.: WO2016/102040
PCT Pub. Date: Jun. 30, 2016

(65) Prior Publication Data
US 2019/0044071 A1 Feb. 7, 2019

(30) Foreign Application Priority Data

Dec. 23, 2014 (EP) .................... 14004391

(51) Int. Cl.
| | | |
|---|---|---|
| H01L 51/00 | (2006.01) | |
| C07D 405/14 | (2006.01) | |
| C07D 409/14 | (2006.01) | |
| C07D 405/10 | (2006.01) | |
| H01L 51/50 | (2006.01) | |

(52) U.S. Cl.
CPC ........ *H01L 51/0072* (2013.01); *C07D 405/10* (2013.01); *C07D 405/14* (2013.01); *C07D 409/14* (2013.01); *H01L 51/0067* (2013.01); *H01L 51/0073* (2013.01); *H01L 51/0074* (2013.01); *H01L 51/5004* (2013.01); *H01L 51/5072* (2013.01); *H01L 51/5092* (2013.01); *H01L 51/5096* (2013.01); *H01L 2251/552* (2013.01)

(58) Field of Classification Search
CPC ............. H01L 51/0072; H01L 51/0074; H01L 51/0073; H01L 51/0067; H01L 51/5004; H01L 51/5096; H01L 51/5092; H01L 51/5072; H01L 2251/552; H01L 51/0085; H01L 51/5016; H01L 2251/5384; H01L 51/05; H01L 51/42; C07D 405/10; C07D 405/14; C07D 409/14; Y02E 10/549; C09K 11/06; C09K 2211/1092; C09K 2211/1088; C09K 2211/1029
USPC ....................................................... 252/500
See application file for complete search history.

(56) References Cited

U.S. PATENT DOCUMENTS

| | | | |
|---|---|---|---|
| 8,242,488 B2 | 8/2012 | Katakura et al. | |
| 8,367,224 B2 | 2/2013 | Katakura et al. | |
| 8,580,399 B2 | 11/2013 | Dyatkin et al. | |
| 9,923,151 B2 | 3/2018 | Numata | |
| 10,333,081 B2 | 6/2019 | Lee et al. | |
| 2010/0207105 A1* | 8/2010 | Katakura ............. | C07D 209/86 257/40 |
| 2011/0006670 A1* | 1/2011 | Katakura ............. | C07D 403/10 313/504 |
| 2013/0270540 A1* | 10/2013 | Numata ................. | C09K 11/06 257/40 |

FOREIGN PATENT DOCUMENTS

| | | |
|---|---|---|
| JP | 20118991 A | 1/2011 |
| JP | 201184531 A | 4/2011 |
| JP | 201494935 A | 5/2014 |
| JP | 2014511861 A | 5/2014 |
| KR | 20140099082 A | 8/2014 |
| KR | 20140132244 A | 11/2014 |
| WO | WO-2008146838 A1 | 12/2008 |
| WO | WO-2009060757 A1 | 5/2009 |
| WO | WO-2011004639 A1 | 1/2011 |
| WO | WO-2012090967 A1 | 7/2012 |
| WO | WO-2014030831 A1 | 2/2014 |

OTHER PUBLICATIONS

International Search Report for PCT/EP2015/002360 dated Jan. 28, 2016.
Written Opinion of the International Searching Authority for PCT/EP2015/002360 dated Jan. 28, 2016.

* cited by examiner

*Primary Examiner* — Douglas J McGinty
(74) *Attorney, Agent, or Firm* — Drinker Biddle & Reath LLP

(57) ABSTRACT

The present invention relates to carbazoles having two dibenzofuran or dibenzothiophene substituents, and to electronic devices, especially organic electroluminescent devices, comprising these compounds.

21 Claims, No Drawings

CARBAZOLES WITH TWO DIBENZOFURAN OR DIBENZOTHIOPHENE SUBSTITUENTS

CROSS-REFERENCE TO RELATED APPLICATIONS

This application is a national stage application (under 35 U.S.C. § 371) of PCT/EP2015/002360, filed Nov. 24, 2015, which claims benefit of European Application No. 14004391.0, filed Dec. 23, 2014, both of which are incorporated herein by reference in their entirety.

The present invention relates to carbazoles having two dibenzofuran or dibenzothiophene substituents that are suitable for use in electronic devices. The present invention further relates to processes for preparation thereof and to electronic devices.

BACKGROUND OF THE INVENTION

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general substrate structure which can be adjusted for the particular application:
(1) substrate,
(2) electrode, frequently metallic or inorganic, but also composed of organic or polymeric conductive materials,
(3) charge injection layer(s) or interlayer(s), for example to compensate for unevenness in the electrode ("planarization layer"), frequently composed of a conductive doped polymer,
(4) organic semiconductor,
(5) possibly further charge transport, charge injection or charge blocker layers,
(6) counterelectrode, materials as specified in (2),
(7) encapsulation.

The above arrangement is the general structure of an organic electronic device, it being possible to combine various layers, such that the result in the simplest case is an arrangement composed of two electrodes with an organic layer in between. In this case, the organic layer fulfils all functions including the emission of light in the case of OLEDs. A system of this kind is described, for example, in WO 90/13148 A1, based on poly(p-phenylenes).

Electronic devices containing carbazoles having dibenzofuran or dibenzothiophene substituents are known inter alia from publications US 2012/0289708, WO 2012/086170, US 2012/071668, US 2012/091887, WO 2012/033108, CN 102850334, WO 2013/032278, US 2012/0256169, WO 2012/036482; WO 2013/5923, WO 2013/084885, WO 2013/102992, WO 2013/084881, WO 2012/067425, US 2011/260138, WO 2011/125680, WO 2011/122132, WO 2013/109045, WO 2013/151297, WO 2013/41176, WO 2012/108389, KR 2013/0025087 and KR 2013/0112342.

Known electronic devices have a useful profile of properties. However, there is a constant need to improve the properties of these devices.

These properties especially include the energy efficiency with which an electronic device solves the problem defined. In the case of organic light-emitting diodes, which may be based either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance. A further particular problem is the lifetime of the electronic devices.

BRIEF SUMMARY OF THE INVENTION

It is therefore an object of the present invention to provide novel compounds which lead to electronic devices having improved properties. It is a particular object to provide hole transport materials, hole injection materials, hole blocker materials, electron injection materials, electron blocker materials and/or electron transport materials which exhibit improved properties in relation to efficiency, operating voltage and/or lifetime. Moreover, the compounds should be processible in a very simple manner, and especially exhibit good solubility and film formation.

A further object can be considered that of providing electronic devices having excellent performance very inexpensively and in constant quality, Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of Claim 1. Appropriate modifications to the compounds of the invention are protected in the dependent claims that refer back to Claim 1.

DETAILED DESCRIPTION OF THE INVENTION

The invention thus provides a compound comprising at least one structure of the formula (I)

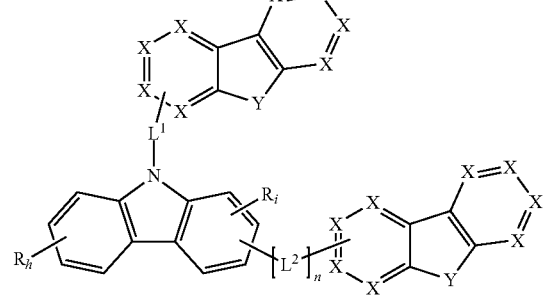

Formula (I)

where the symbols used are as follows:
X is N or $CR^1$, preferably $CR^1$, with the proviso that not more than one of the X groups in one cycle is N, or C is the attachment site of the $L^1$, $L^2$ radicals or the carbazole group;

Y is the same or different at each instance and is O or S;

$L^1$, $L^2$ is an aromatic ring system having 6 to 40 carbon atoms, but one which does not have any fused aromatic rings (for example naphthalenes, anthracenes, benzanthracenes or pyrenes), where the aromatic ring system may be substituted by one or more $R^4$ radicals; preferably, the $L^1$, $L^2$ group is an aryl group which has 6 to 40 carbon atoms and does not have any fused aromatic rings, where the aryl group may be substituted by one or more $R^4$ radicals;

R is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, NO$_2$, Si($R^2$)$_3$, B(O$R^2$)$_2$, OSO$_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by C≡C, Si($R^2$)$_2$, Ge($R^2$)$_2$, Sn($R^2$)$_2$, C=O, C=S, C=Se, P(=O)($R^2$), SO, SO$_2$, O, S or CON$R^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems, excluding any ring closure of two or more R radicals, even via substituents;

$R^1$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, NO$_2$, Si($R^2$)$_3$, B(O$R^2$)$_2$, OSO$_2R^2$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^2$ radicals, where one or more nonadjacent CH$_2$ groups may be replaced by $R^2$C=C$R^2$, C≡C, Si($R^2$)$_2$, Ge($R^2$)$_2$, Sn($R^2$)$_2$, C=O, C=S, C=Se, P(=O)($R^2$), SO, SO$_2$, O, S or CON$R^2$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^2$ radicals, or an aryloxy or heteroaryloxy group which has 5 to 40 aromatic ring atoms and may be substituted by one or more $R^2$ radicals, or a combination of these systems; at the same time, two or more adjacent $R^1$ substituents may also form a mono- or polycyclic aliphatic or aromatic ring system with one another;

$R^2$ is the same or different at each instance and is H, D, F, Cl, Br, I, CHO, C(=O)$Ar^1$, P(=O)($Ar^1$)$_2$, S(=O)$Ar^1$, S(=O)$_2Ar^1$, CN, NO$_2$, Si($R^3$)$_3$, B(O$R^3$)$_2$, OSO$_2R^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^3$ radicals, where one or more nonadjacent CH$_2$ groups may be replaced by C≡C, Si($R^3$)$_2$, Ge($R^3$)$_2$, Sn($R^3$)$_2$, C=O, C=S, C=Se, P(=O)($R^3$), SO, SO$_2$, O, S or CON$R^3$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more $R^3$ radicals, or an aryloxy or heteroaryloxy group which has 5 to 40 aromatic ring atoms and may be substituted by one or more $R^3$ radicals, or a combination of these systems; at the same time, two or more adjacent $R^2$ substituents may also form a mono- or polycyclic aliphatic or aromatic ring system with one another;

$Ar^1$ is the same or different at each instance and is an aromatic or heteroaromatic ring system which has 5 to 30 aromatic ring atoms and may be substituted by one or more $R^2$ radicals; at the same time, it is also possible for two $Ar^1$ radicals bonded to the same phosphorus atom to be joined to one another by a single bond or a bridge selected from B($R^3$), C($R^3$)$_2$, Si($R^3$)$_2$, C=O, C=N$R^3$, C=C($R^3$)$_2$, O, S, S=O, SO$_2$, N($R^3$), P($R^3$) and P(=O)$R^3$;

$R^3$ is the same or different at each instance and is H, D, F or an aliphatic, aromatic and/or heteroaromatic hydrocarbyl radical having 1 to 20 carbon atoms, in which hydrogen atoms may also be replaced by F; at the same time, two or more adjacent $R^3$ substituents together may also form a mono- or polycyclic, aliphatic or aromatic ring system;

$R^4$ is the same or different at each instance and is H, D, F, Cl, Br, I, CHO, C(=O)$Ar^2$, P(=O)($Ar^2$)$_2$, S(=O)$Ar^2$, S(=O)$_2Ar^2$, CN, NO$_2$, Si($R^5$)$_3$, B(O$R^5$)$_2$, OSO$_2R^5$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^5$ radicals, where one or more nonadjacent CH$_2$ groups may be replaced by C≡C, Si($R^5$)$_2$, Ge($R^5$)$_2$, Sn($R^5$)$_2$, C=O, C=S, C=Se, P(=O)($R^5$), SO, SO$_2$, O, S or CON$R^5$ and where one or more hydrogen atoms may be replaced by D, F, Cl, Br, I, CN or NO$_2$, or an aromatic ring system which has 5 to 40 carbon atoms, which does not have any fused aromatic rings and which may be substituted in each case by one or more $R^5$ radicals, or an aryloxy group which has 5 to 40 aromatic ring atoms and may be substituted by one or more $R^5$ radicals, or a combination of these systems; at the same time, two or more adjacent $R^4$ substituents may also form a mono- or polycyclic aliphatic ring system with one another, but one which does not have any fused aromatic rings;

$Ar^2$ is the same or different at each instance and is an aromatic ring system which has 5 to 30 carbon atoms, which does not have any fused aromatic rings and which may be substituted by one or more $R^5$ radicals;

$R^5$ is the same or different at each instance and is H, D, F or an aliphatic and/or aromatic hydrocarbyl radical having 1 to 20 carbon atoms, in which hydrogen atoms may also be replaced by F; at the same time, two or more adjacent $R^5$ substituents together may also form a mono- or polycyclic aliphatic ring system, but one which does not have any fused aromatic rings;

h at each instance is 0, 1, 2, 3 or 4;

i at each instance is independently 0, 1, 2 or 3;

n at each instance is independently 0 or 1;

with the proviso that the $L^1$ and/or $L^2$ group forms through-conjugation with the carbazole ring of the formula (I) and the dibenzofuran structure (Y=O) and/or the dibenzothiophene structure (Y=S), the R radicals bonded to the carbazole ring of the formula (I) do not form a fused ring system with the phenyl group of the carbazole ring to which this R group is bonded and the R radicals bonded to the carbazole ring of the formula (I) are not a carbazole group or azacarbazole group in which the nitrogen atom of this carbazole group or azacarbazole group is bonded to the carbazole ring of the formula (I).

The $L^1$ and/or $L^2$ group forms through-conjugation with the carbazole ring of the formula (I) and the dibenzofuran structure (Y=O) and/or the dibenzothiophene structure (Y=S). Through-conjugation of the aromatic or heteroaromatic systems is formed as soon as direct bonds are formed between adjacent aromatic or heteroaromatic rings. A further bond between the aforementioned conjugated groups, for example via a sulphur, nitrogen or oxygen atom or a carbonyl group, is not detrimental to conjugation. In the case of a fluorene system, the two aromatic rings are bonded directly, where the sp$^3$-hybridized carbon atom in position 9 does prevent fusion of these rings, but conjugation is possible, since this sp$^3$-hybridized carbon atom in position 9 does not necessarily lie between the carbazole ring of the formula (I) and the dibenzofuran structure (Y=O) and/or the dibenzothiophene structure (Y=S). In contrast, in the case of a spirobifluorene structure, through-conjugation can be formed if the bond between the carbazole ring of the formula (I) and the dibenzofuran structure (Y=O) and/or the dibenzothiophene structure (Y=S) is via the same phenyl group in the spirobifluorene structure or via phenyl groups in the spirobifluorene structure that are bonded directly to one another and are in one plane. If the bond between the carbazole ring of the formula (I) and the dibenzofuran structure (Y=O) and/or the dibenzothiophene structure (Y=S) is via different phenyl groups in the spirobifluorene structure bonded via the sp$^3$-hybridized carbon atom in position 9, the conjugation is interrupted.

In this context, "adjacent carbon atoms" means that the carbon atoms are bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

The definitions which follow are to apply if no other definition or restriction is stated.

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc. In addition, systems in which two or more aromatic or heteroaromatic rings are bonded directly to one another, for example biphenyl or terphenyl, are also aryl or heteroaryl groups.

An aromatic ring system in the context of this invention contains 6 to 60 carbon atoms in the ring system. A heteroaromatic ring system in the context of this invention contains 1 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. are also to be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl- and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

It has been found that compounds of the formula (I) which are used in electronic devices are particularly advantageous, especially with regard to the lifetime of the device.

The connecting $L^1$ or $L^2$ group in formula (I) does not have any fused aromatic rings, and so no naphthylene groups, for example, are present. This includes substituents on the $L^1$ or $L^2$ groups, and so the $R^4$ substituents likewise do not include any fused aromatic rings such as naphthyl groups.

In addition, the connecting $L^1$ or $L^1$ group in formula (I) does not include any heteroaromatic ring systems or heteroaryl groups; for example carbazole groups or pyridine groups are excluded. This includes substituents on the $L^1$ or $L^2$ groups, and so the $R^4$ substituents likewise do not include any heteroaromatic ring systems or heteroaryl groups, such as carbazole groups or pyridine groups.

More preferably, at least one of these $L^1$ or $L^2$ groups comprises at least one phenylene and/or biphenylene group which may be substituted by one or more $R^4$ radicals. It is particularly advantageous for the performance data of electronic devices when $L^1$ is a phenylene group which may be substituted by one or more $R^4$ radicals. It is further preferable when $L^1$ and $L^2$ are a phenylene group which may be substituted in each case by one or more $R^4$ radicals.

It has additionally been found to be advantageous when the (aza-)dibenzofuran or (aza-)dibenzothiophene group bonded via the $L^1$ group to the nitrogen atom in position 9 of the carbazole in formula (I) does not contain any further carbazoles, dibenzofurans or dibenzothiophenes.

It is additionally advantageous when both the (aza-)dibenzofuran or (aza-)dibenzothiophene group bonded via the $L^1$ group to the nitrogen atom in position 9 of the carbazole in formula (I) and the (aza-)dibenzofuran or (aza-)dibenzothiophene group bonded via the $L^2$ group to one of positions 1 to 4 of the carbazole in formula (I) do not contain any further carbazoles, dibenzofurans or dibenzothiophenes.

In a further particularly preferred embodiment, the compound of the formula (I), as well as the central carbazole and the two (aza-)dibenzothiophenes or (aza-)dibenzofurans bonded via $L^1$ and $L^2$ also contains exactly one further dibenzofuran or dibenzothiophene group bonded as R group to the carbazole of the formula (I).

It has further been found that it is particularly advantageous when the compound of the formula (I) contains only one carbazole overall. It is most preferable when the compound of the formula (I) contains one carbazole and exactly two (aza-)dibenzofurans or two (aza-)dibenzothiophenes or one (aza-)dibenzofuran and one (aza-)dibenzothiophene, it being especially preferred when it contains one carbazole and two (aza-) dibenzofurans overall.

An aryl group comprises two or more fused rings if at least two rings each have two ring atoms in common and these rings are each aromatic. Preferably, the aromatic nuclei of at least two rings interact to a greater degree, this interaction being detectable via spectroscopic methods, including changes in fluorescence or phosphorescence or a shift in the UV spectrum. For example, fluorene comprises only two unfused rings, whereas dibenzofuran or dibenzothiofuran are heteroaromatic systems having three fused rings. Anthracene, fluoranthene and other aromatic systems having three or more aromatic rings each having 2 common carbon atoms per ring are fused systems having at least 3 rings. In simplified terms, it can be stated that fused aromatic systems are formed essentially from $sp^2$-hybridized ring carbon atoms. A comparable definition applies to heteroaryl groups.

In addition, the R radicals bonded to the carbazole ring of the formula (I) do not form a fused ring system with the phenyl group of the carbazole ring to which this R group is bonded.

In addition, the R radicals bonded to the carbazole ring of the formula (I) are not a carbazole group or azacarbazole group in which the nitrogen atom of this carbazole group or azacarbazole group is bonded to the carbazole ring of the formula (I). Preferably, the R radicals are not an azacarbazole group.

In a further-preferred embodiment, one of the R radicals in the compound of the formula (I) is a carbazole group not bonded via the nitrogen of the carbazole group (=R group). In this case, it is further preferable when the other R radicals are H.

In a further-preferred embodiment, none of the R radicals in the compound of the formula (I) is a carbazole or azacarbazole group.

In a preferred configuration, it may be the case that the sum total of all the indices h and i is not more than 4, preferably not more than 3, especially preferably not more than 2, particularly preferably not more than 1.

In addition, it may be the case that the sum total of the indices m and n is preferably 1 or 2, more preferably 1.

Preferably, at least one of the $L^1$ or $L^2$ groups in formula (I) may comprise at least one phenylene, biphenylene, fluorenyl and/or spirobifluorenyl group, particular preference being given to a phenylene group.

Preference is additionally given to compounds which are characterized in that the $L^1$ or $L^2$ groups in formula (I) have a total of not more than 36, preferably not more than 24, more preferably not more than 12 and most preferably not more than 6 carbon atoms.

In addition, it may be the case that the R radicals in the carbazole ring of the formula (I) are not bonded to the carbazole ring of the formula (I) via a nitrogen atom. This leads to particularly advantageous performance data of electronic devices comprising these compounds.

In addition, it may be the case that the R radicals in the carbazole ring of the formula (I) have no nitrogen atoms, preferably no heteroatoms.

Preference is further given to compounds comprising structures of the formula (I) in which at least one R radical is a group selected from hydrogen and the formulae (R-1) to (R-22), particular preference being given to those of the formulae (R-1) to (R-14).

Formula (R-1)

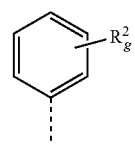

Formula (R-2)
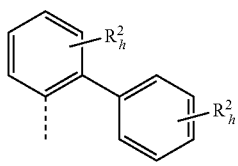
Formula (R-3)
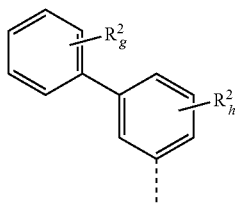
Formula (R-4)
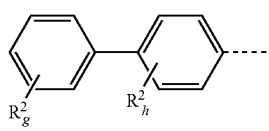
Formula (R-5)
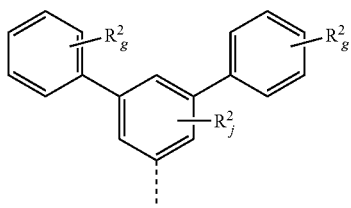
Formula (R-6)
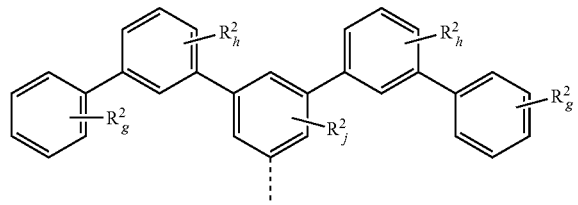
Formula (R-7)
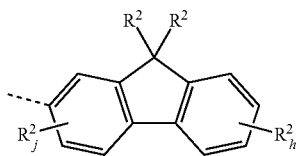
Formula (R-8)
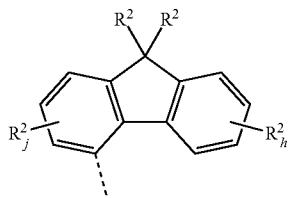
Formula (R-9)
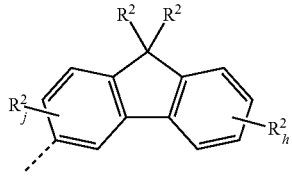
Formula (R-10)
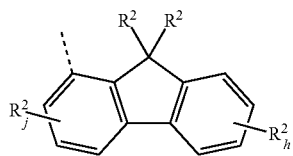
Formula (R-11)
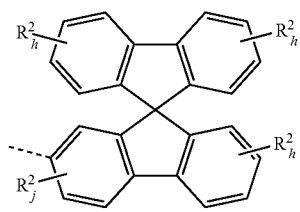
Formula (R-12)
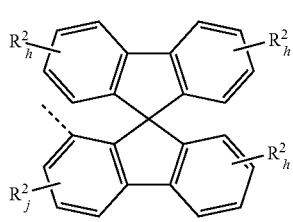
Formula (R-13)
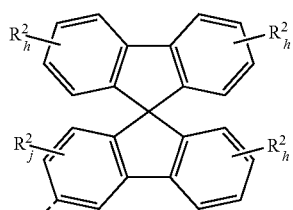
Formula (R-14)
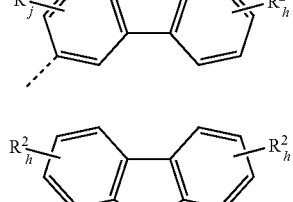
Formula (R-15)
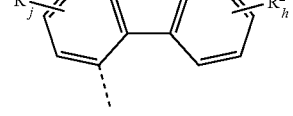
Formula (R-16)
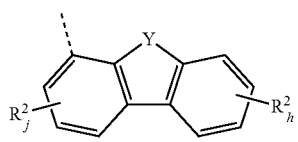
Formula (R-17)
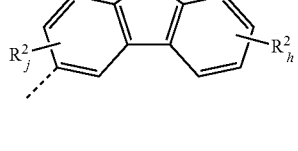

Formula (R-18)

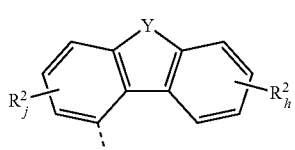

Formula (R-19)

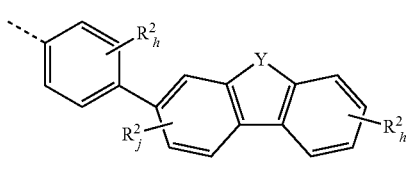

Formula (R-20)

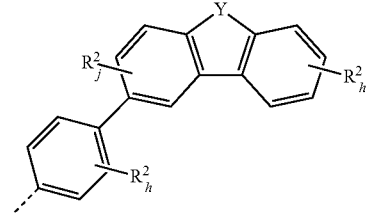

Formula (R-21)

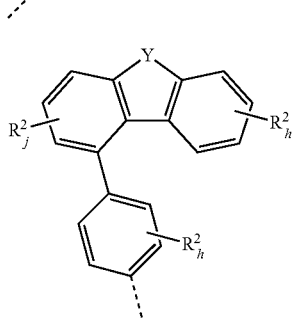

Formula (R-22)

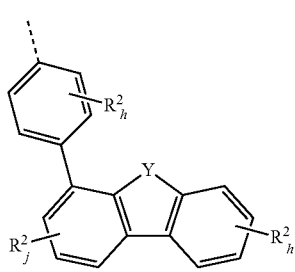

where the dotted bond marks the attachment position, g is 0, 1, 2, 3, 4 or 5, h is 0, 1, 2, 3 or 4, j is 0, 1, 2 or 3, and $R^2$ and Y are as defined above.

It may preferably be the case that the sum total of the indices g, h and j in the structures of the formula (R-1) to (R-22) is at most 3 in each case, preferably at most 2 and more preferably at most 1.

Preference is given to compounds comprising structures of the formula (I) where, in the structure of formula (I), at least one R radical is a group selected from the formulae (R-23) to (R-25)

Formula (R-23)

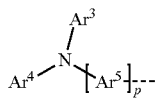

Formula (R-24)

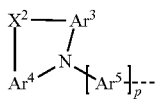

Formula (R-25)

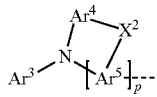

where the dotted bond marks the attachment position and $Ar^3$, $Ar^4$, $Ar^5$ are each independently an aromatic ring system, preferably an aryl group, having 6 to 40 carbon atoms or a heteroaromatic ring system, preferably a heteroaryl group, having 3 to 40 carbon atoms, each of which may be substituted by one or more $R^1$ radicals;

p is 0 or 1 and $X^2$ is a bond, $CR^1_2$, C=O, $N(R^1)$, $B(R^1)$, $SiR^1_2$, O or S, preferably $CR^1_2$, C=O, $N(Ar^1)$, O or S, where the $R^1$ and $Ar^1$ radicals are as defined above.

Preferred compounds having structures of formula (I), or the preferred embodiments detailed above and below, preferably have the feature that at least one Y in the structure of formula (I) is O, and preferably both Y in the structure of formula (I) are O.

In addition, it may be the case that at least one Y in the structure of formula (I) is S.

Preference is additionally given to compounds in which, in the structure of formula (I), not more than one X is N, and preferably no X is N.

Preference is given to compounds comprising structures of the formula (I) in which at least one $R^1$ radical is a group selected from the formulae ($R^1$-1) to ($R^1$-22)

Formula ($R^1$-1)

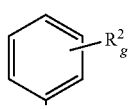

Formula ($R^1$-2)

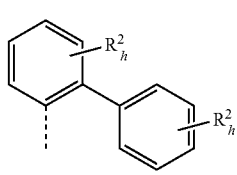

Formula ($R^1$-3)

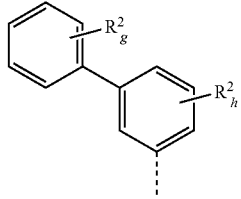

Formula ($R^1$-4)

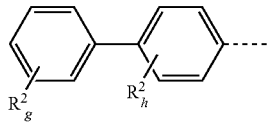

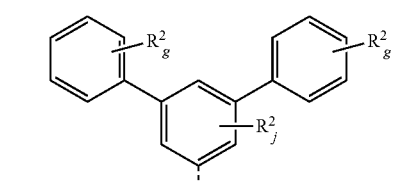
Formula (R¹-5)
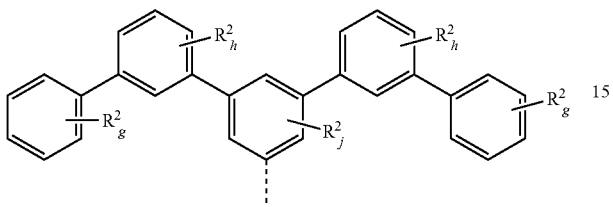
Formula (R¹-6)
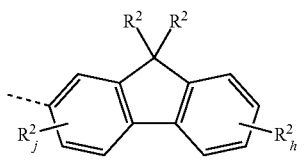
Formula (R¹-7)
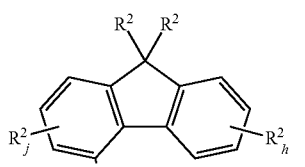
Formula (R¹-8)
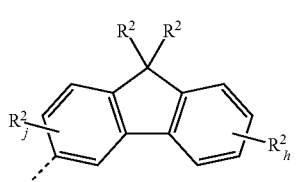
Formula (R¹-9)
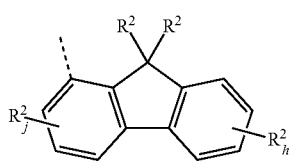
Formula (R¹-10)
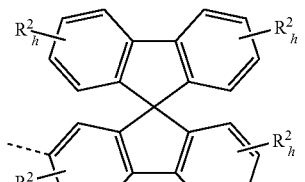
Formula (R¹-11)
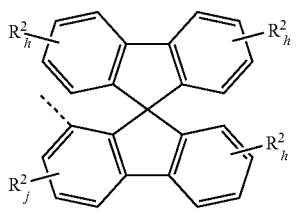
Formula (R¹-12)
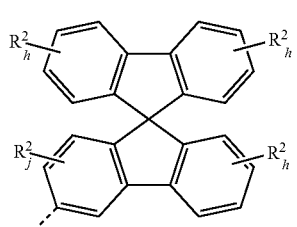
Formula (R¹-13)
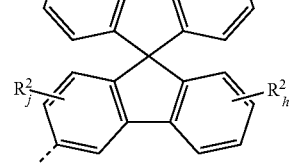
Formula (R¹-14)
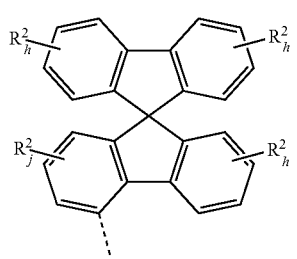
Formula (R¹-15)
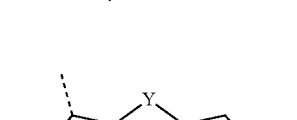
Formula (R¹-16)
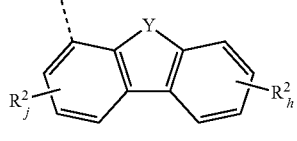
Formula (R¹-17)
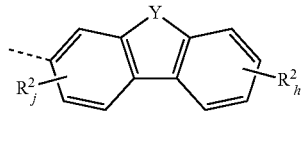
Formula (R¹-18)
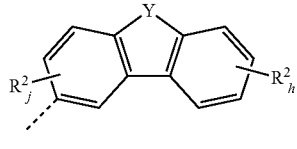
Formula (R¹-19)
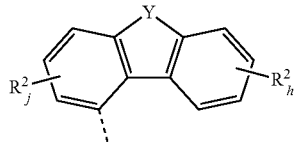
Formula (R¹-20)
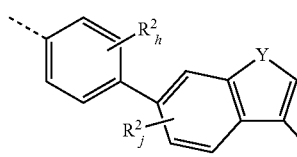
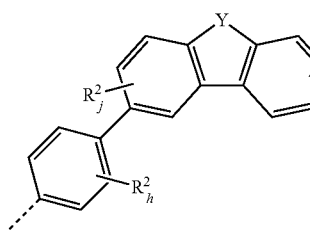

-continued

Formula (R¹-21)

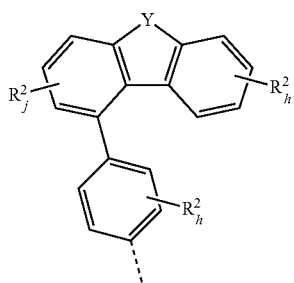

Formula (R¹-22)

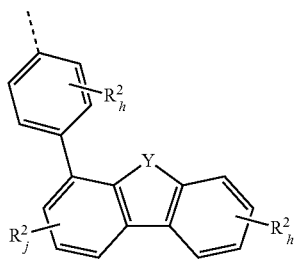

where the dotted bond marks the attachment position, g is 0, 1, 2, 3, 4 or 5, h is 0, 1, 2, 3 or 4, j is 0, 1, 2 or 3, and $R^2$ and Y are as defined above.

It is preferable when the $R^1$ radical is not a carbazole ring.

It may preferably be the case that the sum total of the indices g, h and j in the structures of the formula (R¹-1) to (R¹-22) is not more than 3 in each case, preferably not more than 2 and more preferably not more than 1.

Preference is given to compounds comprising structures of the formula (I) where, in the structure of formula (I), at least one $R^1$ radical is a group selected from the formulae (R¹-23) to (R¹-25)

Formula (R¹-23)

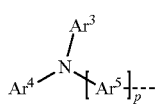

Formula (R¹-24)

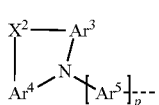

Formula (R¹-25)

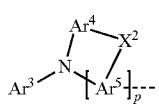

where the dotted bond marks the attachment position and $Ar^3$, $Ar^4$, $Ar^5$ are each independently an aromatic ring system, preferably an aryl group, having 6 to 40 carbon atoms or a heteroaromatic ring system, preferably a heteroaryl group, having 3 to 40 carbon atoms, each of which may be substituted by one or more $R^1$ radicals; p is 0 or 1 and $X^2$ is a bond, $CR^1_2$, C=O, $N(R^1)$, $B(R^1)$, $SiR^1_2$, O or S, preferably $CR^1_2$, C=O, $N(Ar^1)$, O or S, where the $R^1$ and $Ar^1$ radicals are as defined above.

Preference is given to compounds comprising structures of the formulae (I) where, in the structure of formula (I), at least one group selected from $L^1$, $L^2$ is a group selected from the formulae (L-1) to (L-12), particular preference being given to the group of the formula (L-1)

Formula (L-1)

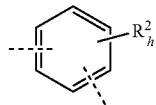

Formula (L-2)

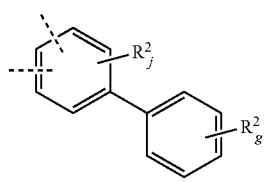

Formula (L-3)

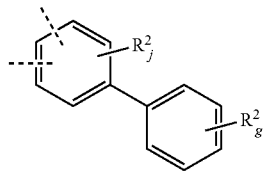

Formula (L-4)

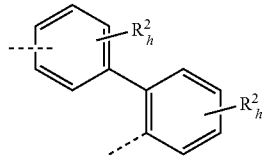

Formula (L-5)

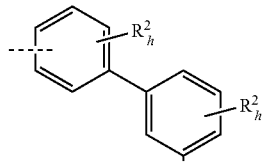

Formula (L-6)

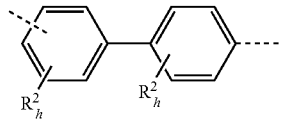

Formula (L-7)

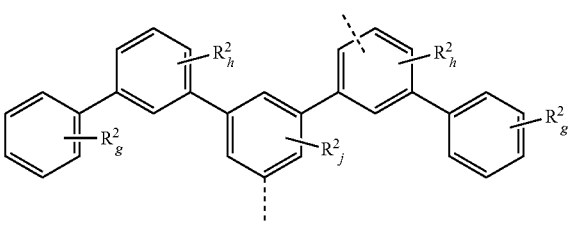

Formula (L-8)

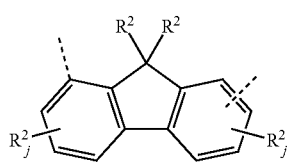

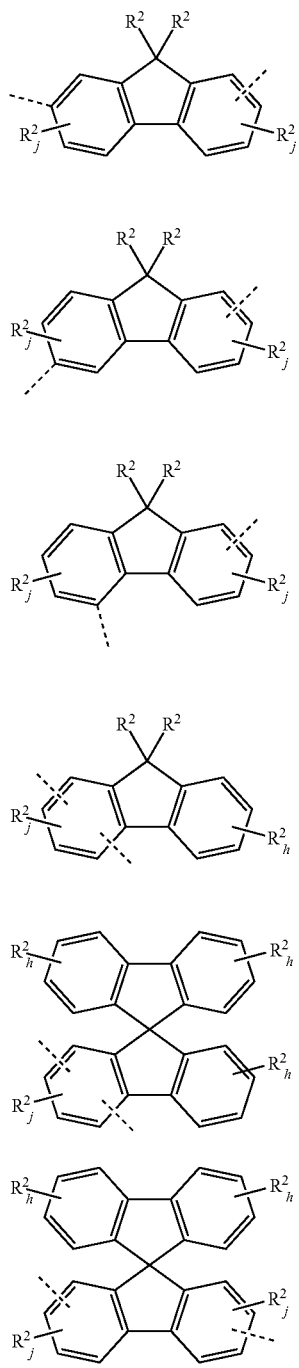

Formula (L-9)

Formula (L-10)

Formula (L-11)

Formula (L-12)

Formula (L-13)

Formula (L-14)

where the dotted bonds each mark the attachment positions, the index l is 0, 1 or 2, the index g is 0, 1, 2, 3, 4 or 5, preferably 0, 1, 2 or 3, more preferably 0, 1 or 2, the index h is 0, 1, 2, 3 or 4, preferably 0, 1 or 2, more preferably 0 or 1, the index j is 0, 1, 2 or 3, preferably 0, 1 or 2, more preferably 0 or 1, and $R^2$ is as defined above.

Preferably, the sum total of the indices h, j, g and l in a structure of the formulae (L-1) to (L-14) is not more than 5, preferably 0, 1, 2 or 3 and more preferably 0 or 1.

Particularly preferred compounds include structures according to the following formulae (II), (III), (IV), (V):

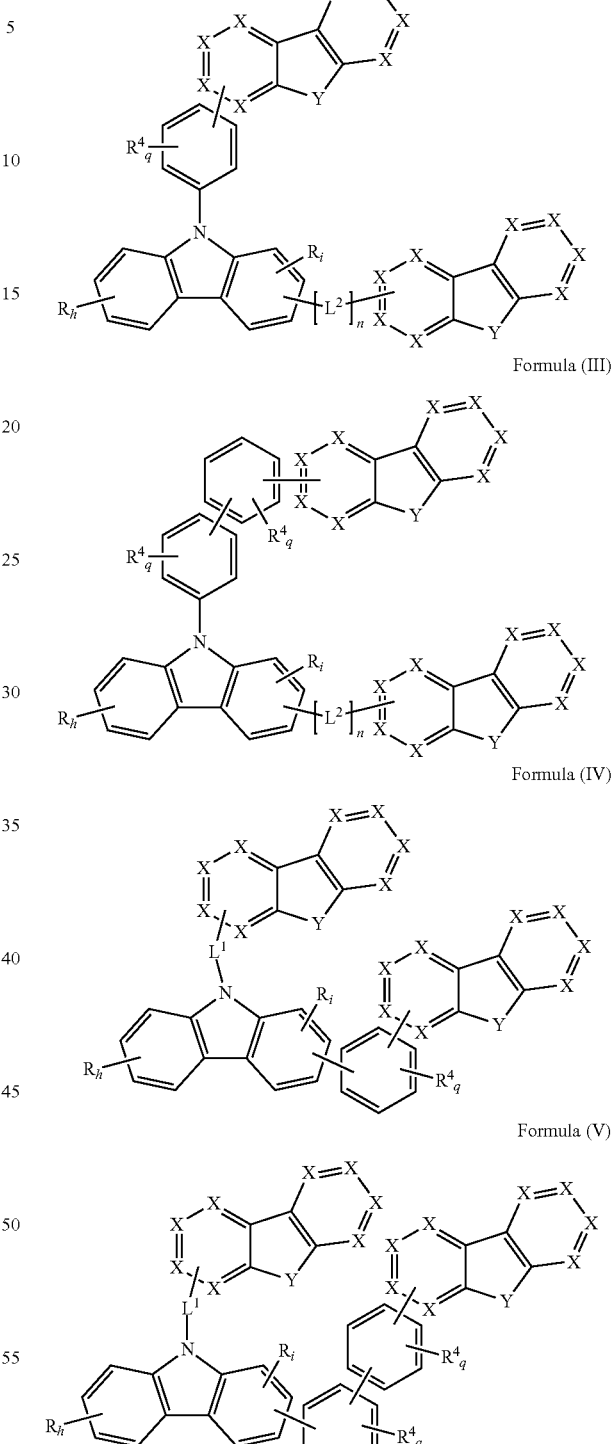

Formula (II)

Formula (III)

Formula (IV)

Formula (V)

where the symbols X, Y, R, $R^4$, $L^1$, $L^2$ shown and the indices h, i and n are each as defined above and the index q is 0, 1, 2, 3 or 4, preferably 0, 1, 2 or 3 and more preferably 0, 1 or 2.

It may additionally be the case that the R, $R^1$, $R^2$, $R^3$ and $R^4$ radicals and the $L^1$, $L^2$ groups have a total of not more than 4, preferably not more than 3, more preferably not more than 2, especially preferably not more than 1 and most preferably no nitrogen atom(s).

Particular preference is given to compounds having structures of the formula (II) in which the L² group has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1). Preference is additionally given to compounds having structures of formula (II) in which n=0, such that a bond between the carbazole ring and the dibenzofuran or dibenzothiophene structure is envisaged.

Particular preference is given to compounds having structures of the formula (III) in which the L² group has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1). Preference is additionally given to compounds having structures of formula (III) in which n=0, such that a bond between the carbazole ring and the dibenzofuran or dibenzothiophene structure is envisaged.

Particular preference is given to compounds having structures of the formula (IV) in which the L¹ group has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (V) in which the L¹ group has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particularly preferred compounds comprise structures of the following formulae (VI), (VII), (VIII), (IX), (X), (XI), (XII) and/or (XIII):

Formula (VI)

Formula (VII)

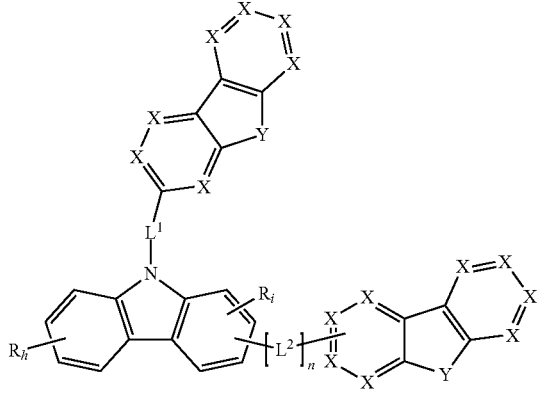

Formula (VIII)

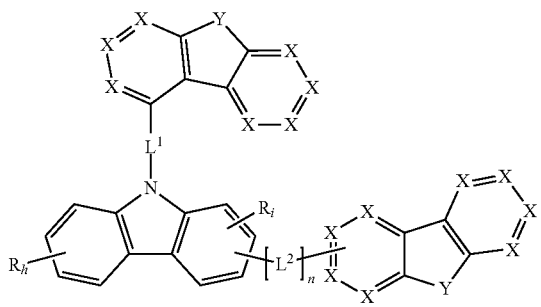

Formula (IX)

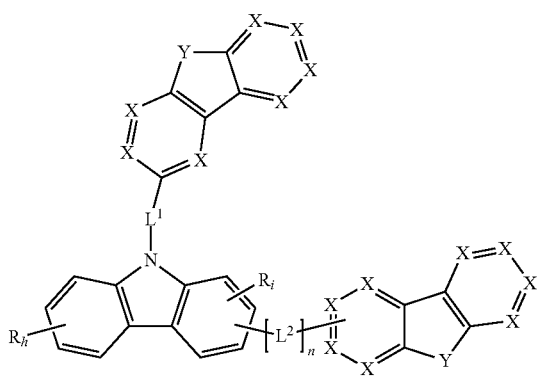

Formula (X)

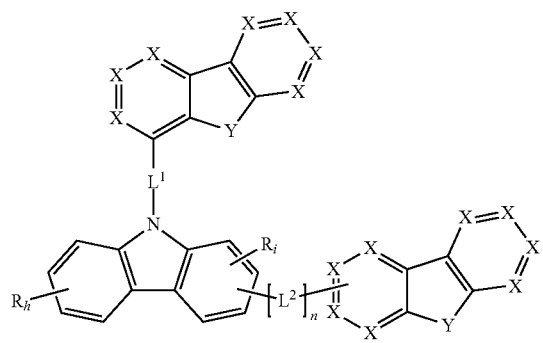

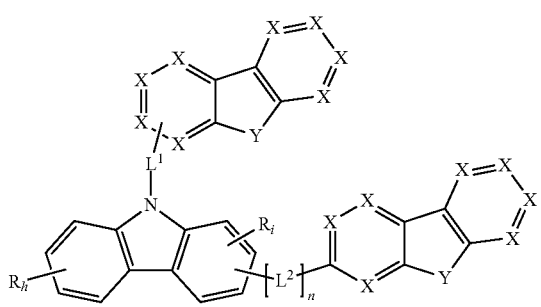

Formula (XI)

Formula (XII)

Formula (XIII)

where the symbols X, Y, R, $L^1$, $L^2$ shown and the indices h, i and n are as defined above.

Particular preference is given to compounds having structures of the formula (VI) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (VII) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (VIII) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (VIII) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (IX) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (X) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (XI) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (XI) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (XII) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Particular preference is given to compounds having structures of the formula (XIII) in which at least one of the $L^1$ and/or $L^2$ groups has a structure of formula (L-1), (L-2), (L-3), (L-4), (L-5), (L-6), (L-7), (L-8), (L-9), (L-10), (L-11), (L-12), (L-13) and/or (L-14), preference being given to structures of formula (L-1), (L-2), (L-3), (L-4), (L-5), (L-6) and/or (L-7) and particular preference to structures of formula (L-1), (L-2), (L-3), (L-4) and/or (L-5), and very particular preference being given to the structure of the formula (L-1).

Preferably, a compound having structures of formula (I) and preferred variants of this compound of formulae (II) to (XIII) may comprise R and/or $R^1$ radicals in which these R and/or $R^1$ radicals are the same or different at each instance and are preferably selected from the group consisting of H, D, F, Br, I, CN, $Si(R^2)_3$, $B(OR^2)_2$, $C(=O)Ar^1$, a straight-chain alkyl group having 1 to 10 carbon atoms or a straight-chain alkoxy group having 1 to 10 carbon atoms or an alkenyl group having 2 to 10 carbon atoms or a branched or cyclic alkoxy group having 3 to 10 carbon atoms or a branched or cyclic alkyl group having 3 to 10 carbon atoms, each of which may be substituted by one or more $R^2$ radicals, where one or more hydrogen atoms may be replaced by D or F, or an aromatic or heteroaromatic ring system which has 5 to 30 aromatic ring atoms and may be substituted in each case by one or more $R^2$ radicals; at the same time, two adjacent R or $R^1$ radicals together or R or $R^1$ radicals together with $R^2$ radicals may also form a mono- or polycyclic, aliphatic or aromatic ring system. More preferably, these R or $R^1$ radicals are the same or different at each instance and are selected from the group consisting of H, D, F, a straight-chain alkoxy group having 1 to 6 carbon atoms or a branched or cyclic alkoxy group having 3 to 10 carbon atoms, a straight-chain alkyl group having 1 to 6 carbon atoms or a branched or cyclic alkyl group having 3 to 10 carbon atoms, where one or more hydrogen atoms may be replaced by D or F, or an aromatic or heteroaromatic ring system which has 5 to 24 aromatic ring atoms and may be substituted in each case by one or more $R^2$ radicals; at the same time, two adjacent R or $R^1$ radicals together or R or $R^1$ radicals together with $R^2$ radicals may also form a mono- or polycyclic, aliphatic or aromatic ring system. More preferably, at least one of the R or $R^1$ radicals in formula (I) may be an aryl group or a heteroaryl group which has 6 to 18 carbon atoms and may be substituted by up to three $R^2$ radicals.

Preferably, the compound having structures of formula (I) and preferred variants of this compound of formulae (I) to (XIII) may comprise $R^2$ radicals in which these $R^2$ radicals are the same or different at each instance and are preferably selected from the group consisting of H, D, F, Cl, Br, I, CHO, $C(=O)Ar^1$, $P(=O)(Ar^1)_2$, $S(=O)Ar^1$, $S(=O)_2Ar^1$, CN, $NO_2$, $Si(R^3)_3$, $B(OR^3)_2$, $OSO_2R^3$, a straight-chain alkyl, alkoxy or thioalkoxy group having 1 to 10 carbon atoms or a branched or cyclic alkyl, alkoxy or thioalkoxy group having 3 to 10 carbon atoms, each of which may be substituted by one or more $R^3$ radicals, where one or more nonadjacent $CH_2$ groups may be replaced by $C\equiv C$, $Si(R^3)_2$, $Ge(R^3)_2$, $Sn(R^3)_2$, $C=O$, $C=S$, $C=Se$, $P(=O)(R^3)$, SO, $SO_2$, O, S or $CONR^3$ and where one or more hydrogen atoms may be replaced by D, F, Cl, Br, I, CN or $NO_2$, or an aromatic or heteroaromatic ring system which has 5 to 24 aromatic ring atoms and may be substituted in each case by one or more $R^3$ radicals, or an aryloxy or heteroaryloxy group which has 5 to 24 aromatic ring atoms and may be substituted by one or more $R^3$ radicals, or a combination of these systems; at the same time, two or more adjacent $R^2$ substituents together may also form a mono- or polycyclic, aliphatic or aromatic ring system. More preferably, at least one of the $R^2$ radicals in formula (I) or the preferred configurations thereof may be an aryl group or a heteroaryl group which has 6 to 18 carbon atoms and may be substituted by up to three $R^3$ radicals.

Preferably, the compound having structures of formulae (I) to (XIII) may comprise $R^4$ radicals in which these $R^4$ radicals are the same or different at each instance and are preferably selected from the group consisting of H, D, F, Cl, Br, I, CHO, $C(=O)Ar^2$, $P(=O)(Ar^2)_2$, $S(=O)Ar^2$, $S(=O)_2Ar^2$, CN, $NO_2$, $Si(R^5)_3$, $B(OR^5)_2$, $OSO_2R^5$, a straight-chain alkyl, alkoxy or thioalkoxy group having 1 to 10 carbon atoms or a branched or cyclic alkyl, alkoxy or thioalkoxy group having 3 to 10 carbon atoms, each of which may be substituted by one or more $R^3$ radicals, where one or more nonadjacent $CH_2$ groups may be replaced by $C\equiv C$, $Si(R^5)_2$, $Ge(R^5)_2$, $Sn(R^5)_2$, $C=O$, $C=S$, $C=Se$, $P(=O)(R^5)$, SO, $SO_2$, O, S or $CONR^5$ and where one or more hydrogen atoms may be replaced by D, F, Cl, Br, I, CN or $NO_2$, or an aromatic ring system which has 6 to 24 carbon atoms, which does not have any fused aromatic rings and which may be substituted in each case by one or more $R^5$ radicals, or an aryloxy group which has 5 to 24 carbon atoms and may be substituted by one or more $R^5$ radicals, or a combination of these systems; at the same time, two or more adjacent $R^4$ substituents together may also form a mono- or polycyclic, aliphatic ring system, but one which does not have any fused aromatic rings. More preferably, at least one of the $R^4$ radicals in formulae (II) to (XIII) may be an aryl group which has 6 to 18 carbon atoms and may be substituted by up to three $R^5$ radicals.

In addition, it may be the case that the X and/or R groups in the structures of the formula (I) and preferred variants of these structures of formulae (II) to (XIII) do not have any anthracene group or any carbazole group bonded via the nitrogen atom to the carbazole of the formulae (I) to (XIII).

Especially preferred compounds are those of the formulae (I) to (XIII) where $L^1$ is a phenylene group, especially a phenylene group of the formula (L-1) and where h+i=0.

Other especially preferred compounds are those of the formulae (I) to (XIII) where $L^1$ is a phenylene group, especially a phenylene group of the formula (L-1) and where h+i=1, it being even more preferable when the R group is a group containing a dibenzothiophene, dibenzofuran or carbazole, where the carbazole group is not bonded via the nitrogen atom to the carbazole of the formula (I). In this connection, the groups of the formulae (R-15) to (R-22) are particularly preferred dibenzothiophenes or dibenzofurans.

Particularly preferred compounds include structures according to the following formulae 1 to 55:

Formula 1
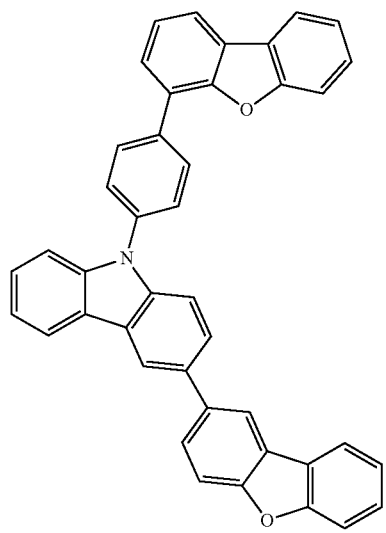
Formula 2
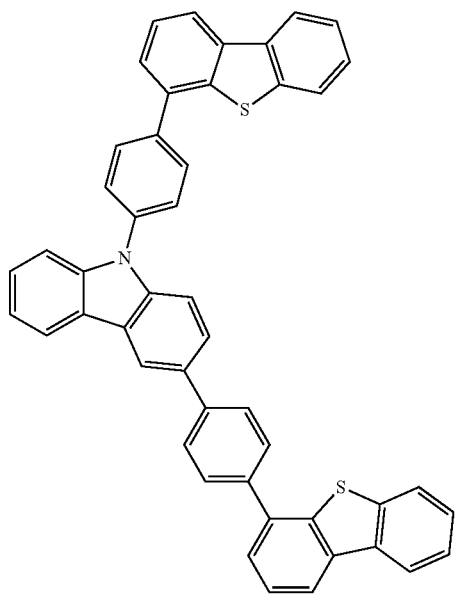
Formula 3
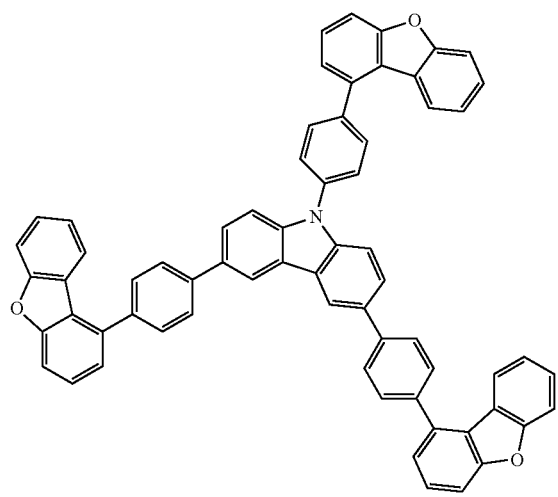
Formula 5
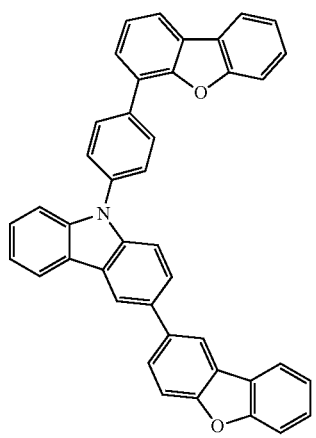

-continued
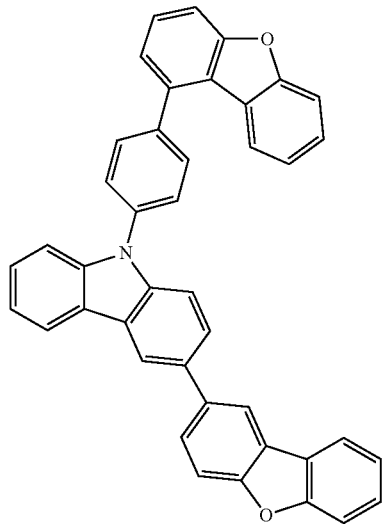
Formula 6
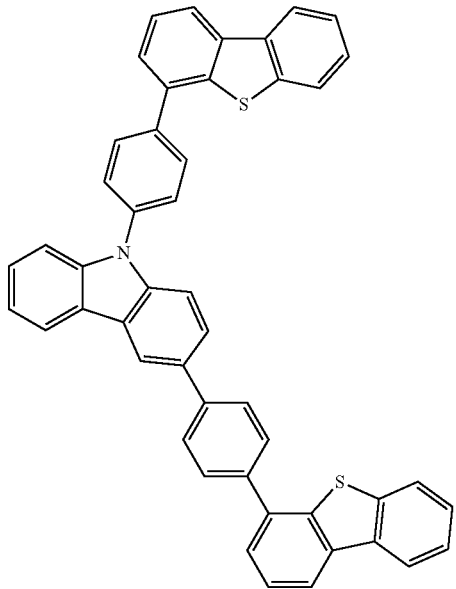
Formula 7
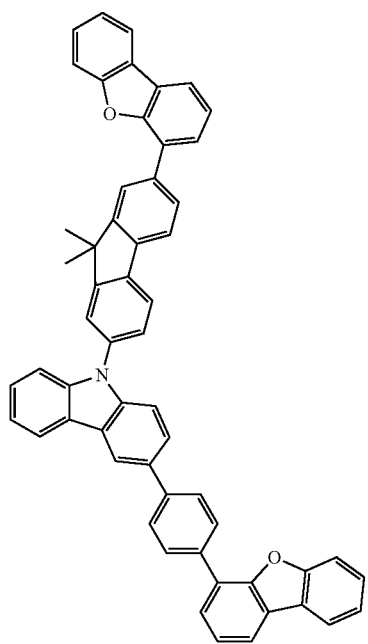
Formula 8

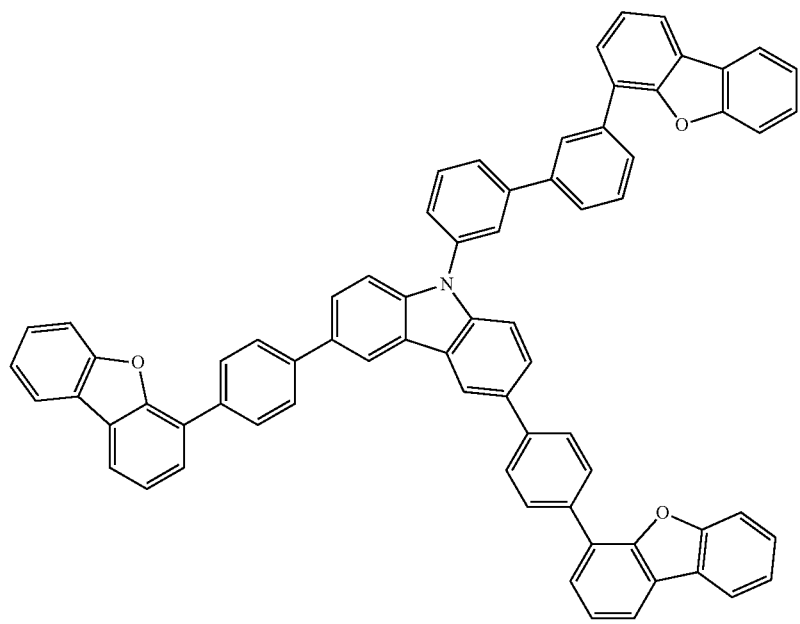
Formula 13
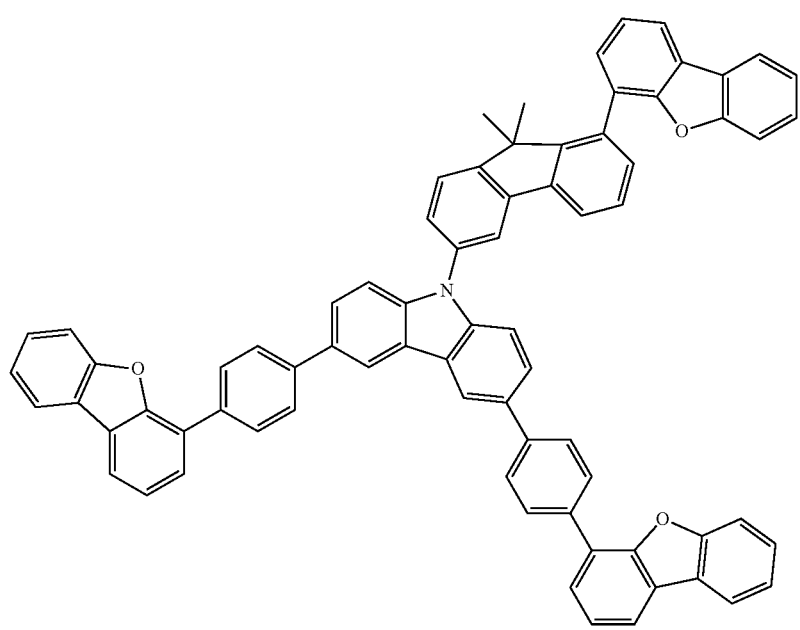
Formula 14

Formula 16
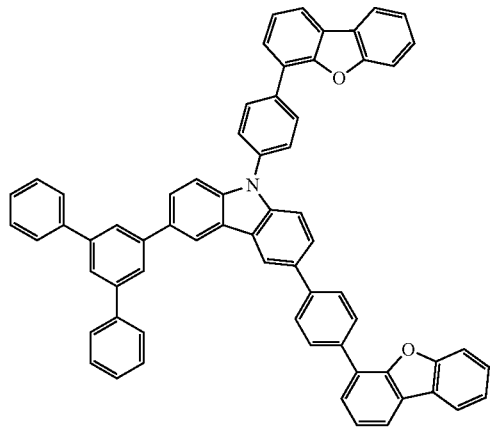
Formula 17
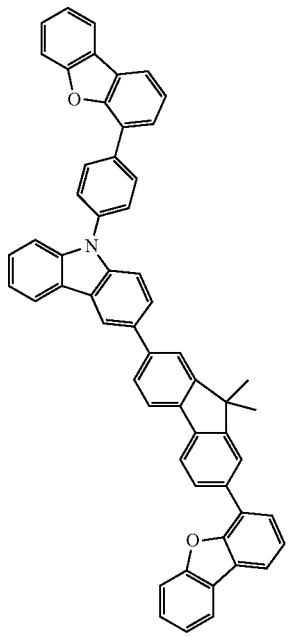
Formula 18
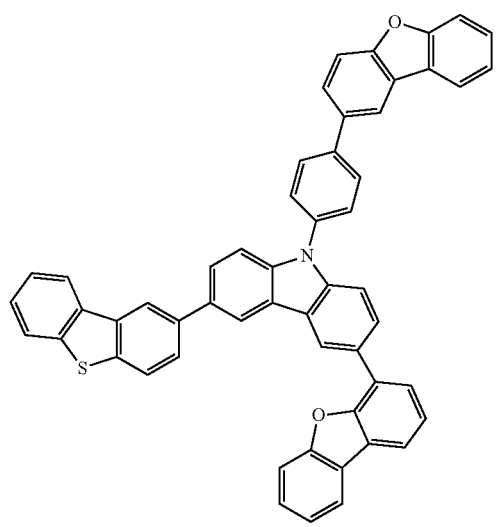
Formula 19
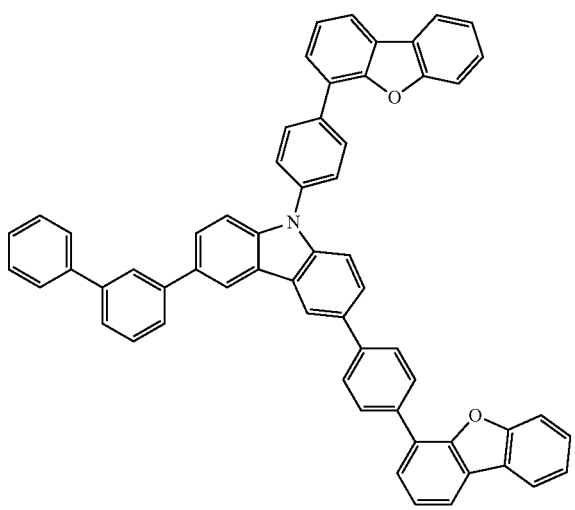

Formula 20
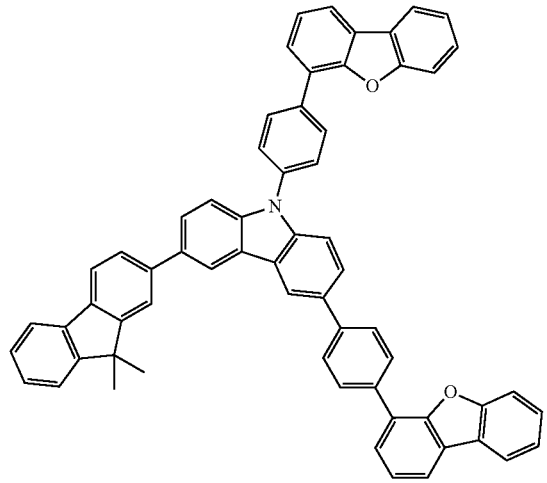
Formula 21
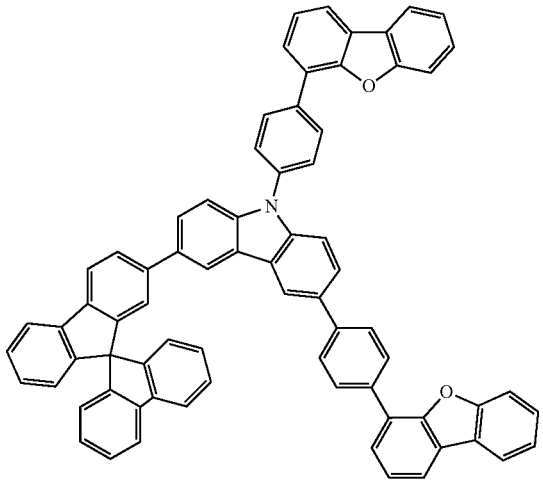
Formula 22
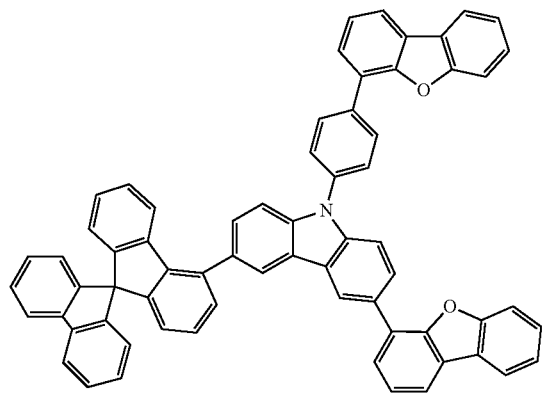
Formula 23
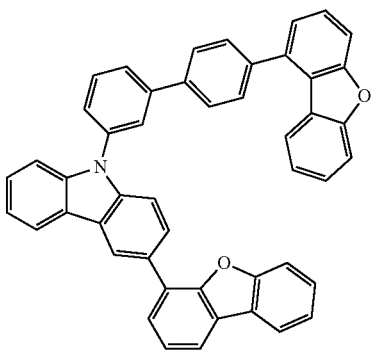
Formula 24
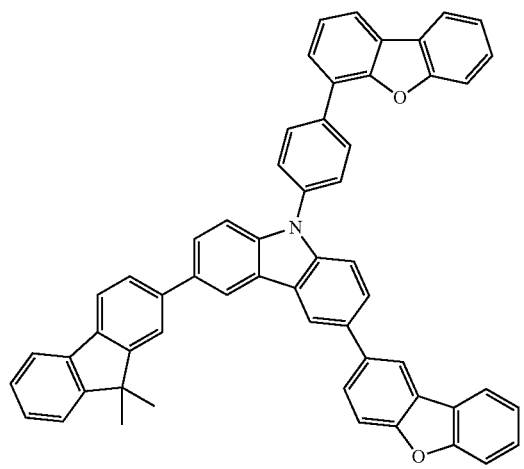
Formula 25
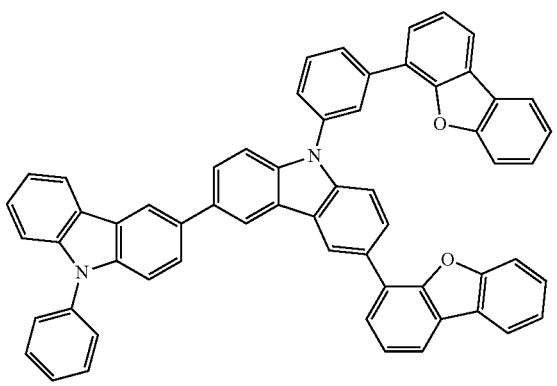

-continued
Formula 26
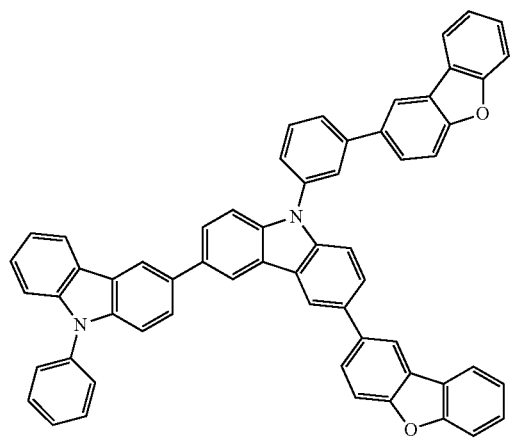
Formula 27
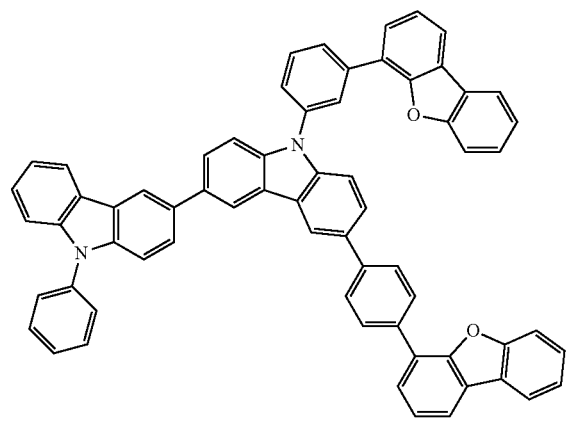
Formula 28
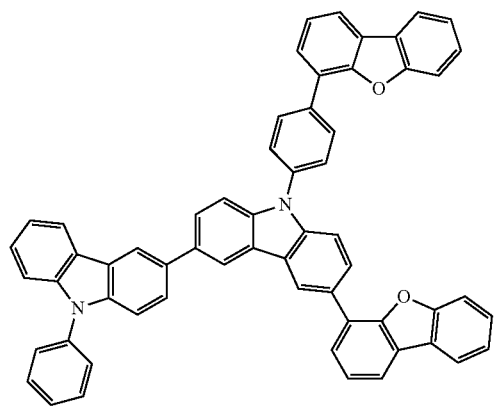
Formula 29
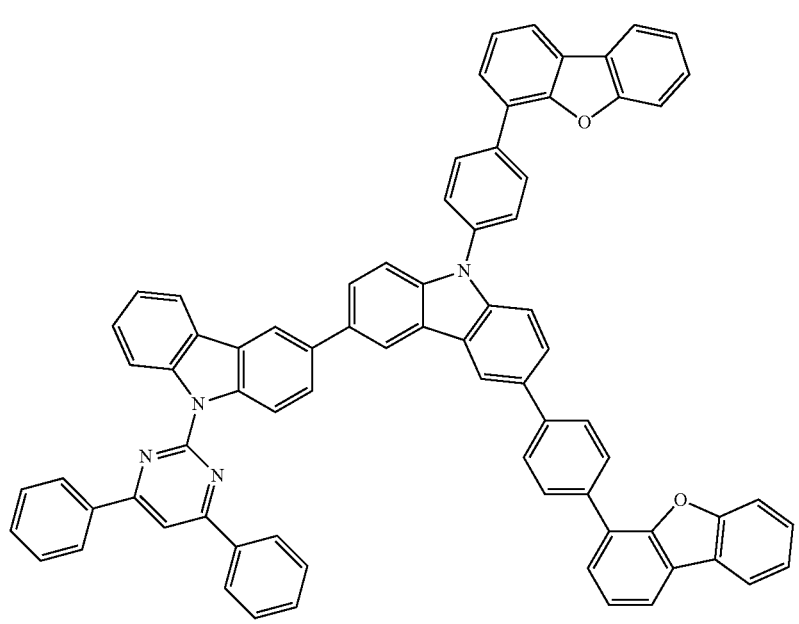

-continued
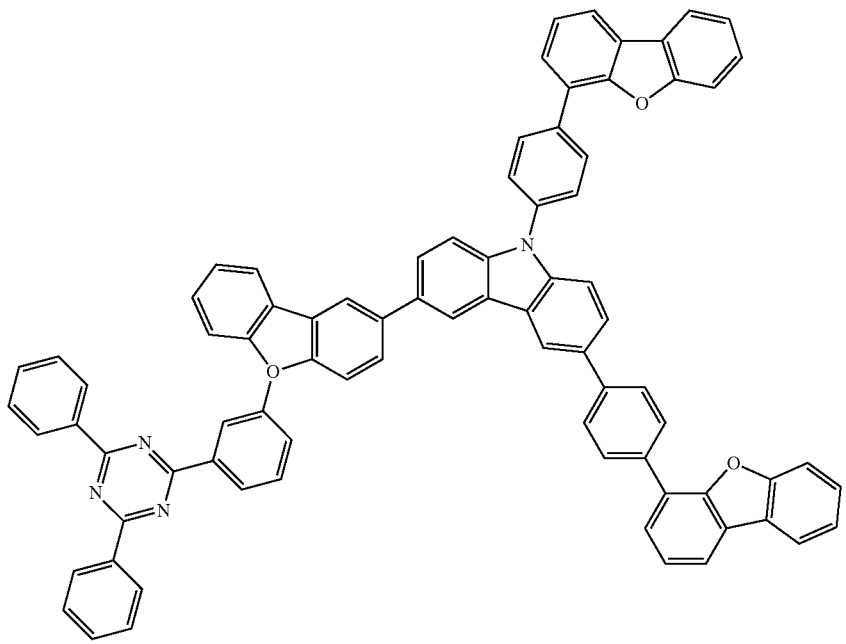
Formula 30
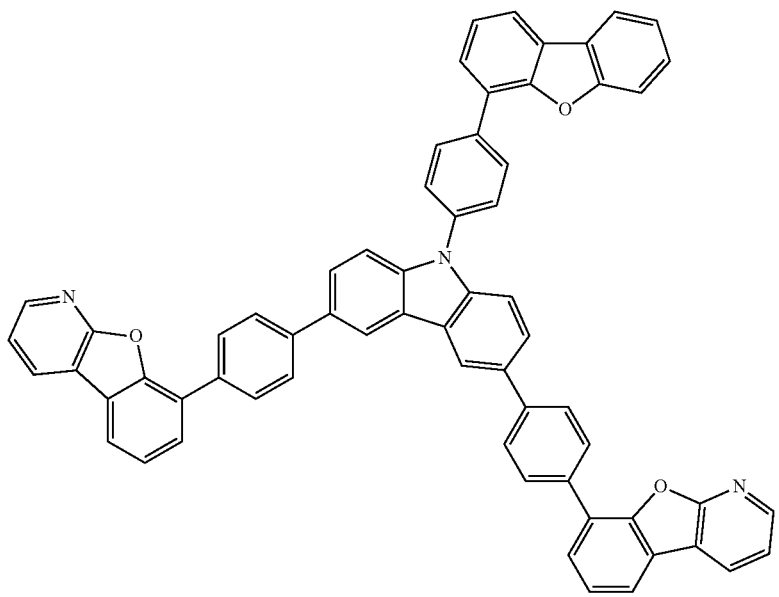
Formula 31

-continued
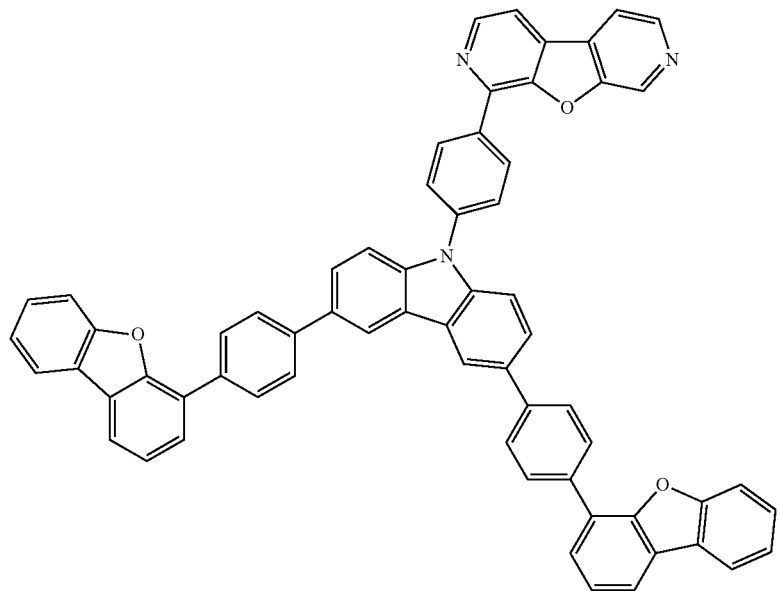
Formula 32
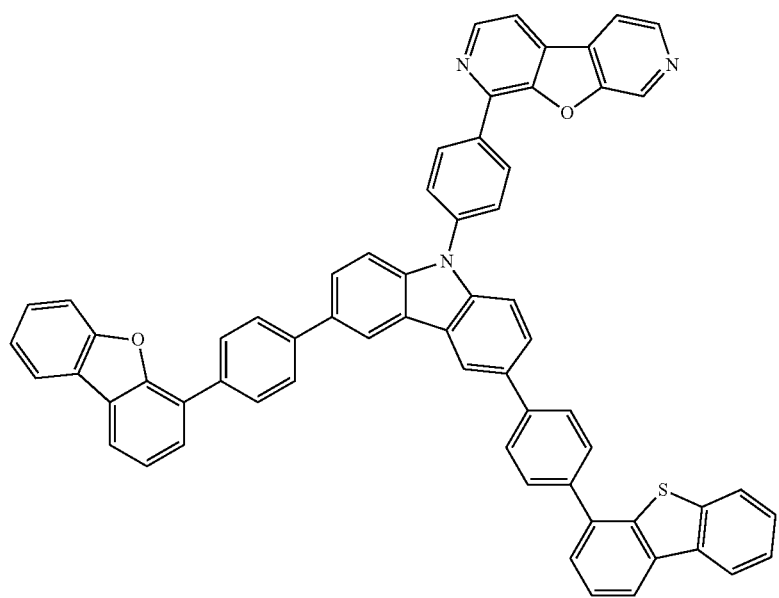
Formula 33

-continued
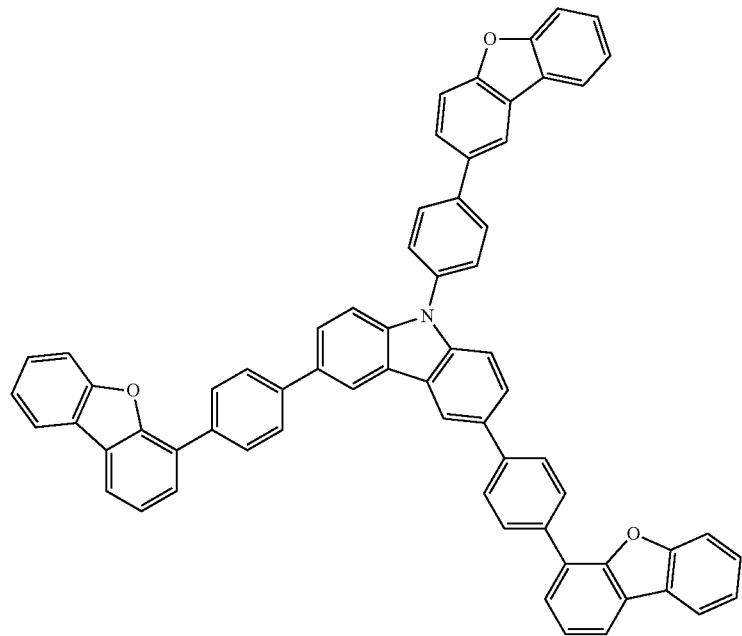
Formula 34
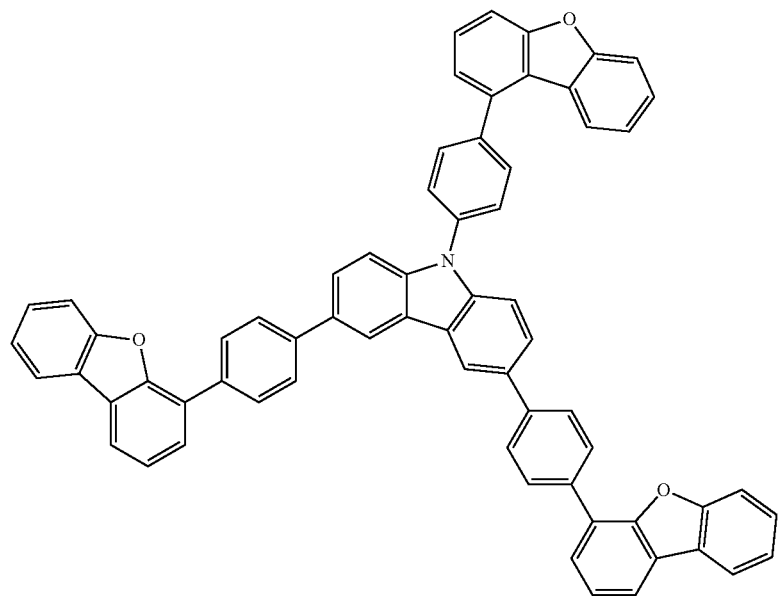
Formula 35

-continued
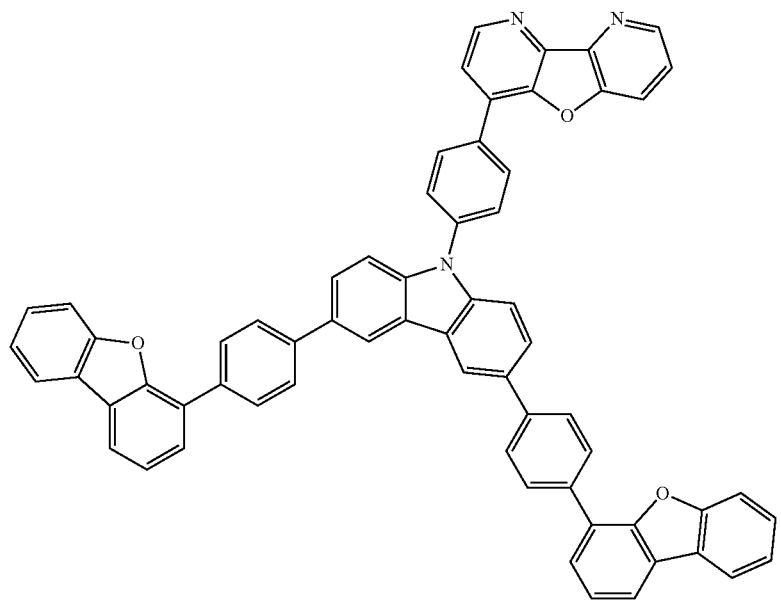
Formula 36
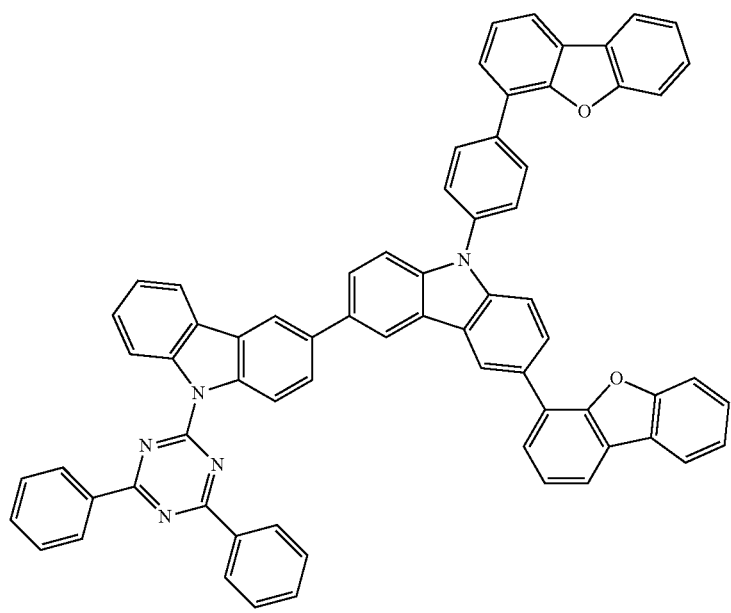
Formula 37

Formula 38
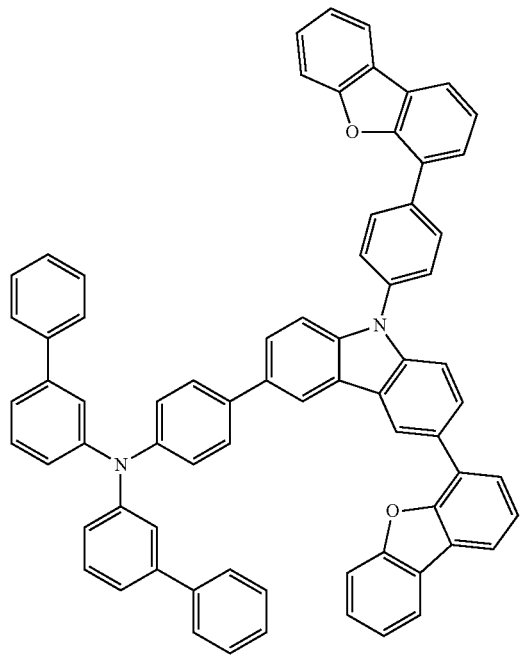
Formula 40
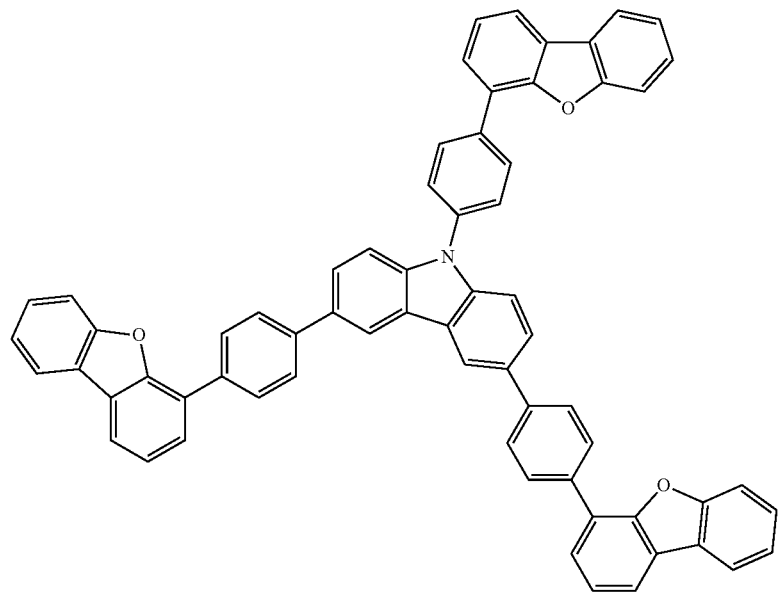

-continued
Formula 41
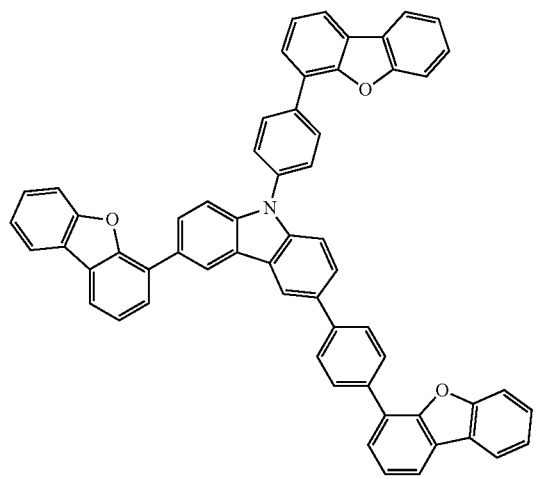
Formula 42
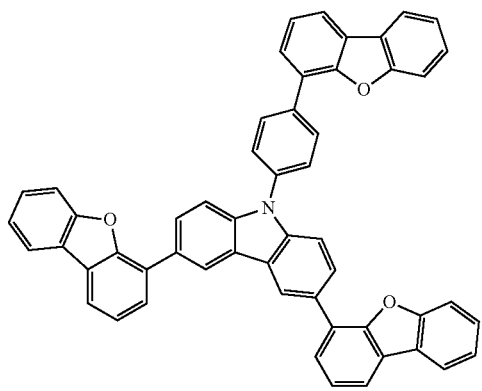
Formula 44
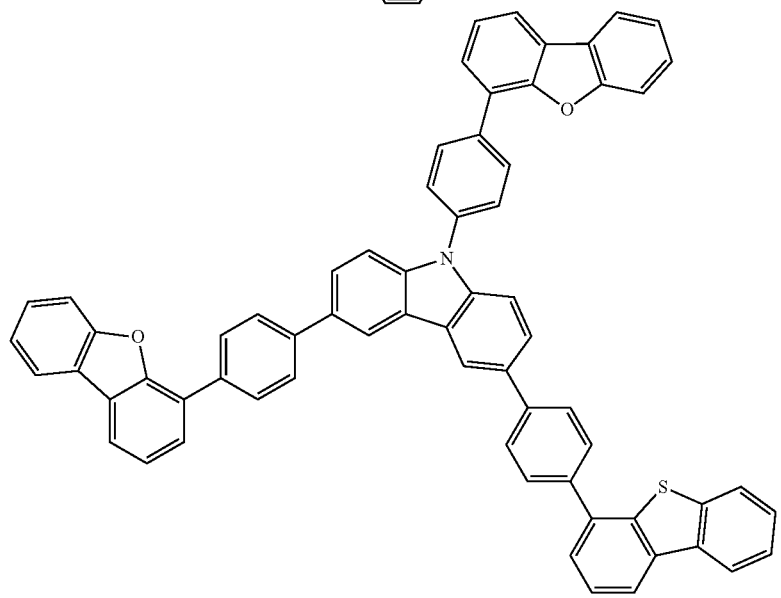
Formula 45
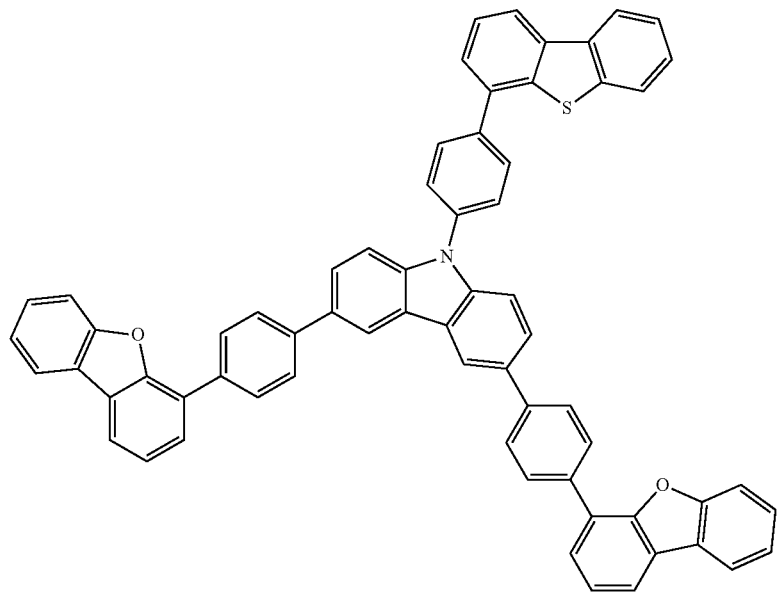

-continued
Formula 47
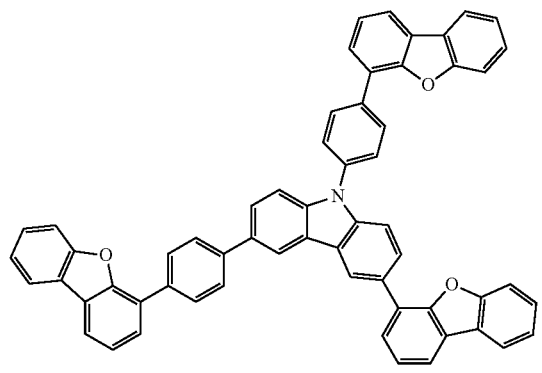
Formula 48
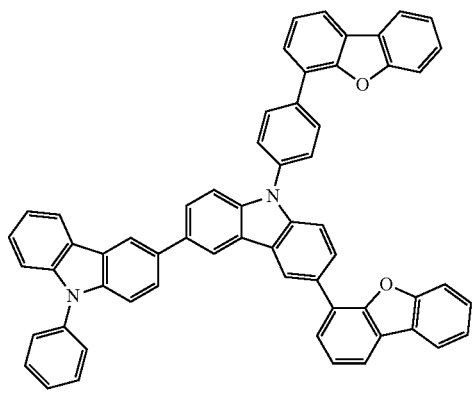
Formula 49
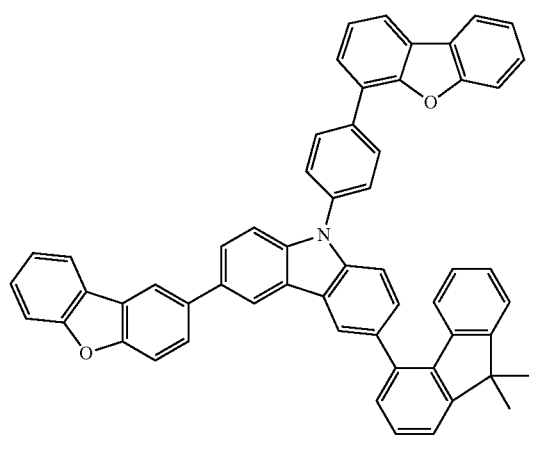
Formula 50
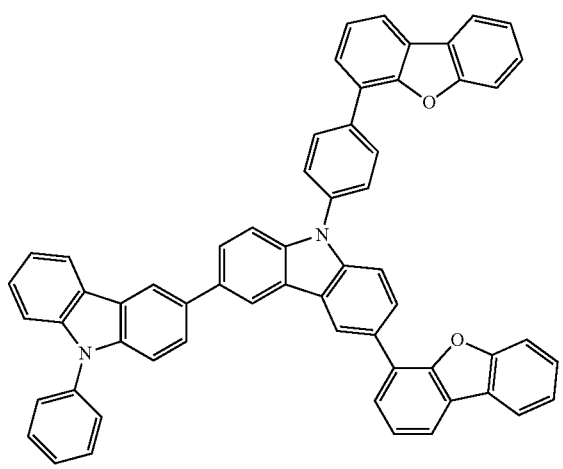
Formula 51
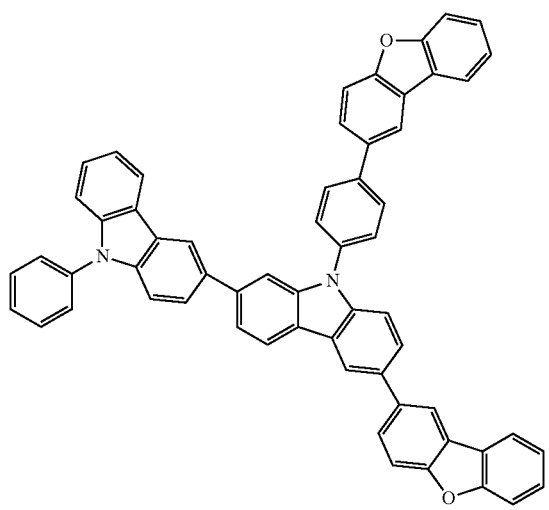
Formula 52
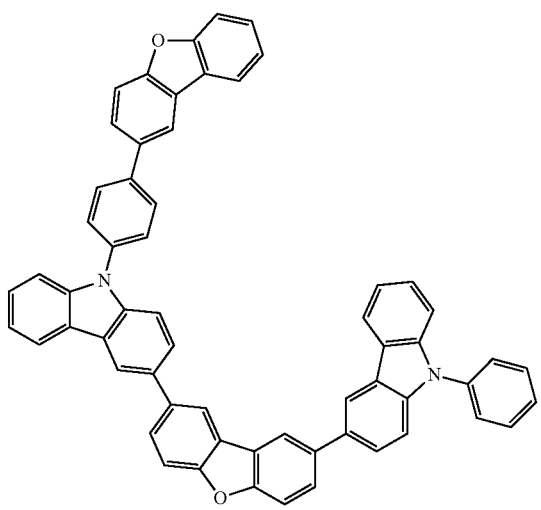

-continued
Formula 53
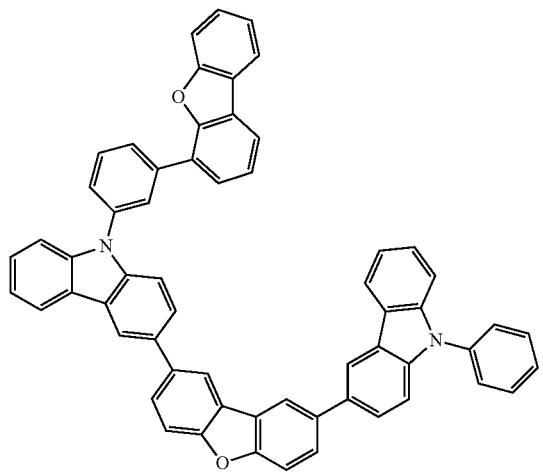
Formula 54
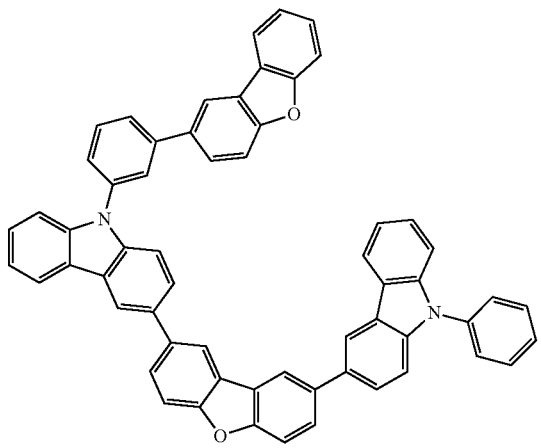
Formula 55
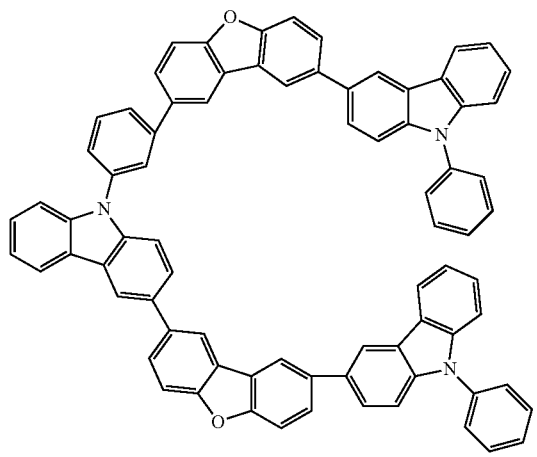
Formula 56
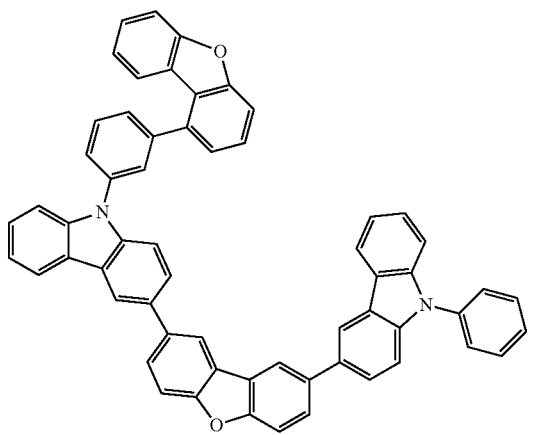
Formula 57
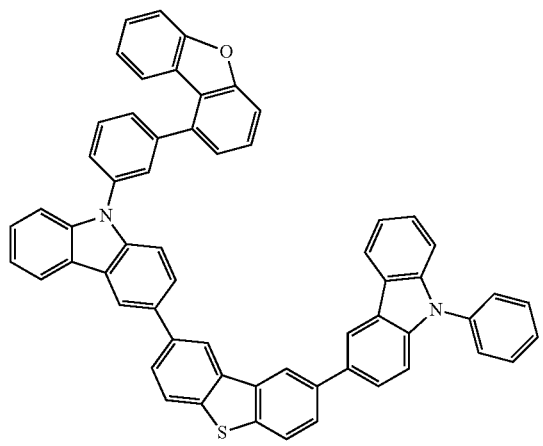
Formula 58
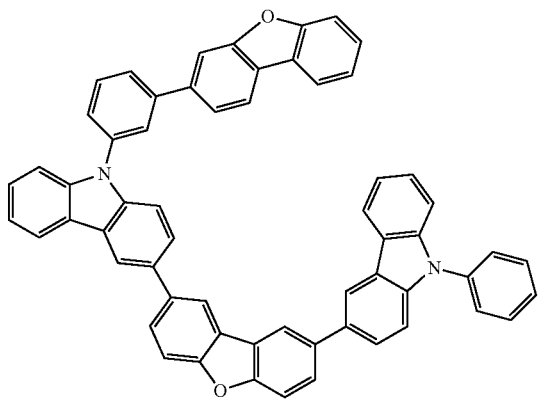

-continued
Formula 59
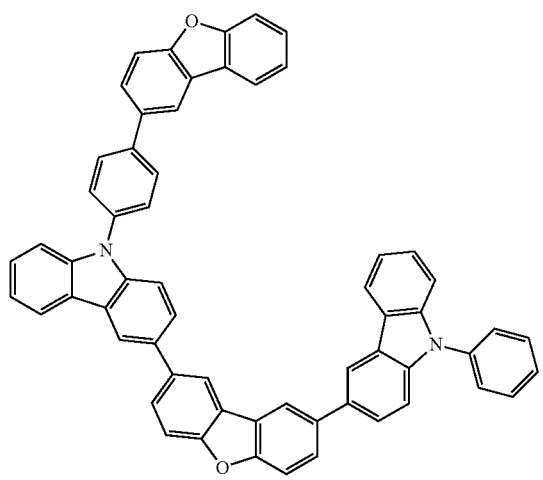
Formula 60
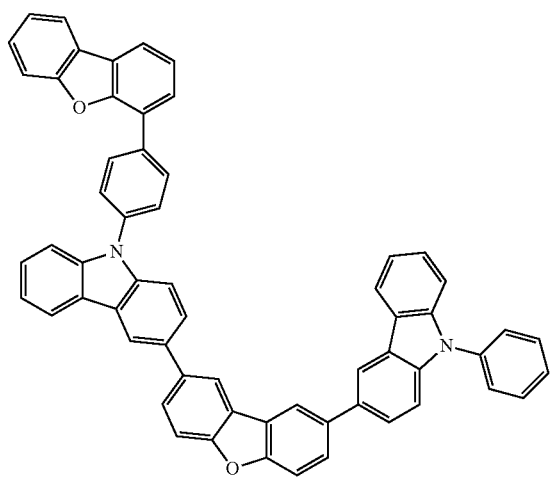
Formula 61
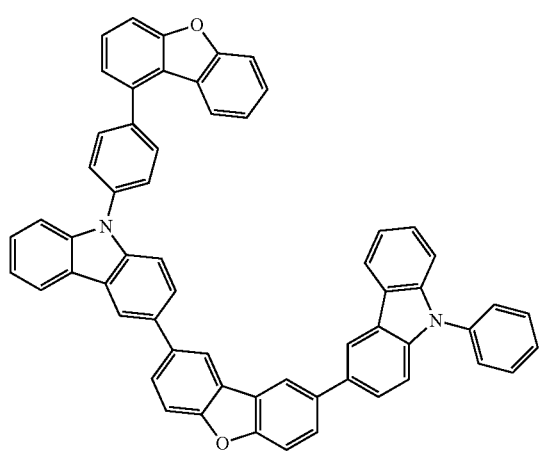
Formula 62
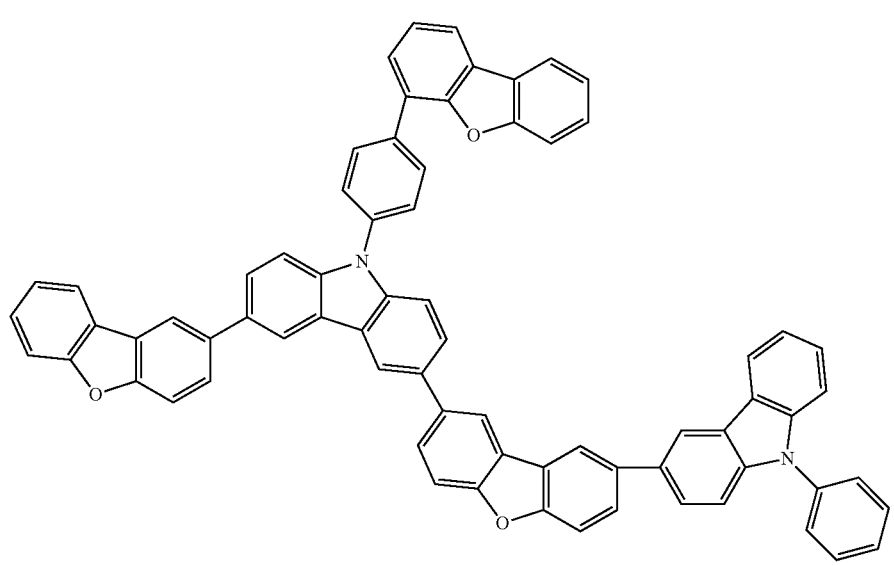

Formula 63
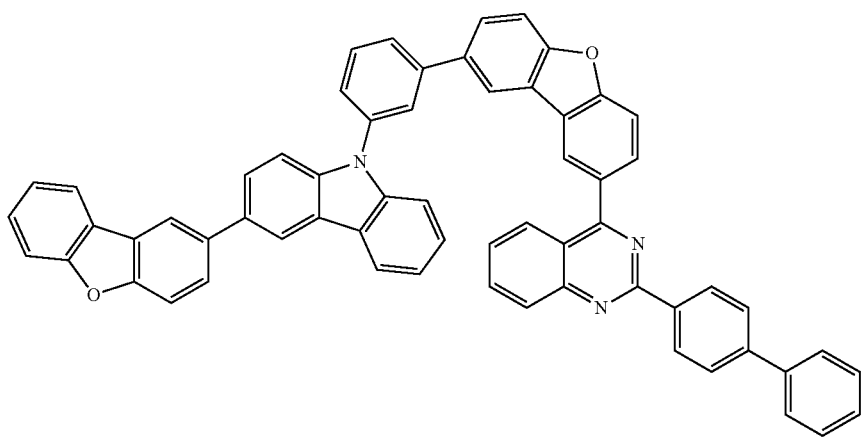
Formula 64
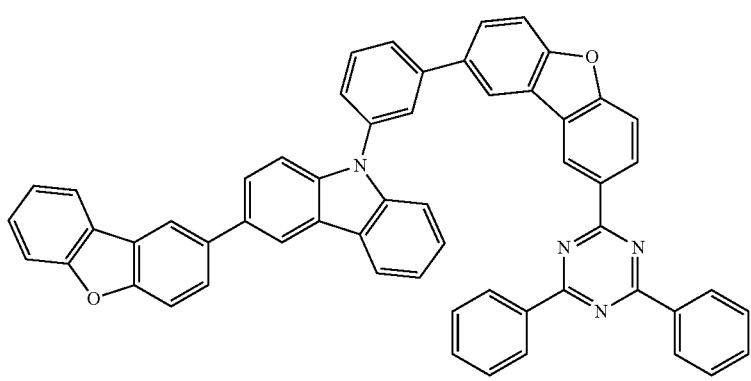
Formula 65
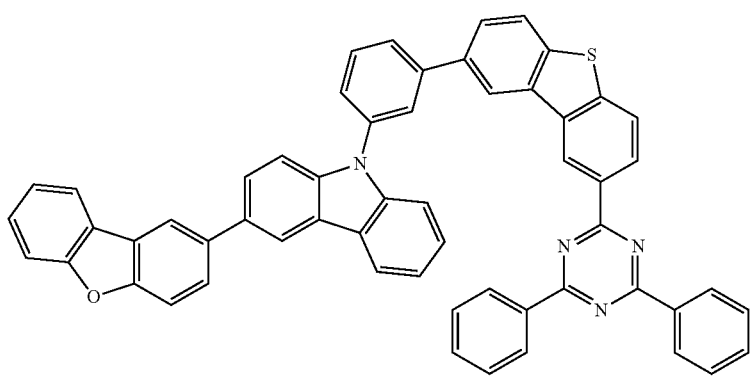

Formula 66
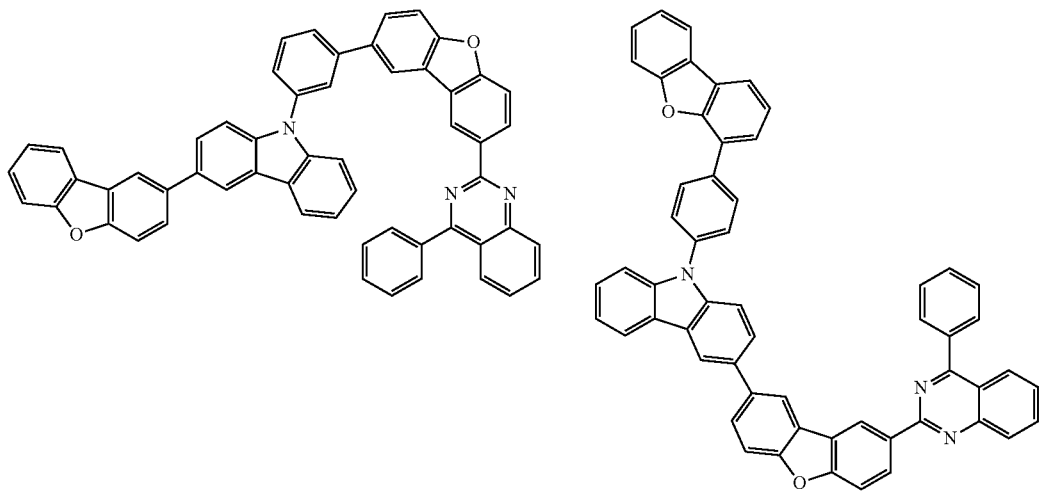
Formula 67
Formula 68
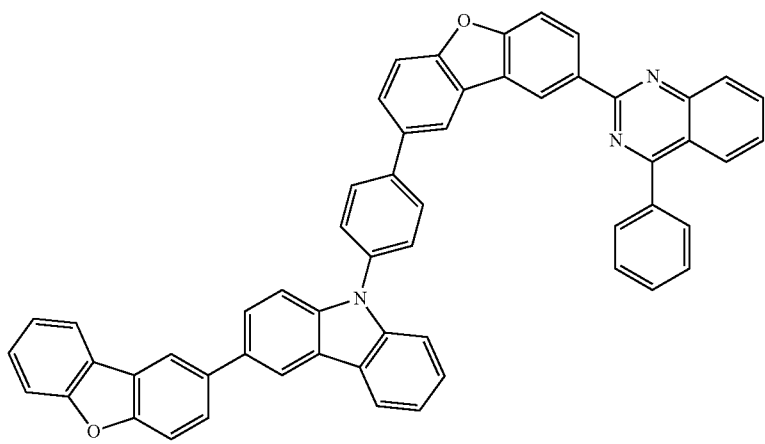
Formula 69
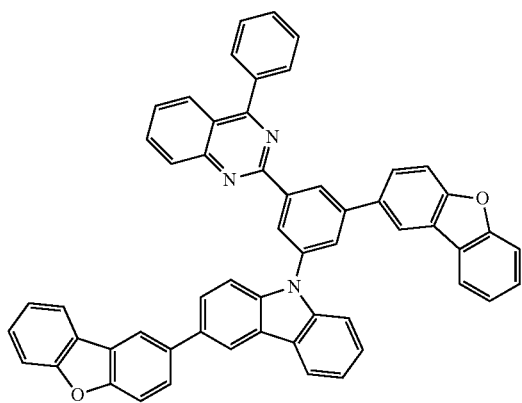

-continued
Formula 70
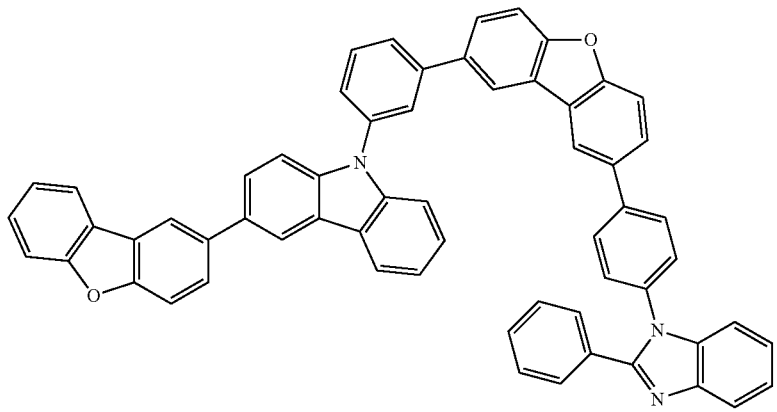
Formula 71
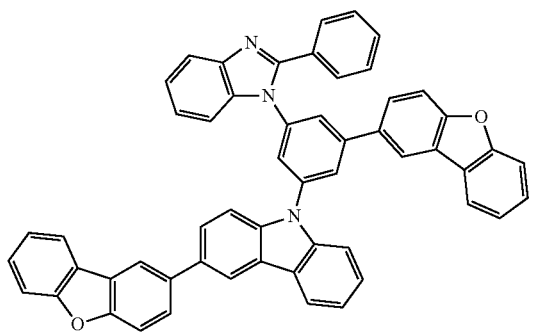
Formula 72
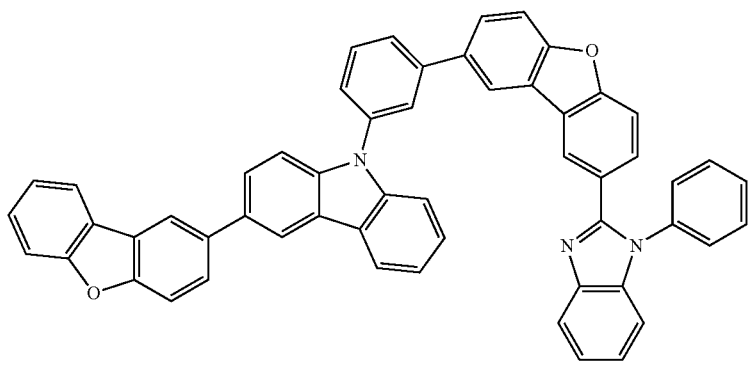
Formula 73
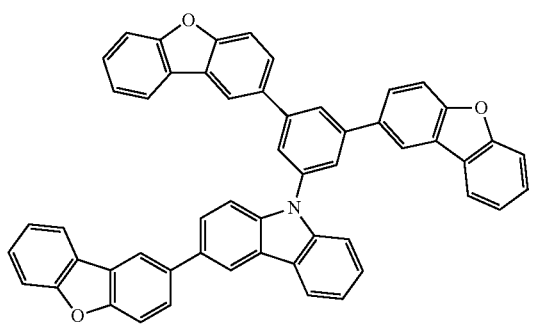
Formula 74
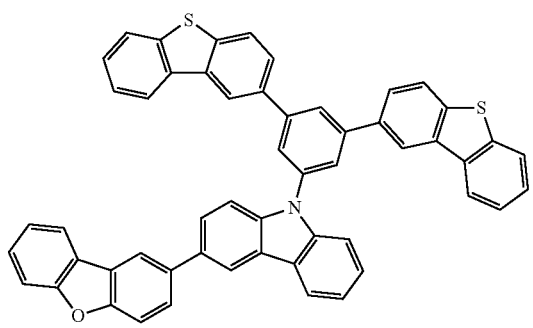

-continued
Formula 75
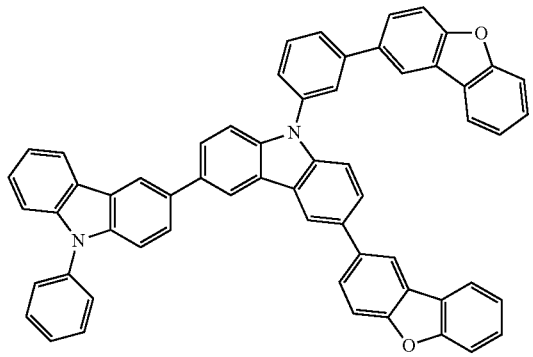
Formula 76
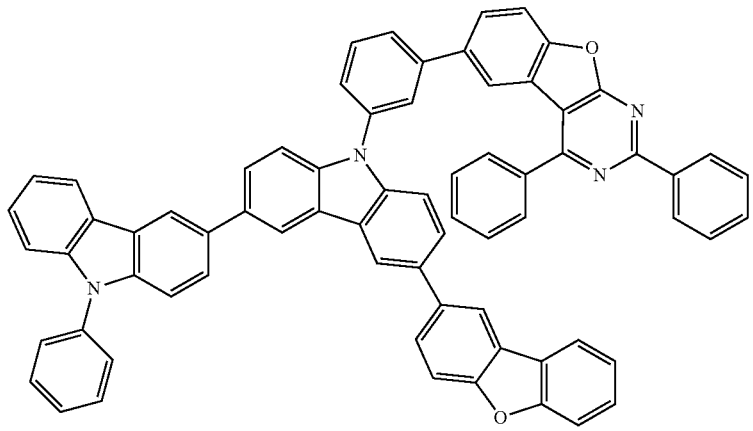
Formula 77
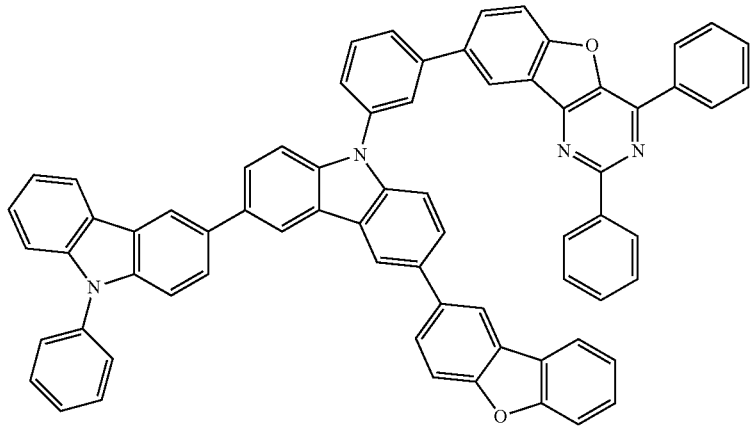
Formula 78 Formula 79
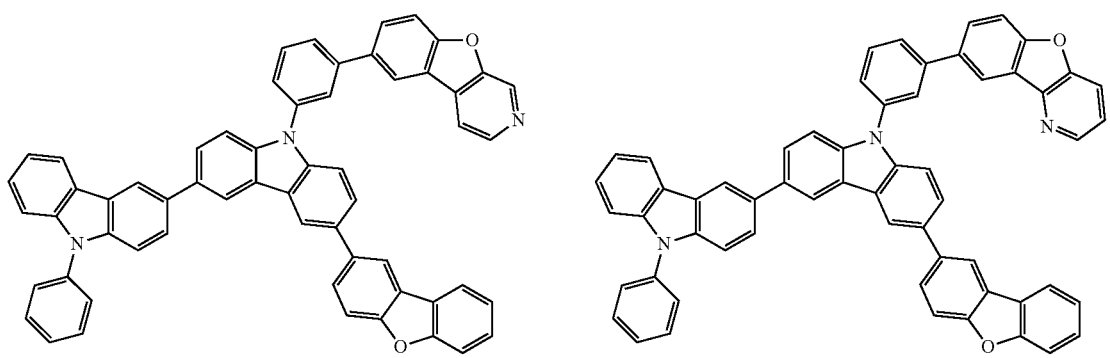

Formula 80
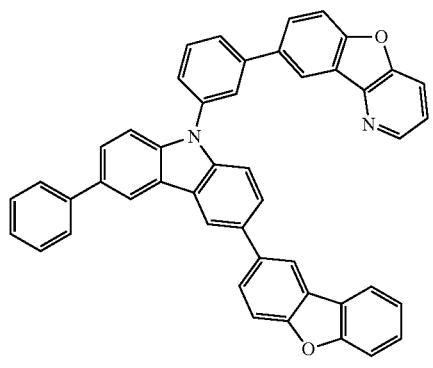
Formula 81
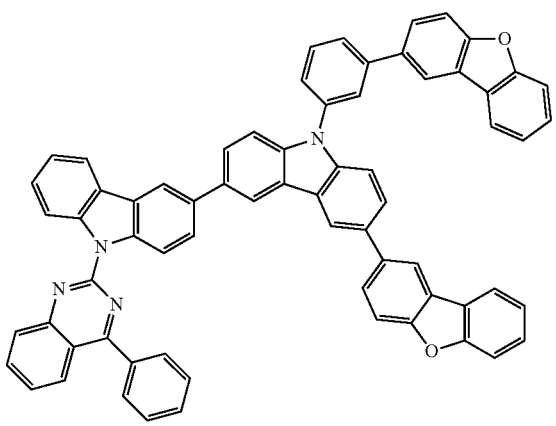
Formula 82
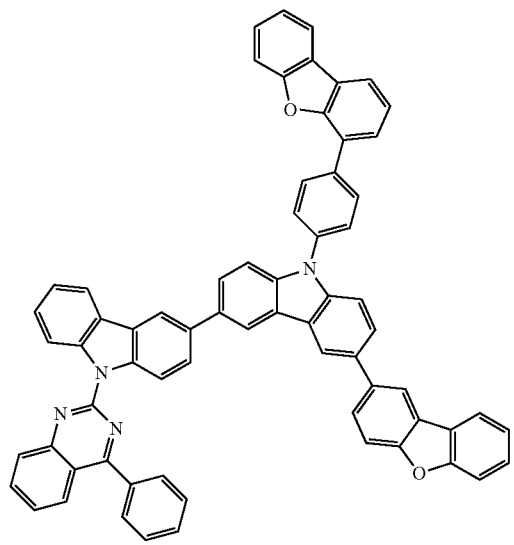
Formula 83
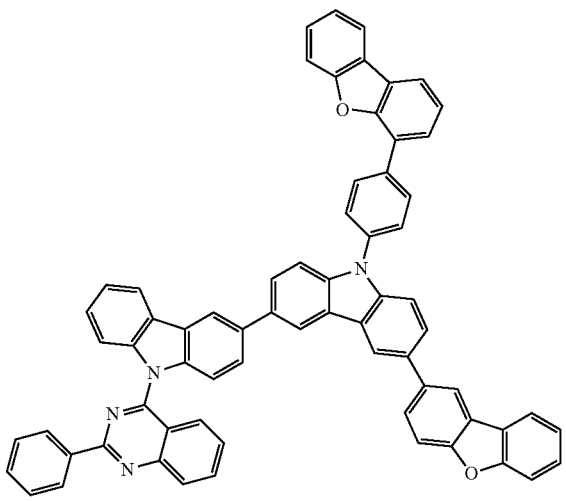
Formula 84
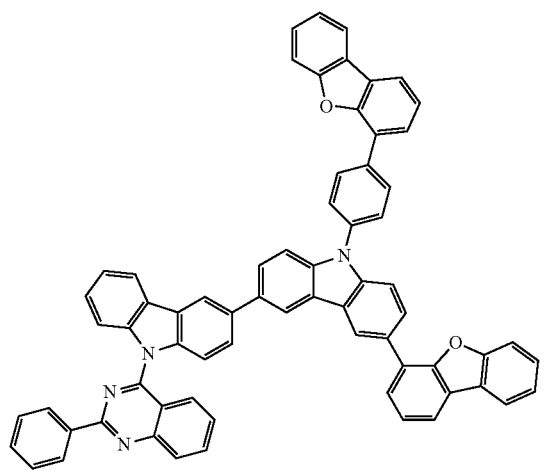
Formula 85
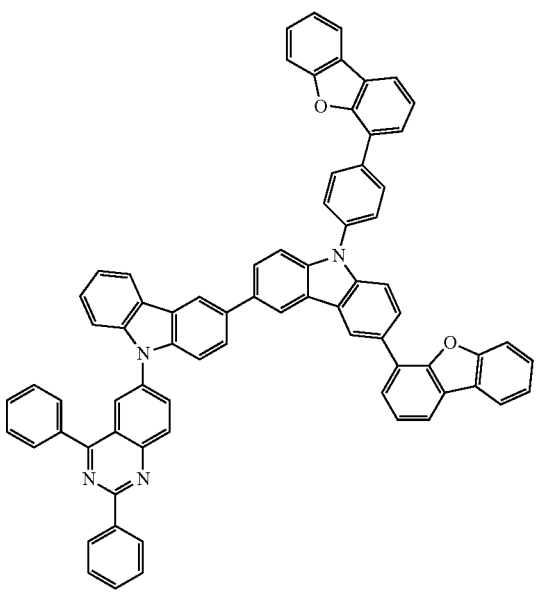

-continued
Formula 86
Formula 87
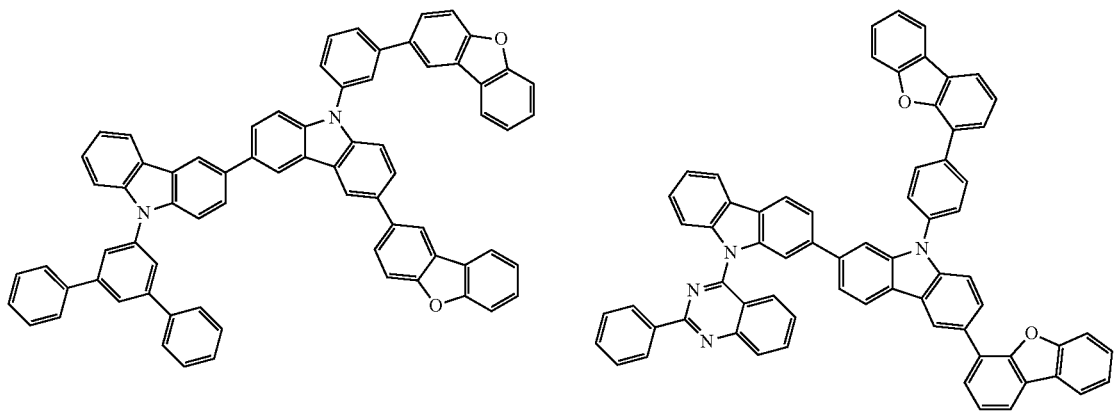
Formula 88
Formula 89
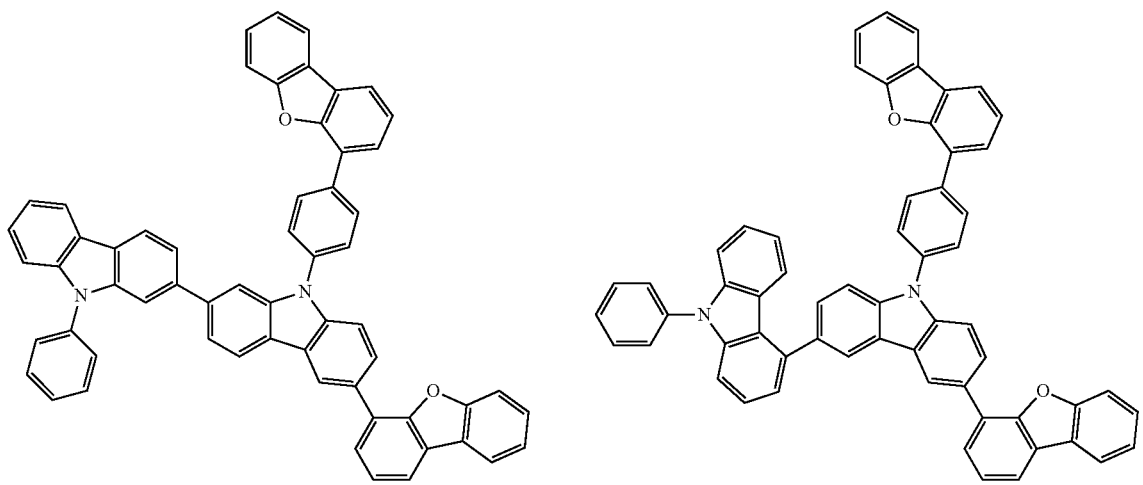
Formula 90
Formula 91
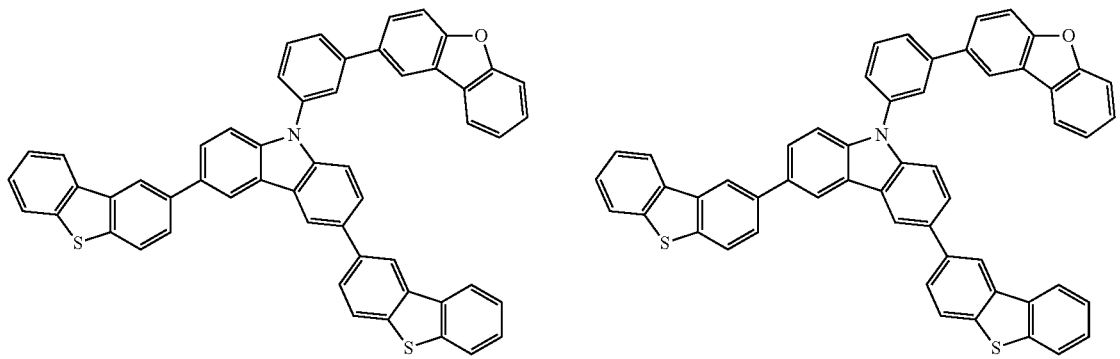

-continued
Formula 92
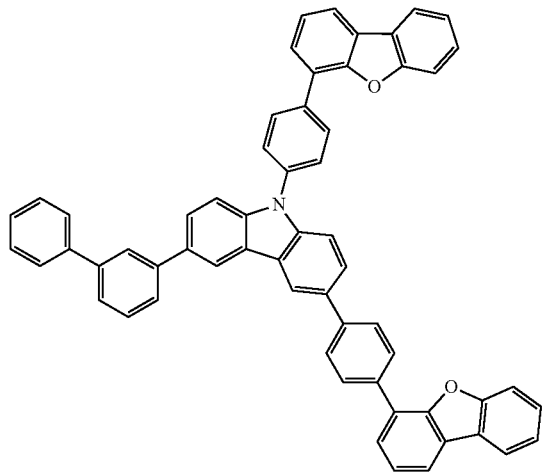
Formula 93
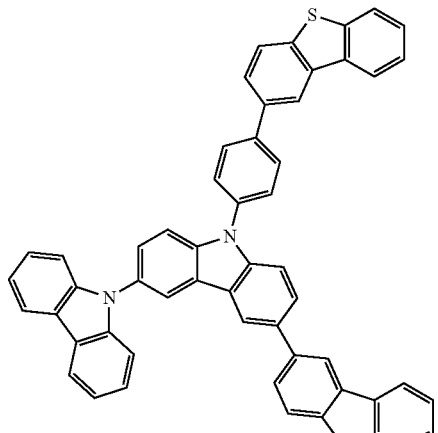
Formula 94
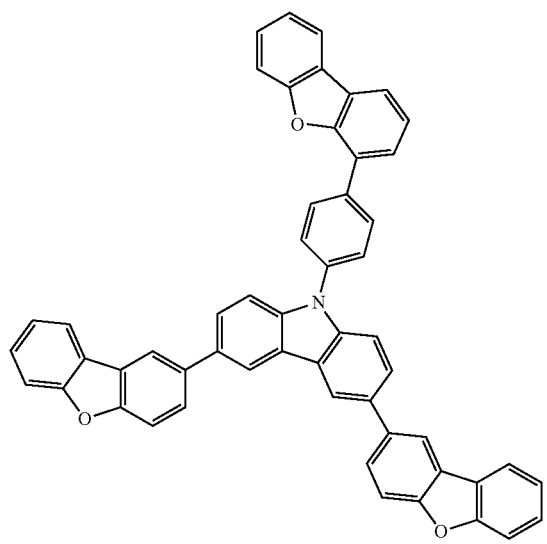
Formula 95
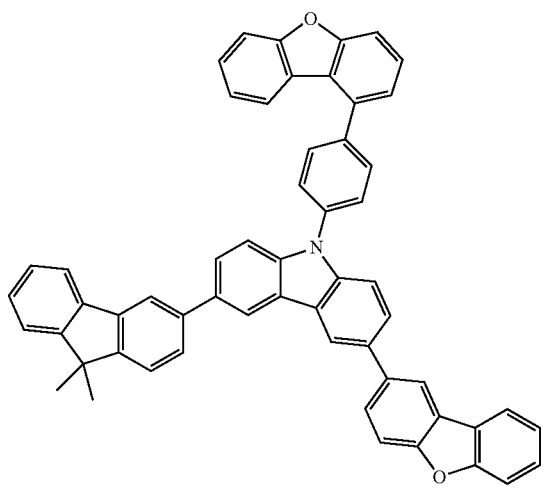
Formula 96
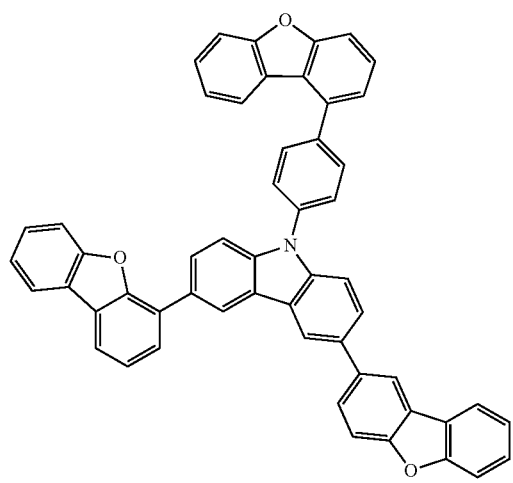
Formula 97
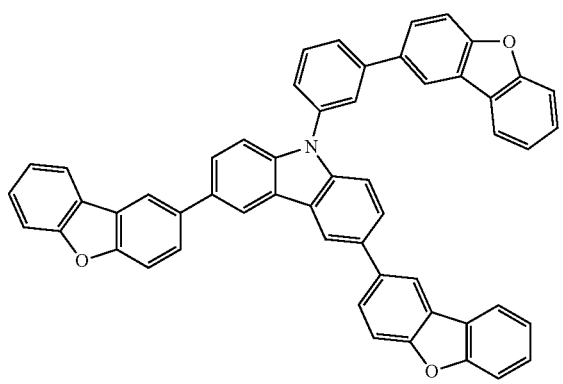

-continued
Formula 98
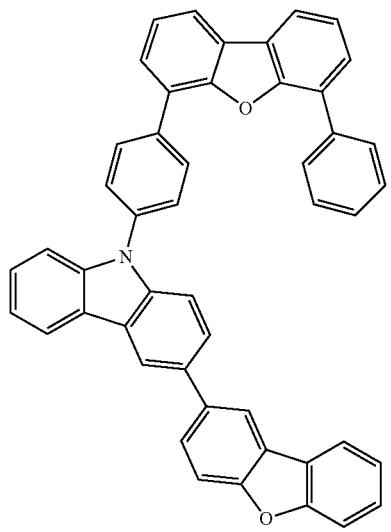
Formula 99
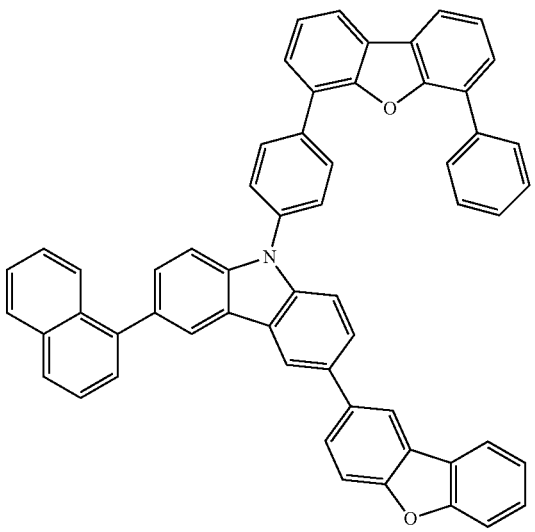
Formula 100
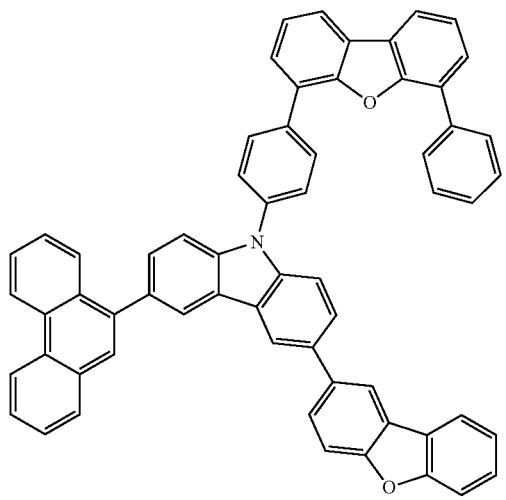
Formula 101
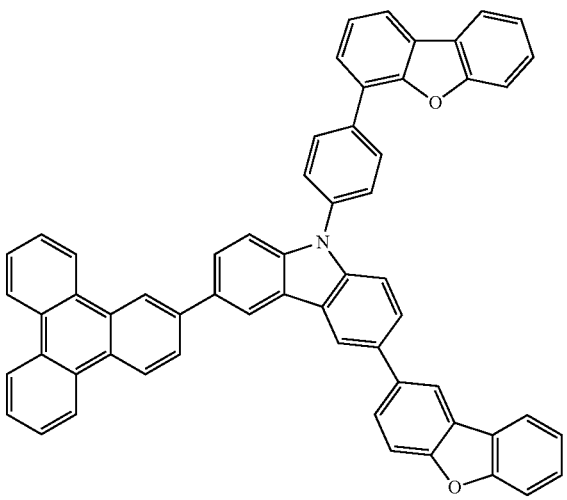
Formula 102
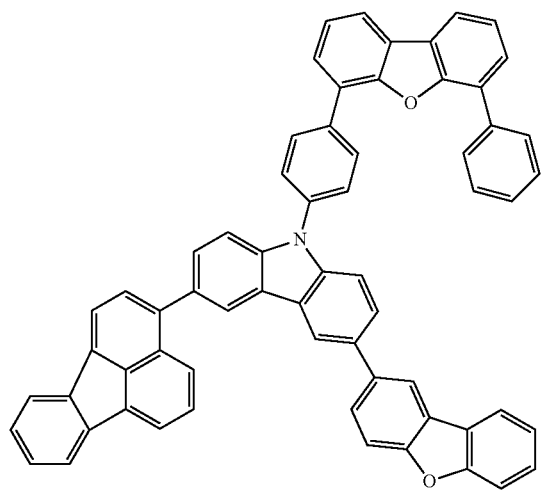
Formula 103
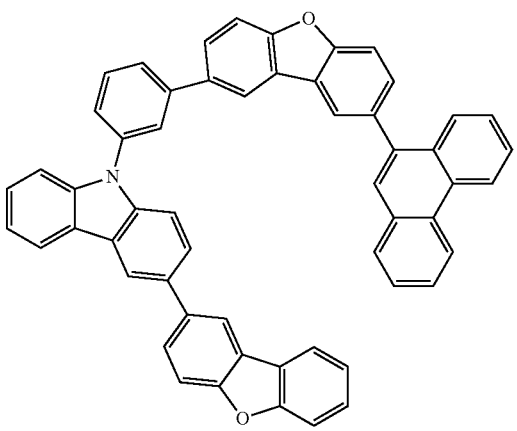

-continued
Formula 104
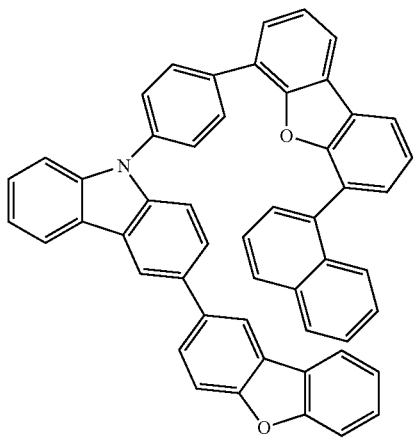
Formula 105
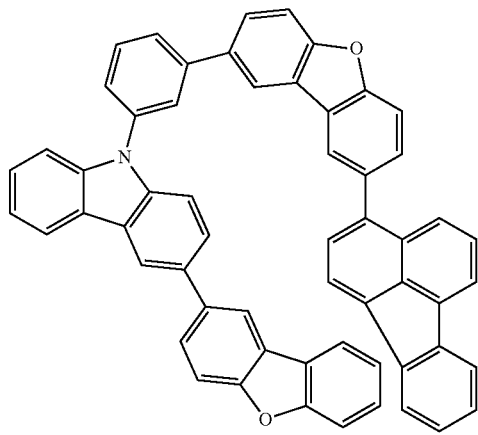
Formula 106
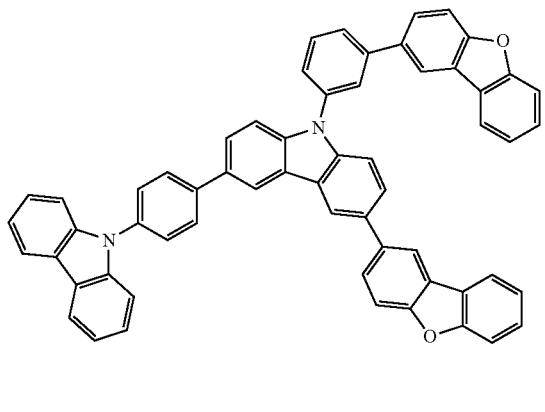
Formula 107
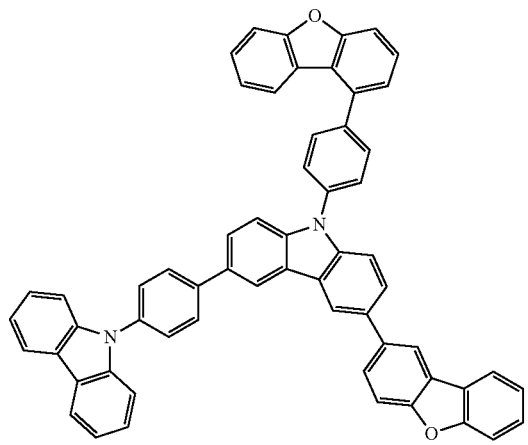
Formula 108
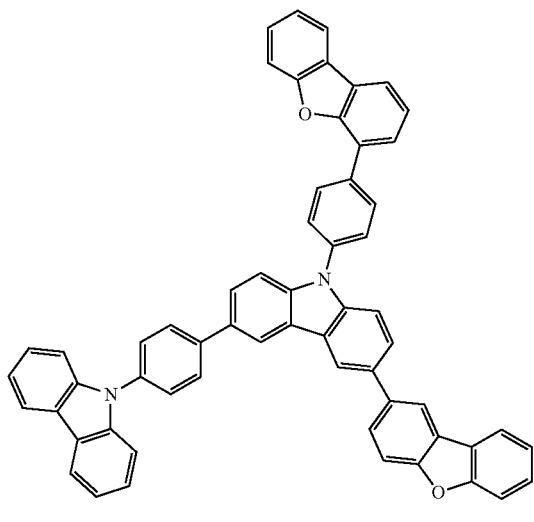
Formula 10*
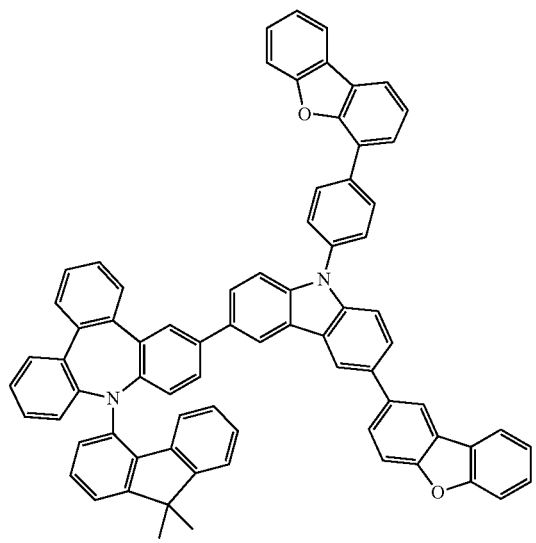

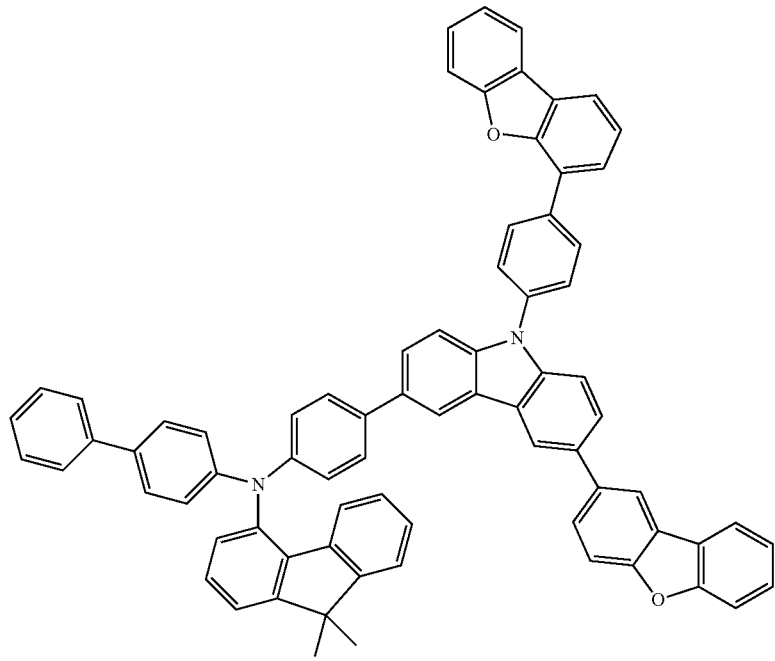
Formula 110
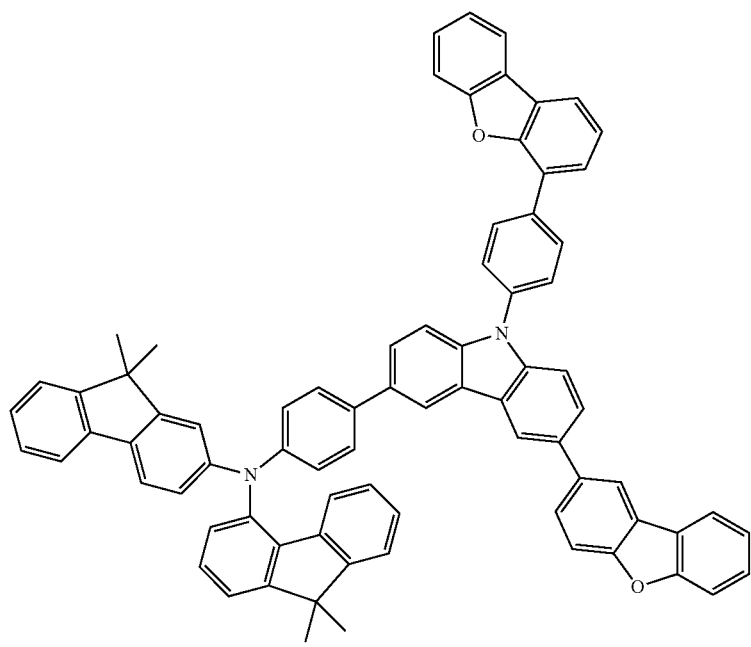
Formula 111

Formula 112
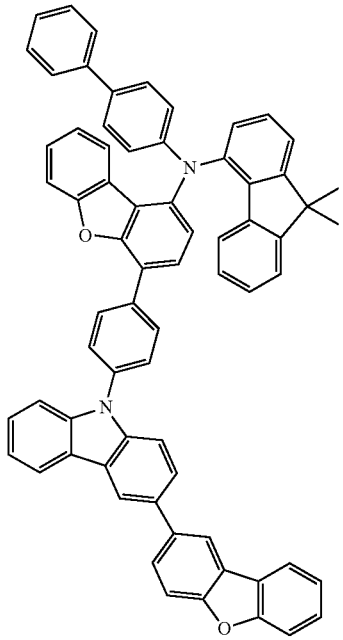
Formula 113
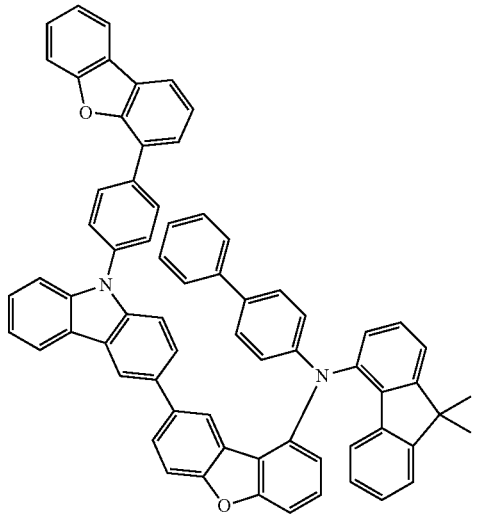
Formula 114
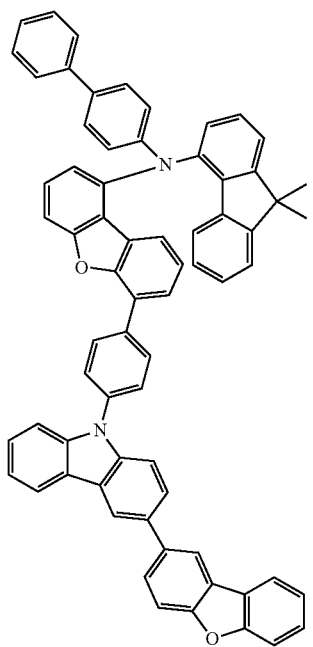
Formula 115
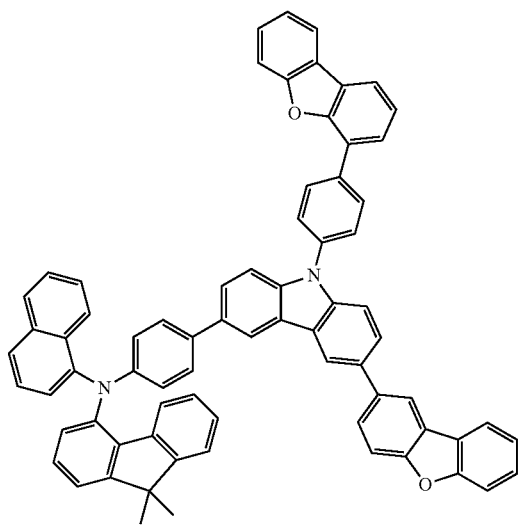

-continued
Formula 116
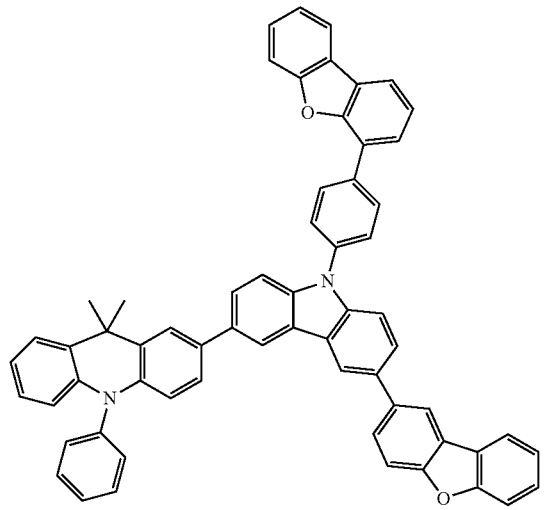
Formula 117
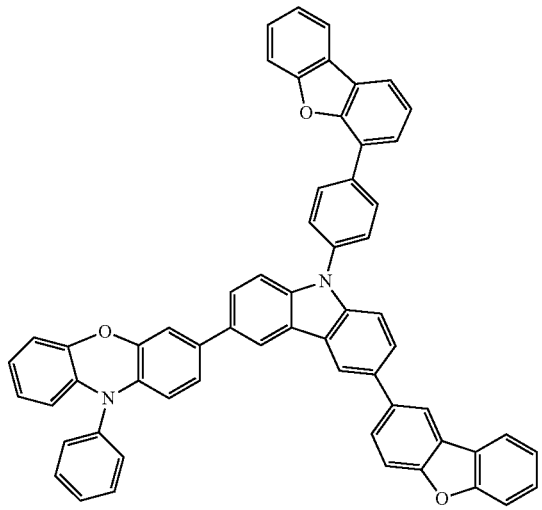
Formula 118
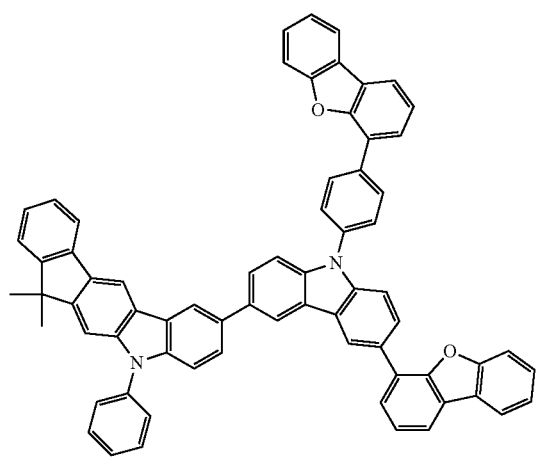
Formula 119
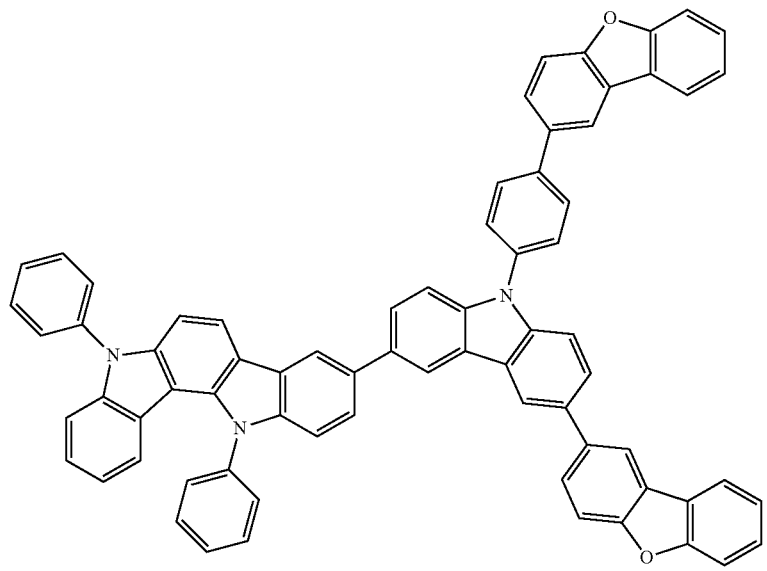
Formula 120

-continued
Formula 121
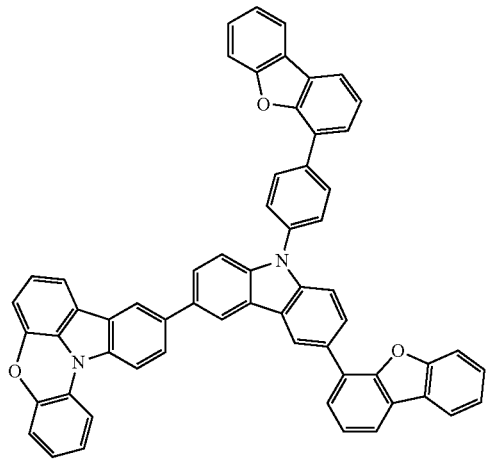
Formula 122
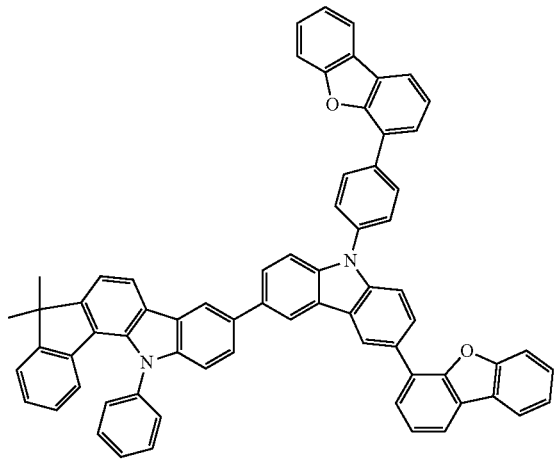
Formula 123
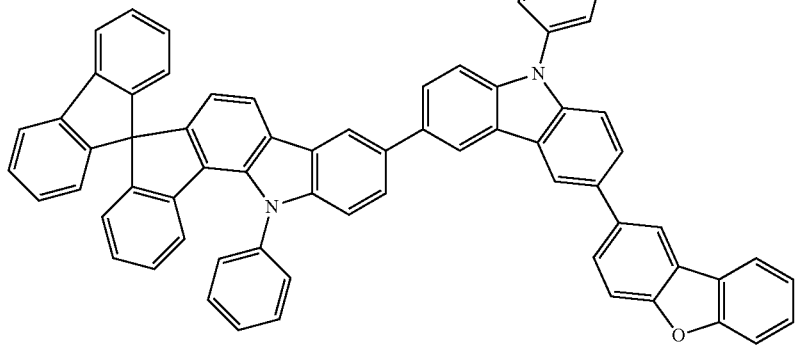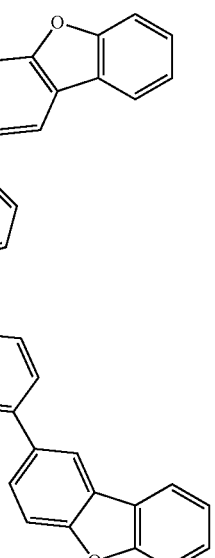
Formula 124
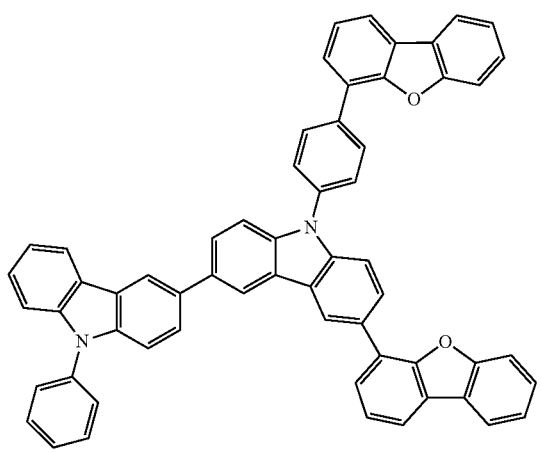
Formula 125
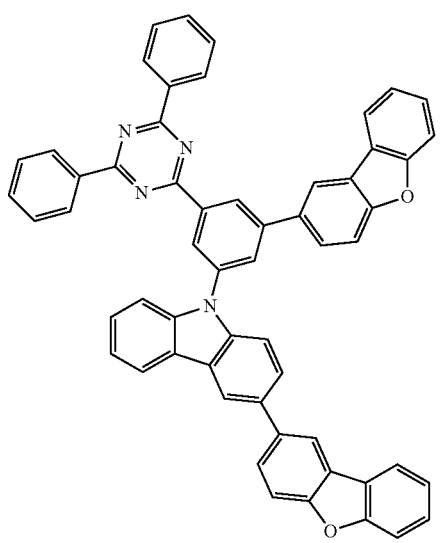

-continued
Formula 126
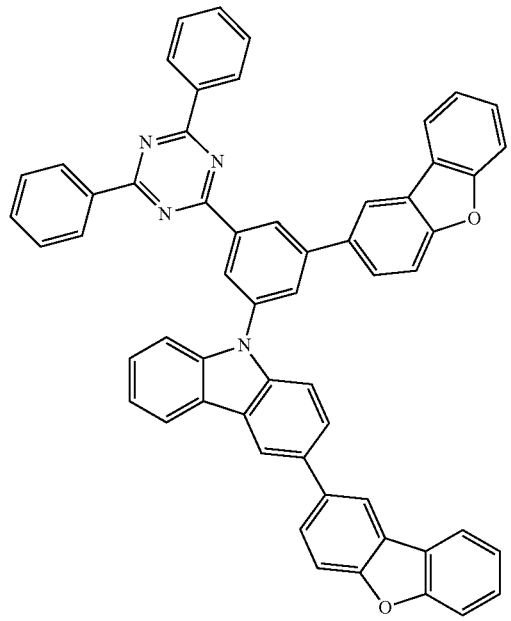
Formula 127
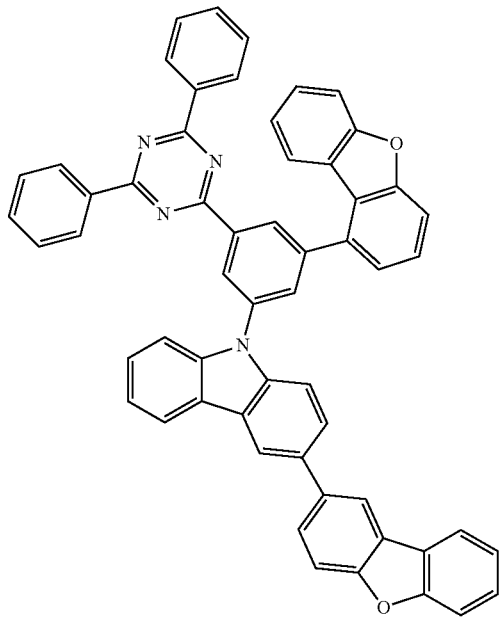
Formula 128
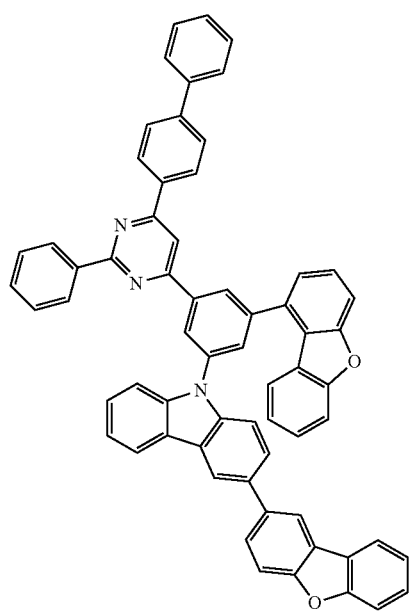
Formula 129
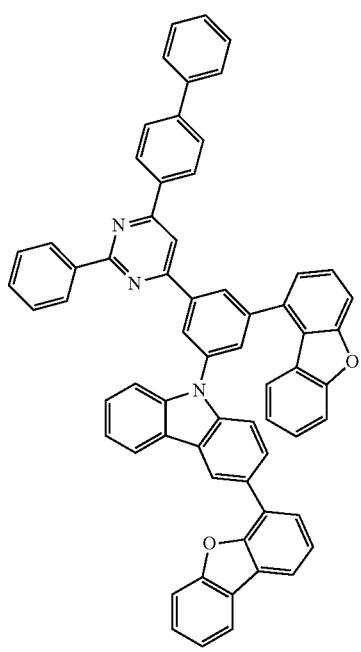

Formula 130
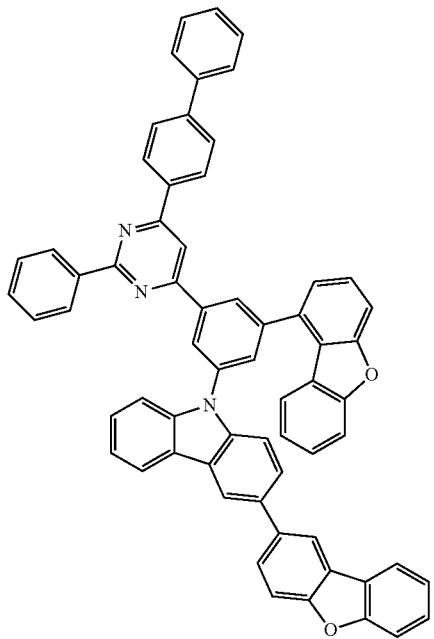
Formula 131
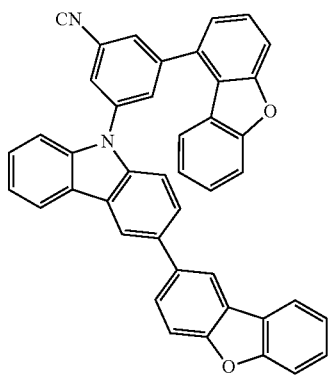
Formula 132
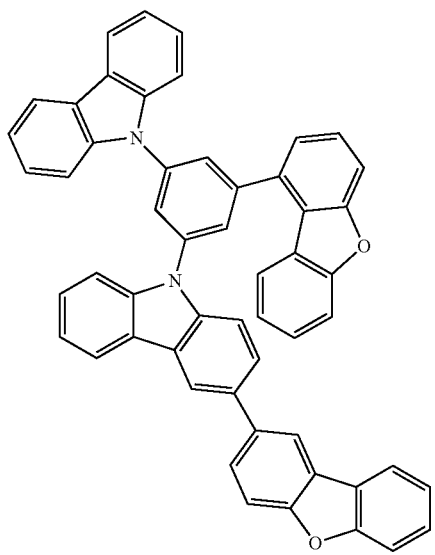
Formula 133
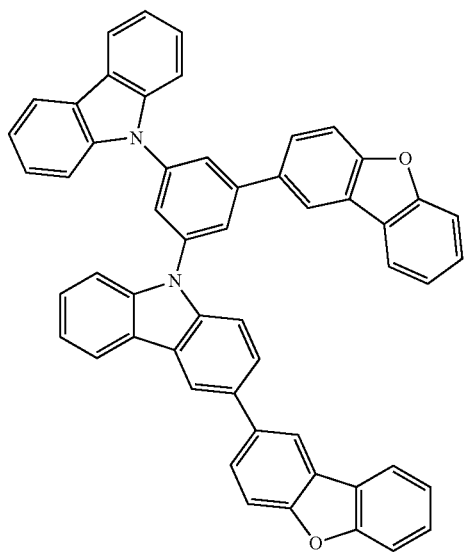

-continued
Formula 134
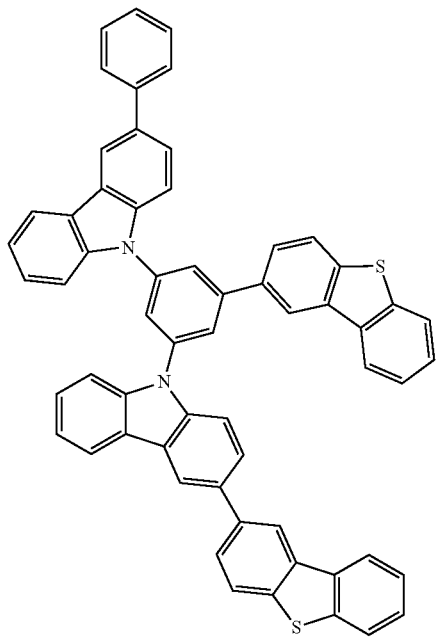
Formula 135
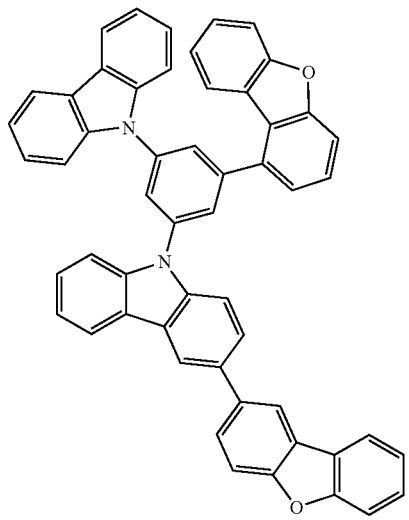
Formula 136
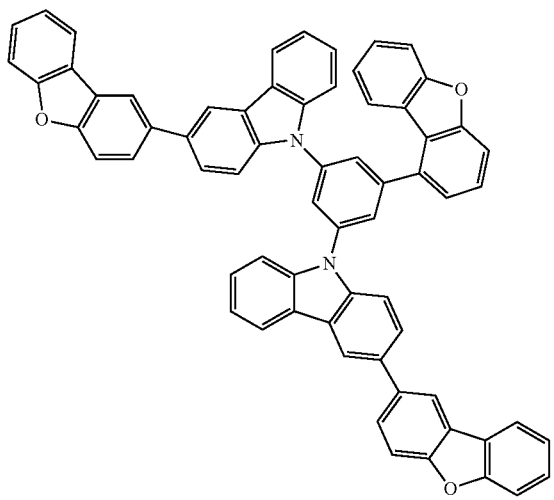
Formula 137
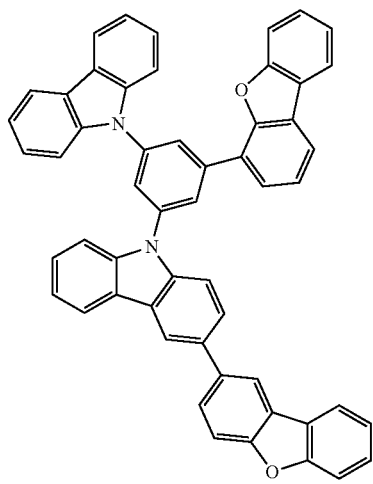
Formula 138
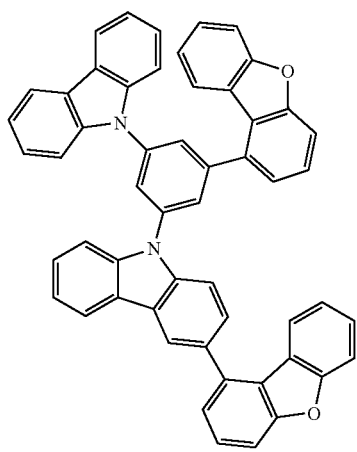
Formula 139
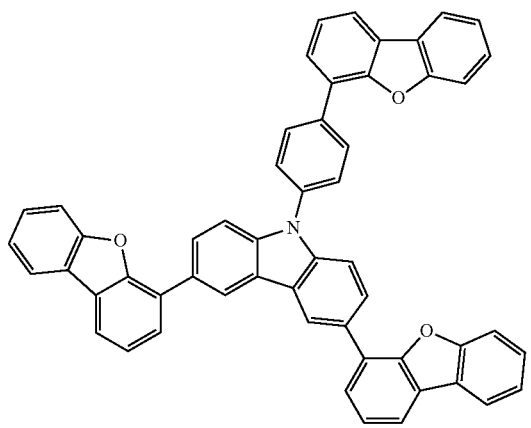

-continued
Formula 140
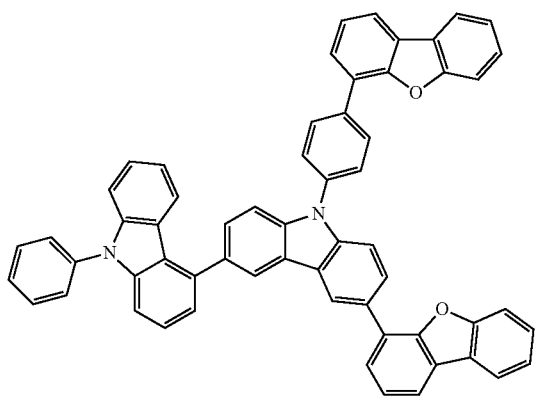
Formula 141
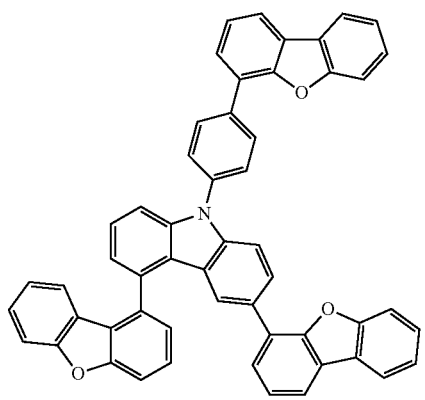
Formula 142
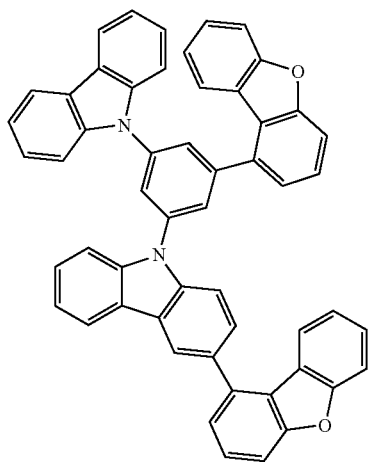
Formula 143
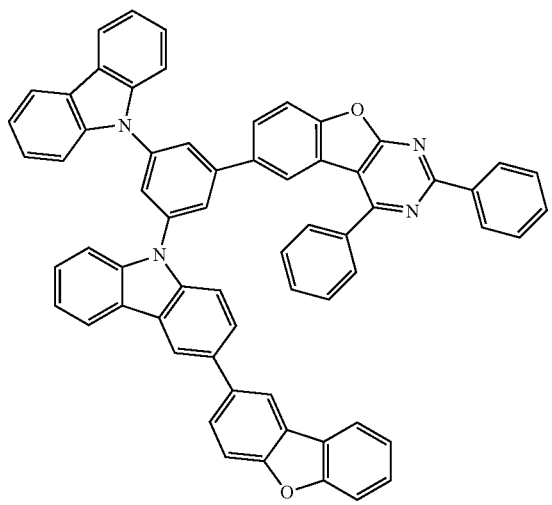
Formula 144
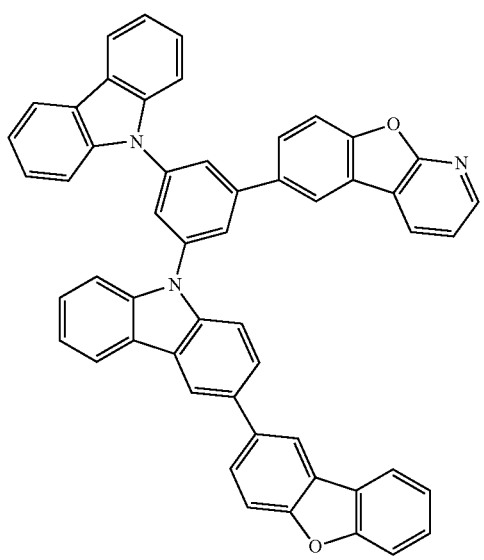
Formula 145
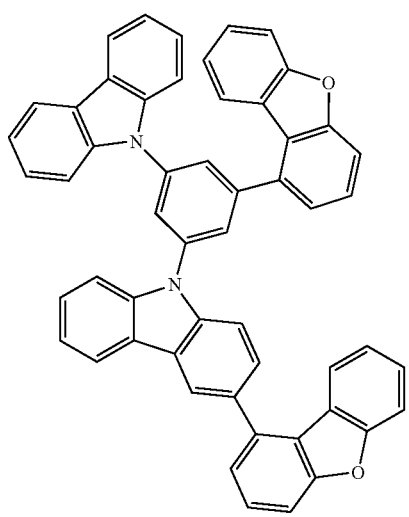

Formula 146
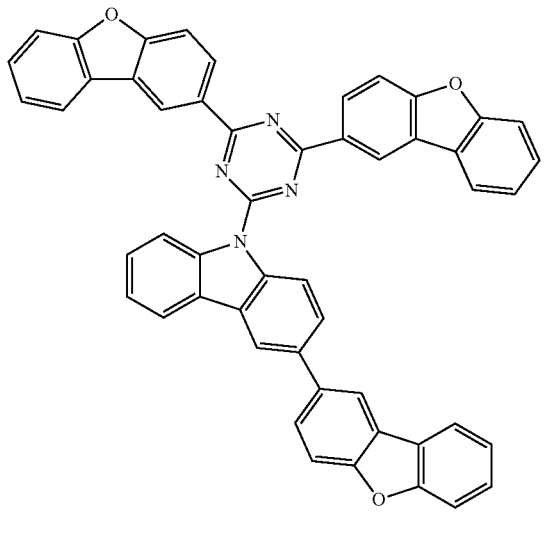
Formula 147
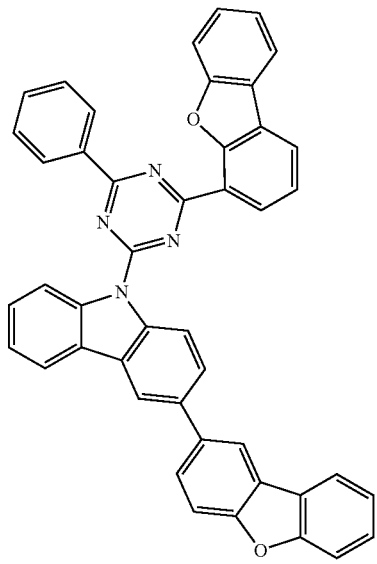
Formula 148
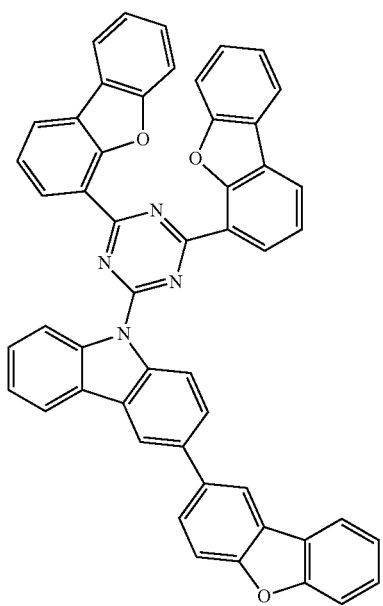
Formula 149
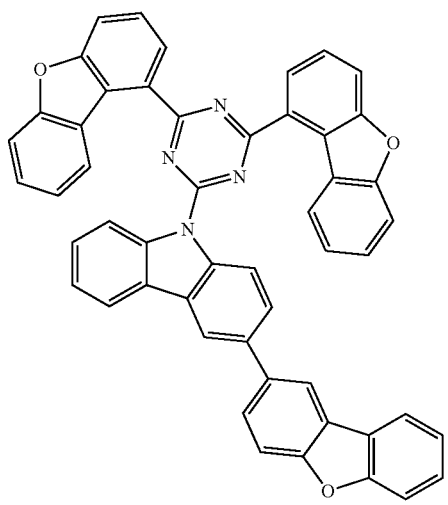

-continued
Formula 150
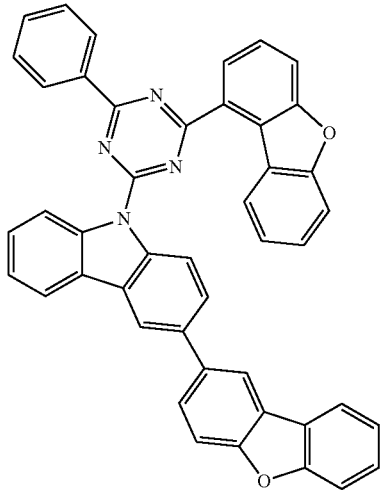
Formula 151
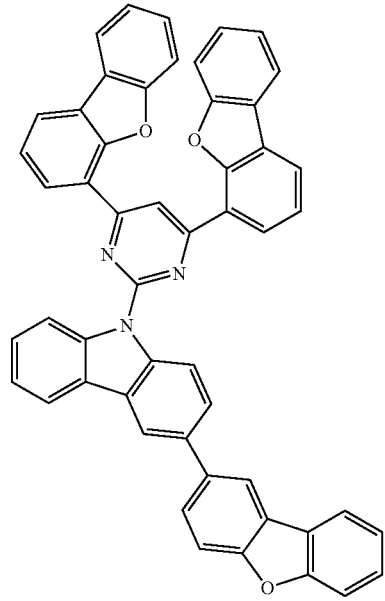
Formula 152
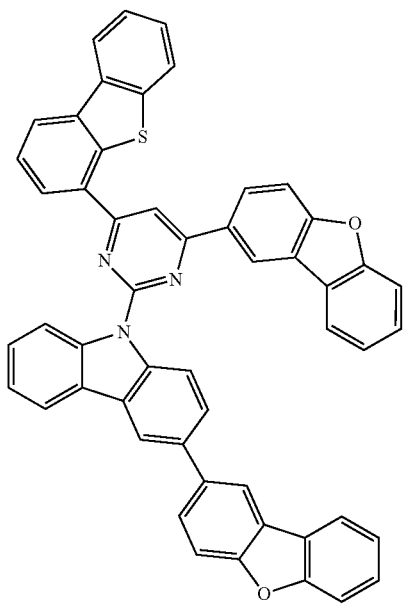
Formula 153
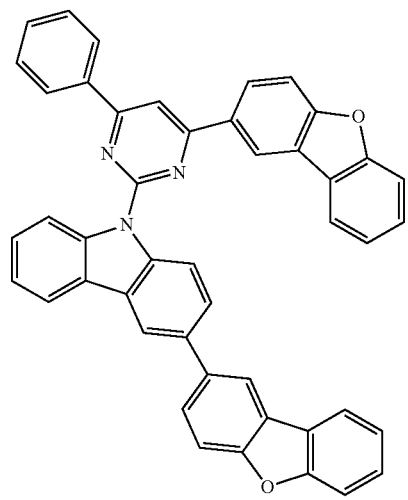

Formula 154
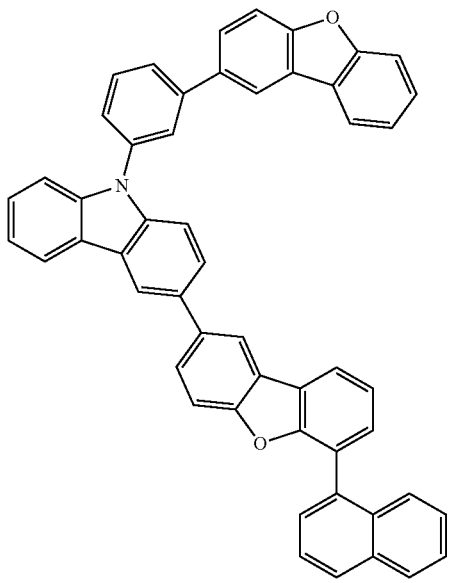
Formula 155
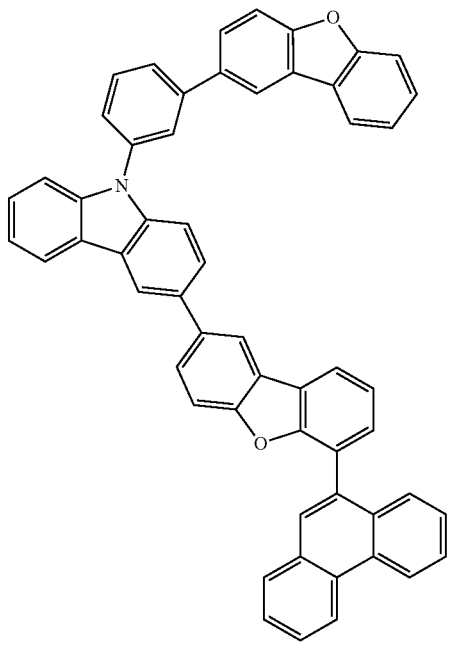
Formula 156
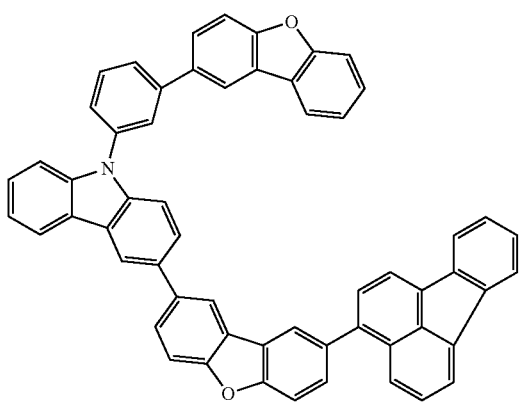
Formula 157
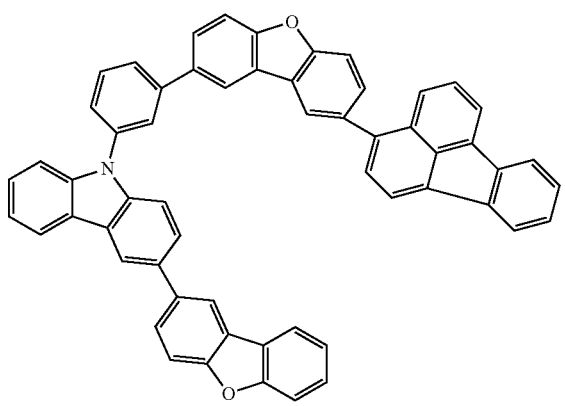
Formula 158
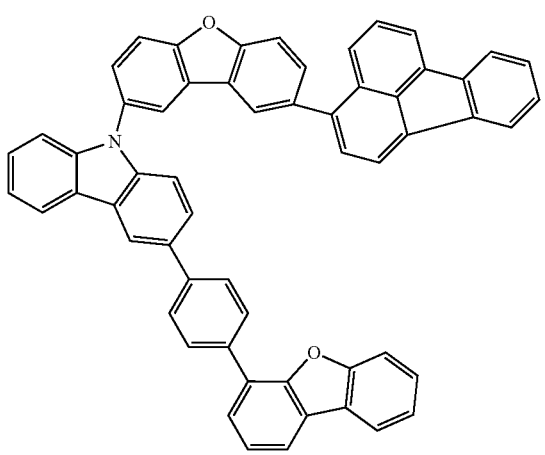
Formula 159
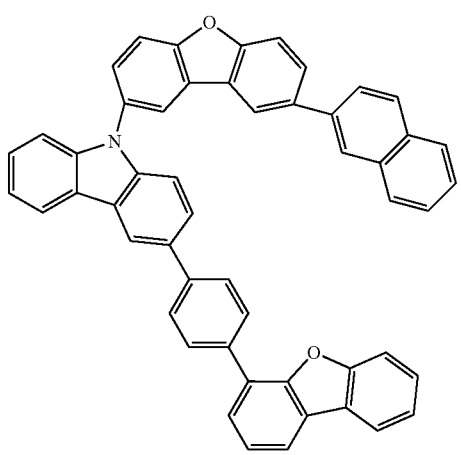

-continued

Formula 160
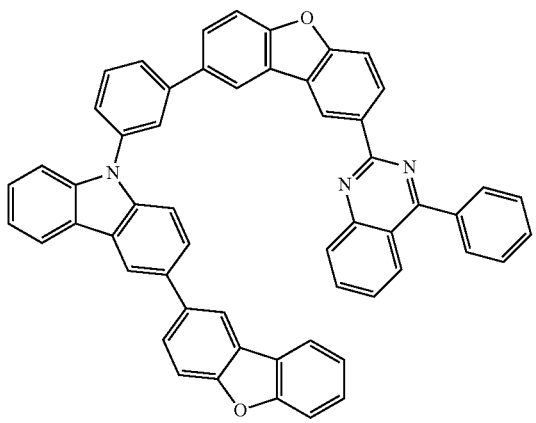

Formula 161
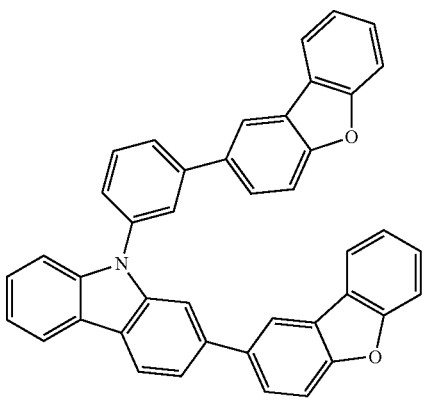

Formula 162
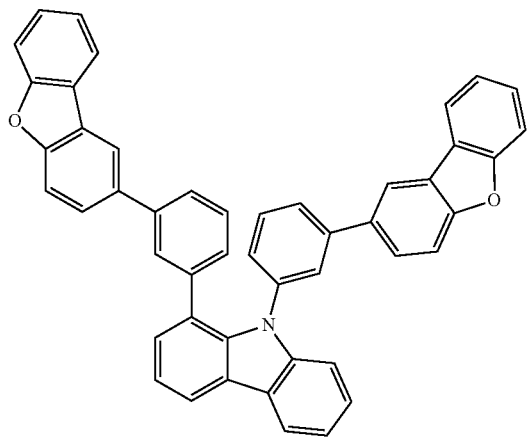

Formula 162
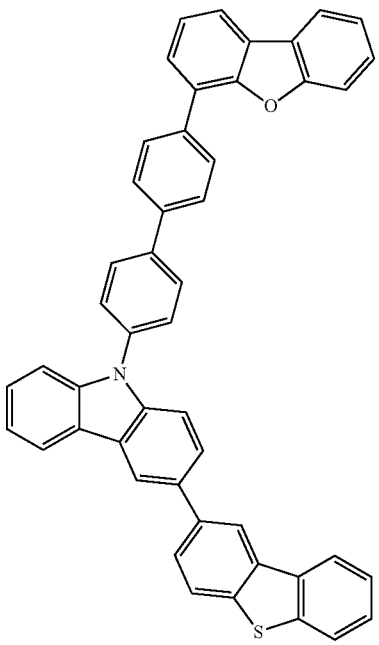

Preferred embodiments of compounds of the invention are detailed specifically in the examples, these compounds being usable alone or in combination with further compounds for all purposes of the invention.

Provided that the conditions specified in Claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing compounds comprising structures of formula (I), which is characterized in that, in a coupling reaction, a group comprising at least one carbazole radical is joined to a group comprising at least one benzofuran and/or one benzothiophene radical.

Particularly suitable and preferred coupling reactions which all lead to C—C bond formation and/or C—N bond formation are those according to BUCHWALD, ULLMANN, SUZUKI, YAMAMOTO, STILLE, HECK, NEGISHI, SONOGASHIRA and HIYAMA. These reactions are widely known, and the examples will provide the person skilled in the art with further pointers.

In the synthesis scheme which follows, the compounds are shown with a small number of substituents to simplify the structures. This does not rule out the presence of any desired further substituents in the processes.

An illustrative implementation is given by the scheme which follows, without any intention that this should impose a restriction. The component steps of the scheme may be combined with one another as desired.

For example, according to the following scheme, proceeding from a reactive carbazole compound, for example by a Suzuki reaction with a reactive dibenzofuran or dibenzothiophene compound, it is possible to obtain a carbazole compound having a dibenzofuran or dibenzothiophene substituent which, in a further step, for example a Buchwald and/or Ullmann reaction, is converted to a compound according to the present invention.

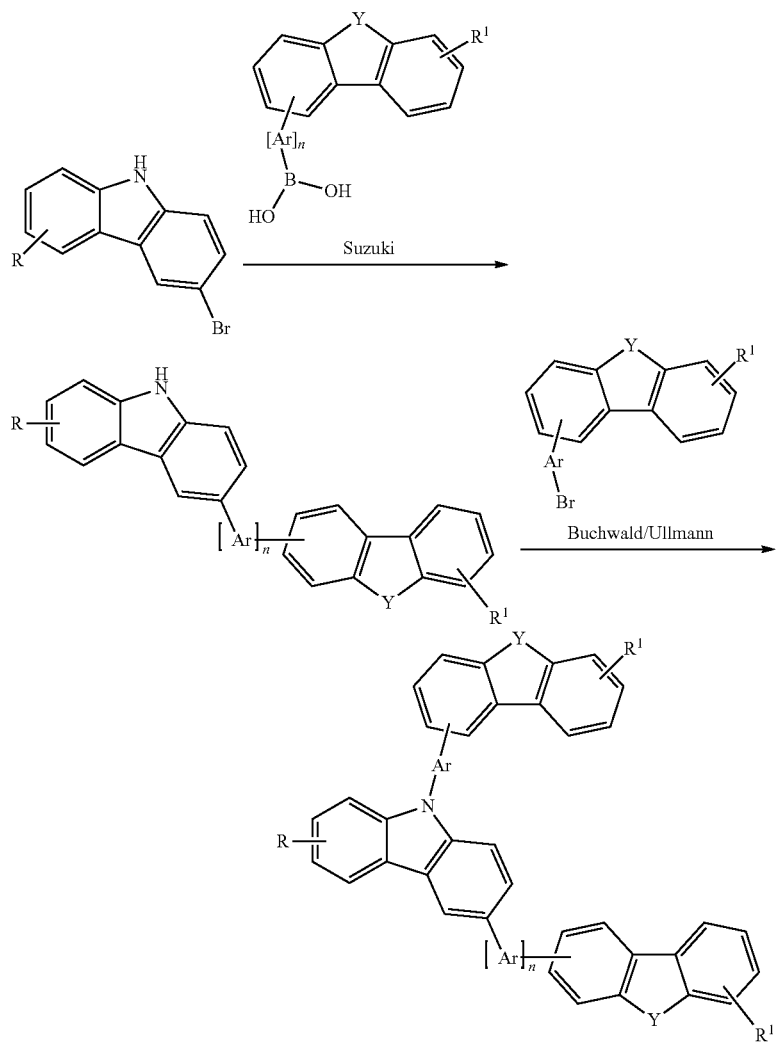

The processes shown for synthesis of the compound of the invention should be understood by way of example. The person skilled in the art will be able to develop alternative synthesis routes within the scope of his common knowledge in the art.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of the formula (I) or the preferred embodiments detailed above and below in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in sufficient concentrations soluble, in order to be able to process the complexes from solution. These soluble compounds are of particularly good suitability for processing from solution, for example by printing methods. In addition, it should be emphasized that the compounds of the invention comprising at least one structure of the formula (I) already have enhanced solubility in these solvents.

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formula (I) or compounds of the invention, wherein one or more bonds of the compounds of the invention or of the structures of the formula (I) to the polymer, oligomer or dendrimer are present. According to the linkage of the structures of the formula (I) or of the compounds, these therefore form a side chain of the oligomer or polymer or are bonded within the main chain.

The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (I) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound comprising structures of formula (I) and having a molecular weight of preferably not more than 10 000 g/mol, more preferably not more than 5000 g/mol, especially preferably not more than 3000 g/mol, specifically preferably not more than 2000 g/mol and most preferably not more than 1000 g/mol.

In addition, it is a feature of preferred compounds that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formula (I) having a glass transition temperature of at least 70° C., more preferably of at least 110° C., even more preferably of at least 125° C. and especially preferably of at least 150° C., determined in accordance with DIN 51005.

The present invention still further provides a formulation comprising a compound of the invention or an oligomer, polymer or dendrimer of the invention and at least one further compound. The further compound may preferably be a solvent. The further compound may alternatively be a further organic or inorganic compound which is likewise used in the electronic device, for example a matrix material. This further compound may also be polymeric.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention still further provides a composition comprising a compound of the invention and at least one further organic functional material. Functional materials are generally the organic or inorganic materials introduced between the anode and cathode. Preferably, the organic functional material is selected from the group consisting of fluorescent emitters, phosphorescent emitters, host materials, matrix materials, electron transport materials, electron injection materials, hole conductor materials, hole injection materials, n-dopants, wide band gap materials, electron blocker materials and hole blocker materials.

The present invention therefore also relates to a composition comprising at least one compound comprising structures of formula (I) or the preferred embodiments detailed above and below and at least one further matrix material. According to a particular aspect of the present invention, the further matrix material has hole-transporting properties.

The present invention further provides a composition comprising at least one compound comprising at least one structure of formula (I) and at least one wide band gap material, a wide band gap material being understood to mean a material in the sense of the disclosure of U.S. Pat. No. 7,294,849. These systems exhibit particularly advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM 1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO (eV)=((HE$h$*27.212)−0.9899)/1.1206

LUMO (eV)=((LE$h$*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09 W" (Gaussian Inc.) and Q-Chem 4.1 (Q-Chem, Inc.).

The present invention also relates to a composition comprising at least one compound comprising structures of formula (I) and at least one phosphorescent emitter, the term "phosphorescent emitter" also being understood to mean phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices.

Explicit examples of phosphorescent dopants are adduced in the following table:

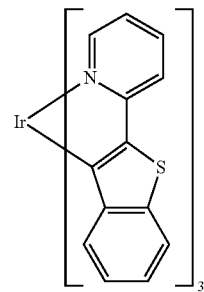

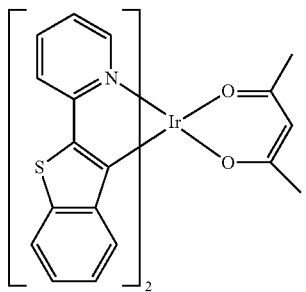

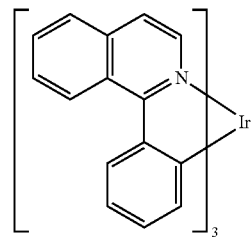

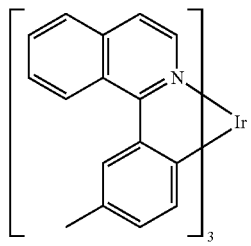

-continued
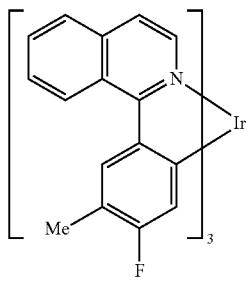 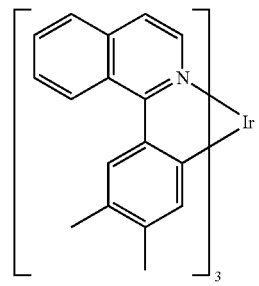
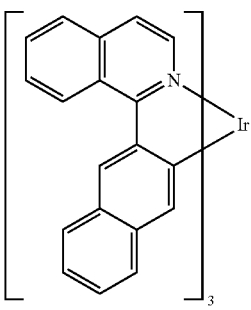 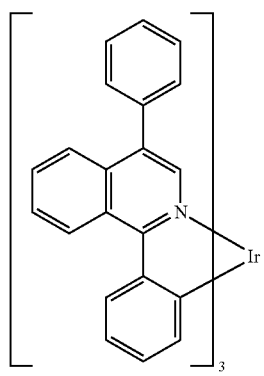
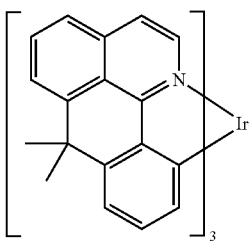 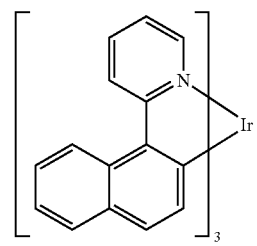
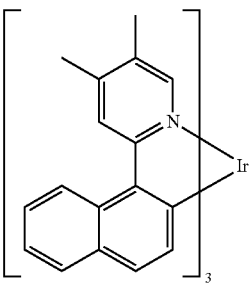 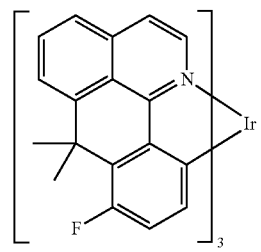
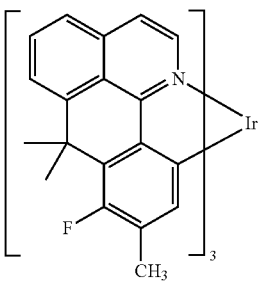 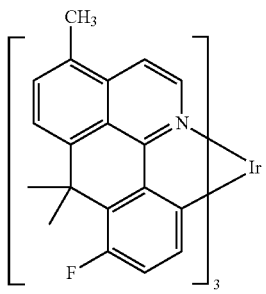

-continued
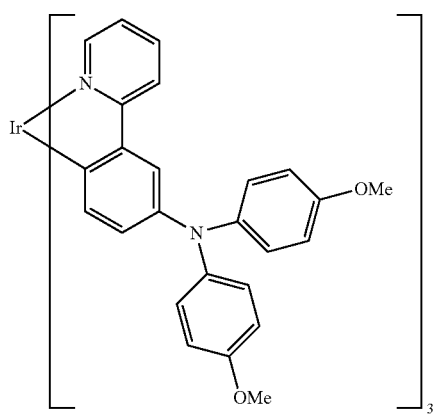
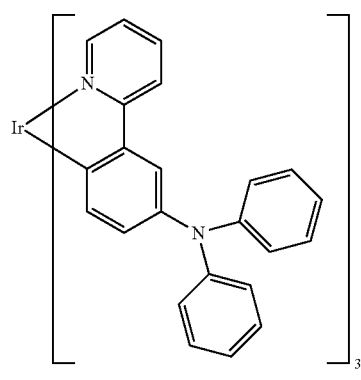
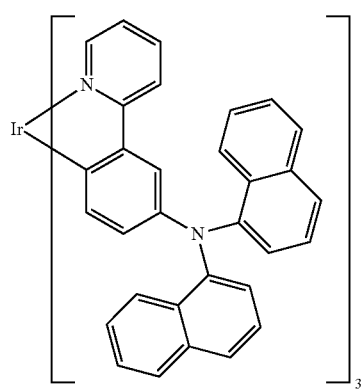
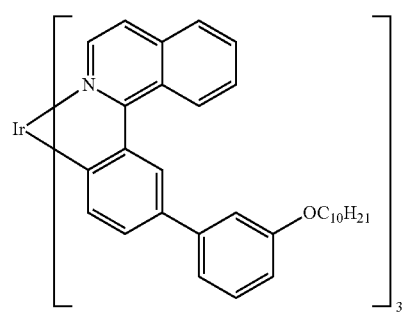
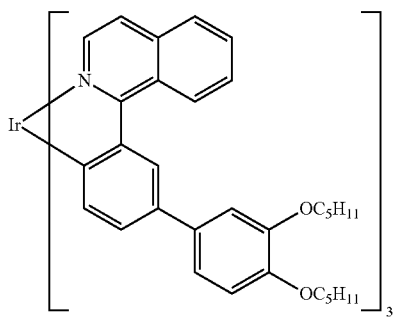
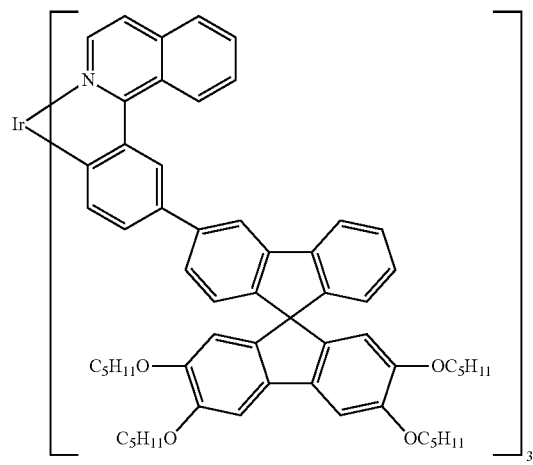
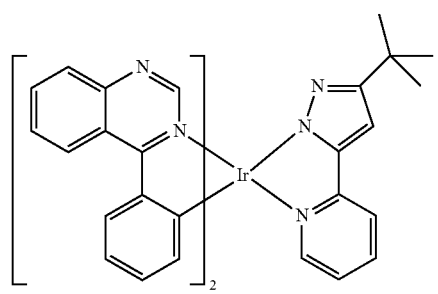
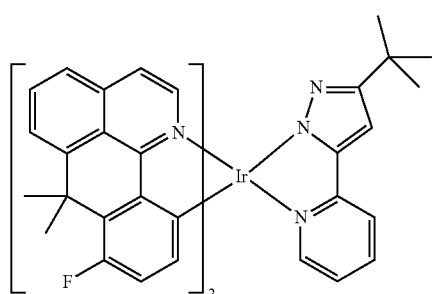

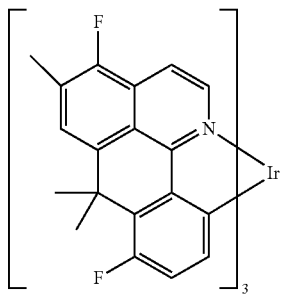
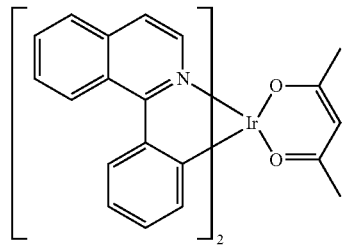
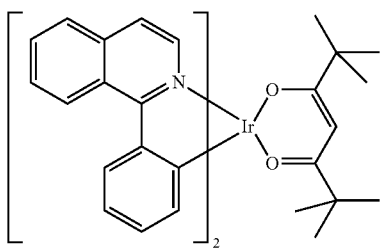
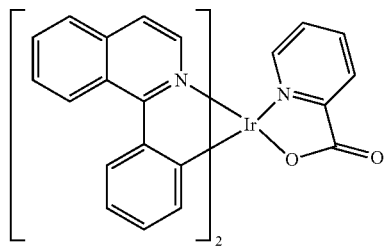
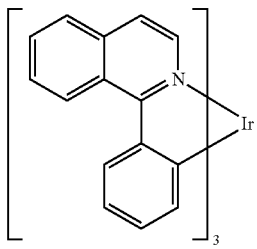
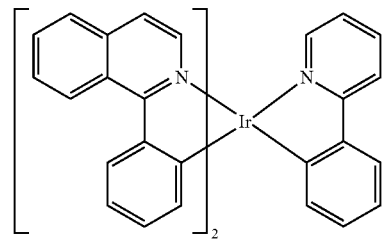
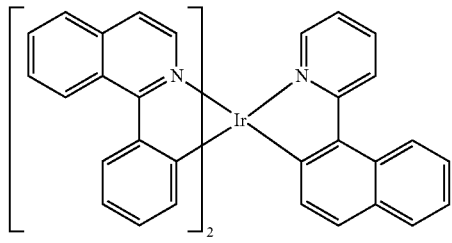
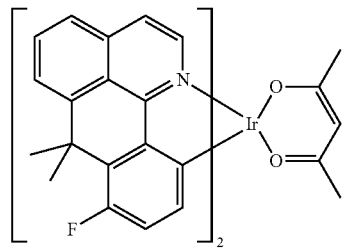
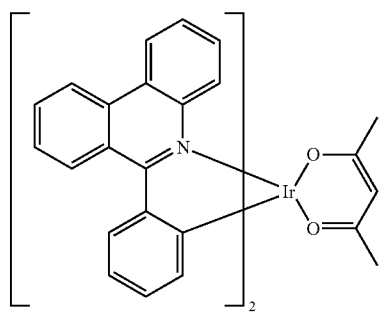
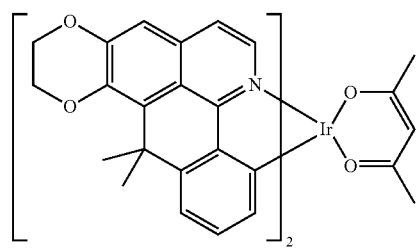

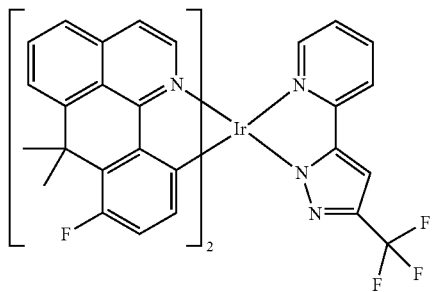 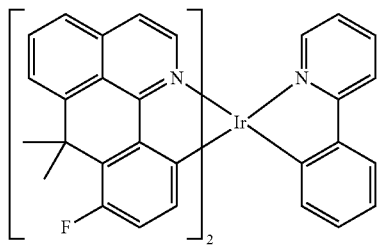
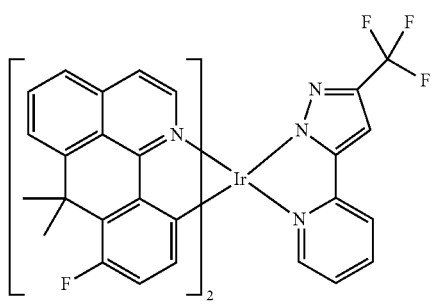 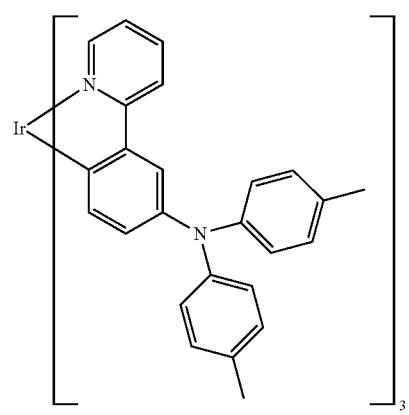
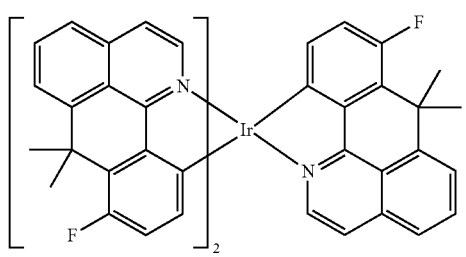 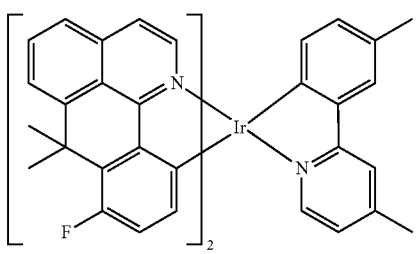
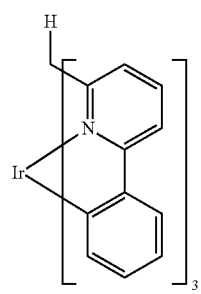 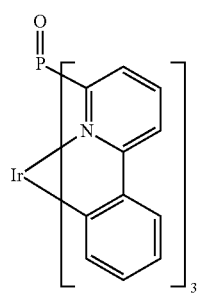
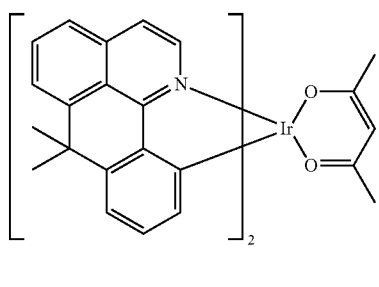 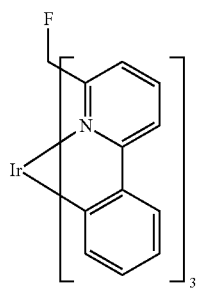

-continued
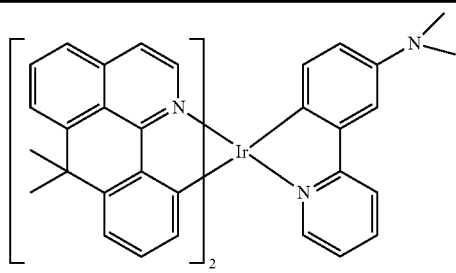
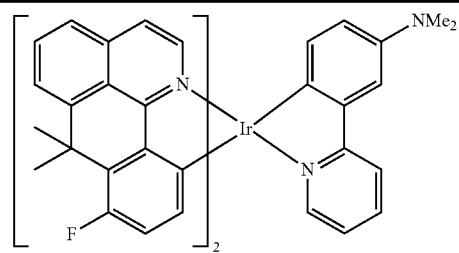
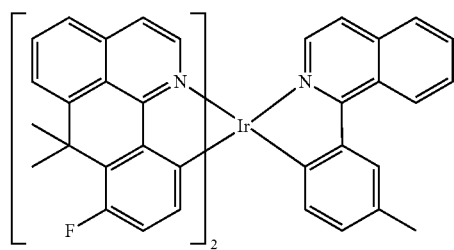
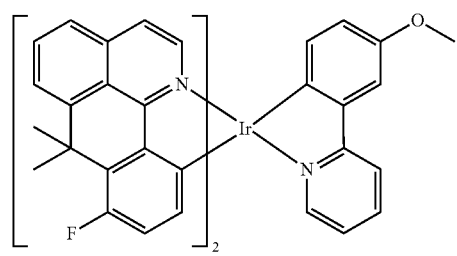
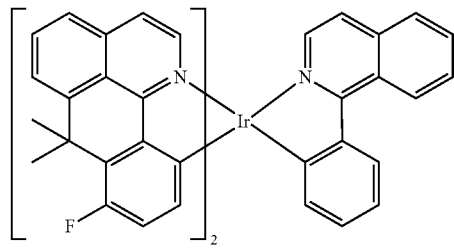
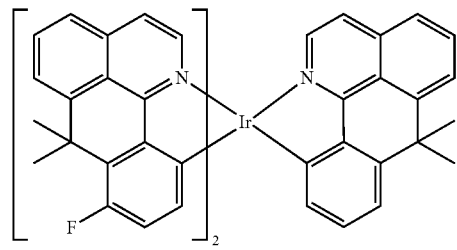
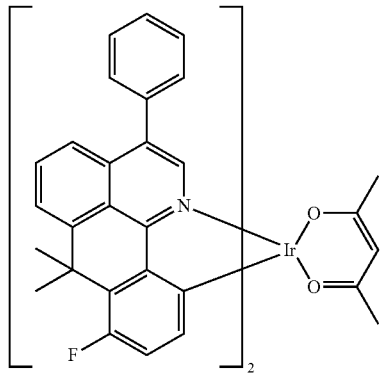
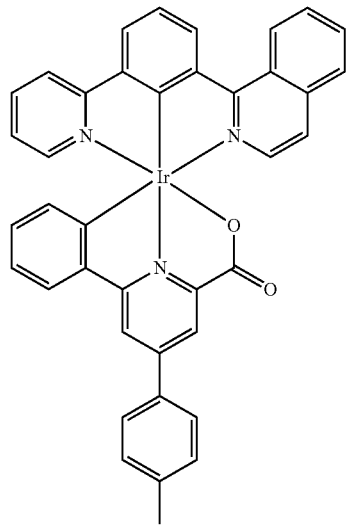

-continued
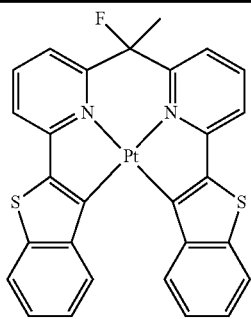
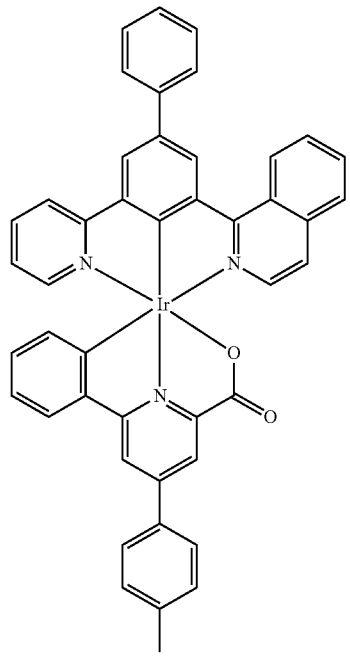
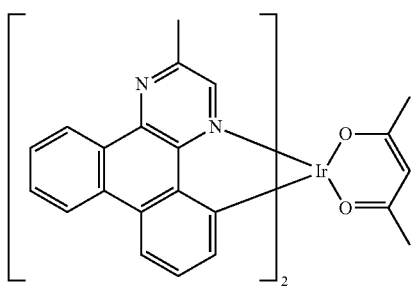
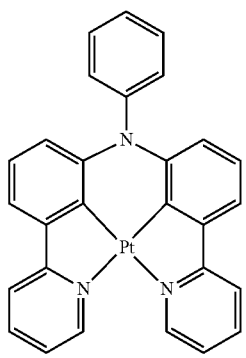
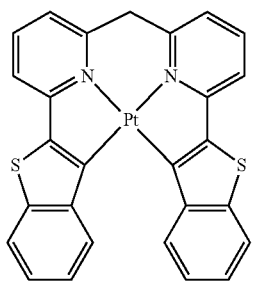
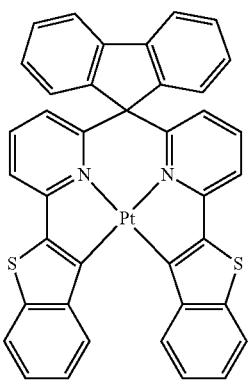
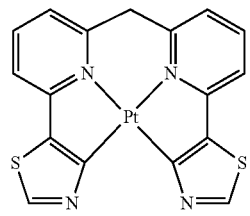
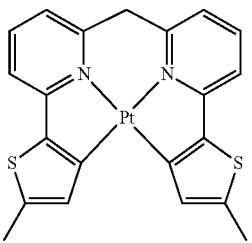

-continued
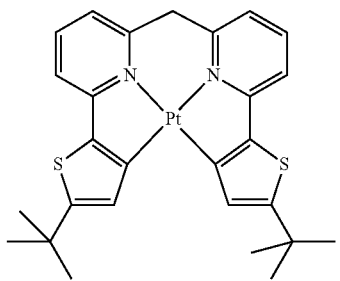
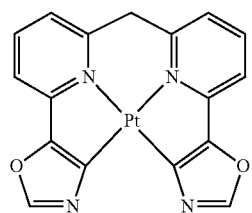
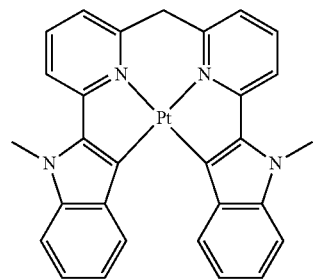
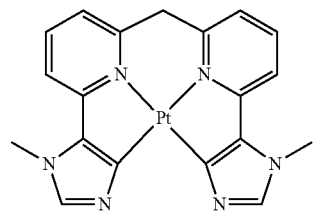
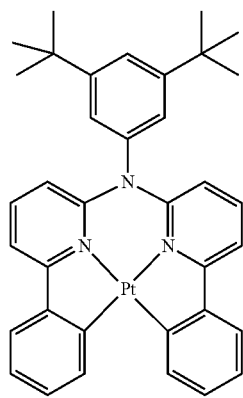
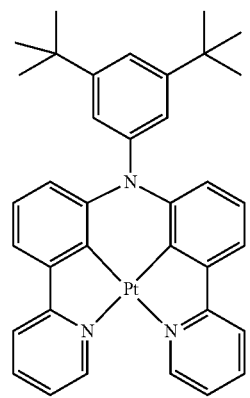
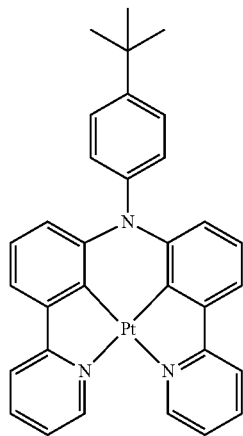
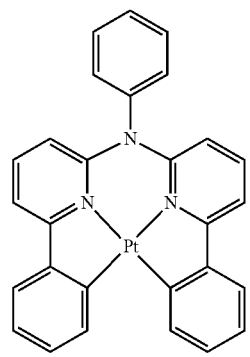

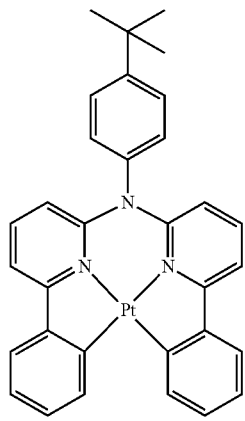
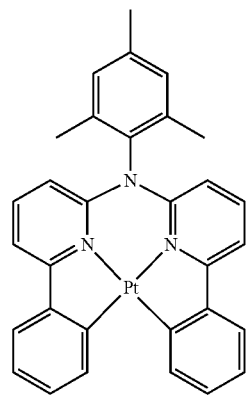
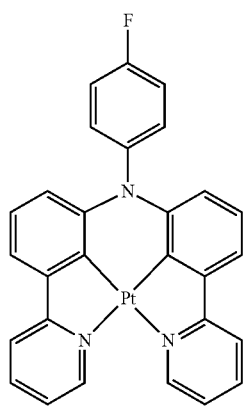
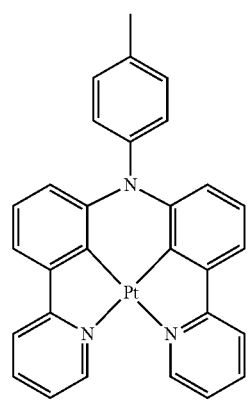
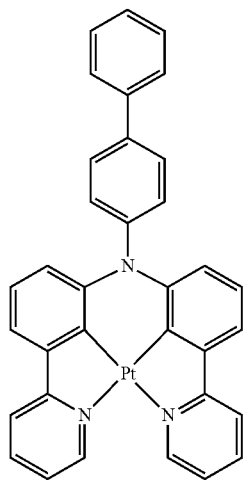
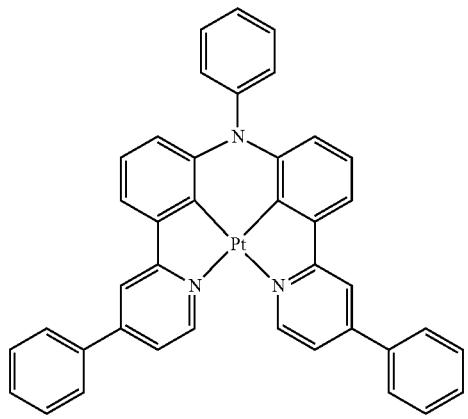

-continued
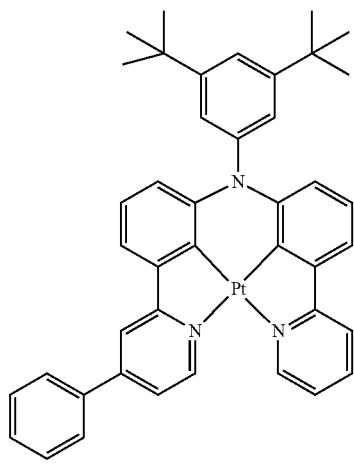
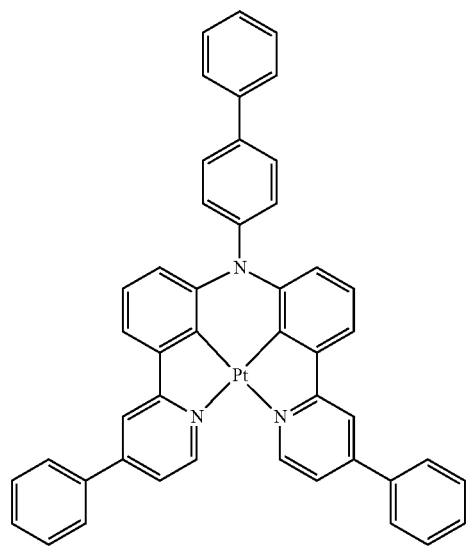
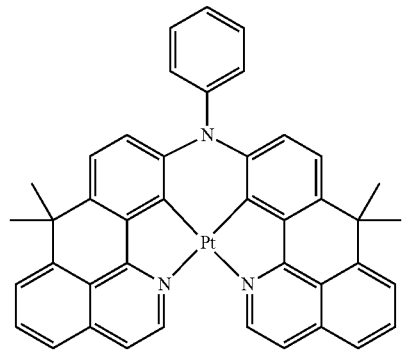
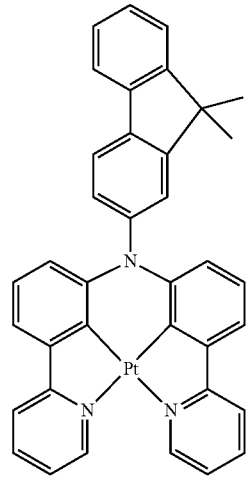
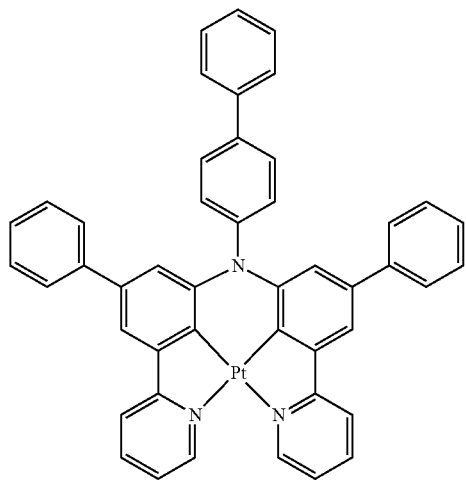
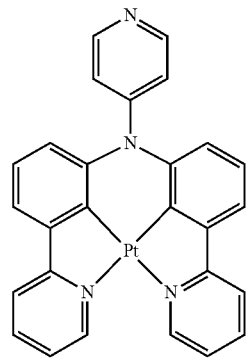

-continued
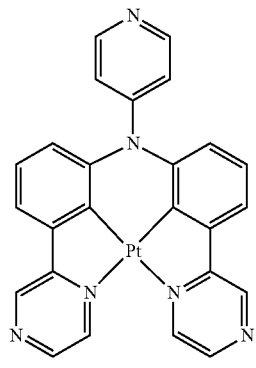
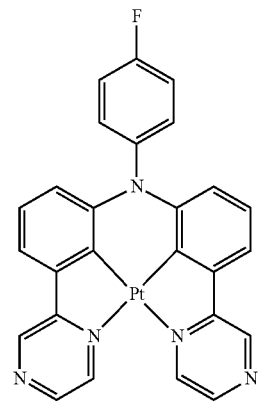
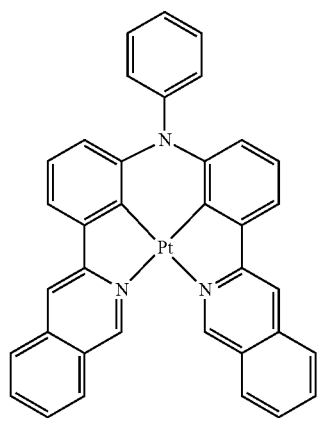
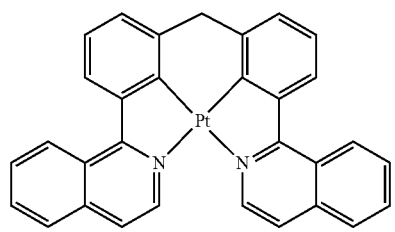
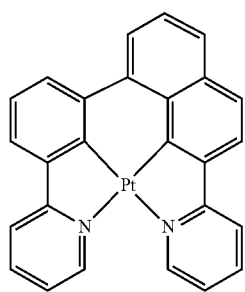
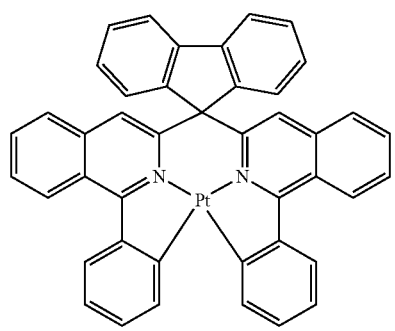
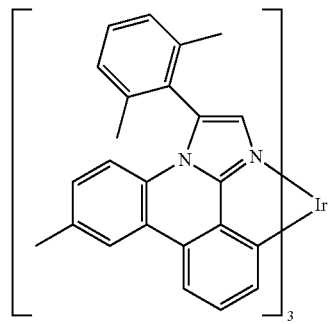
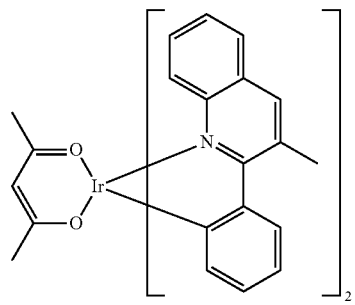

-continued
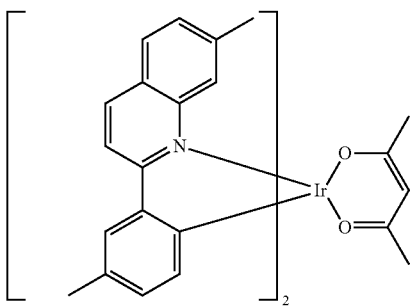
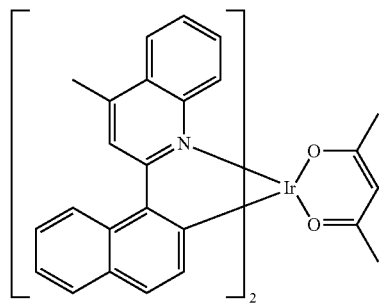
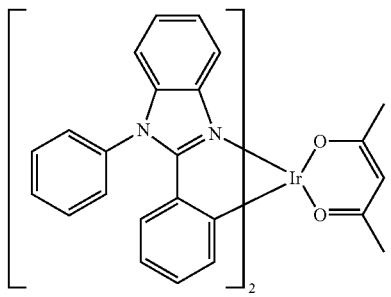
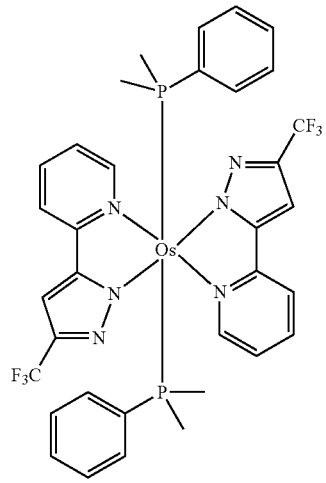
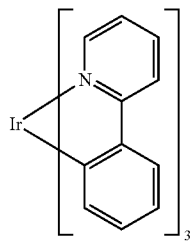
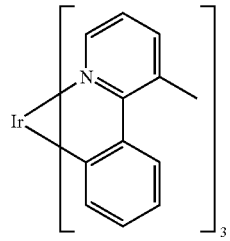
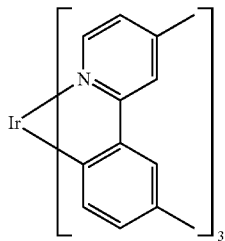
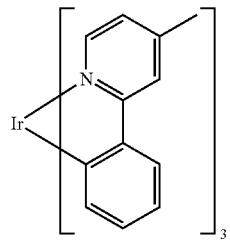
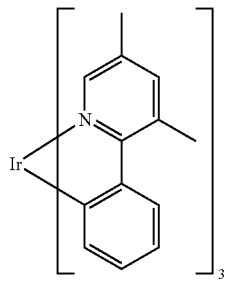
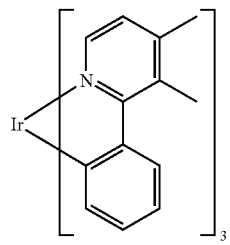

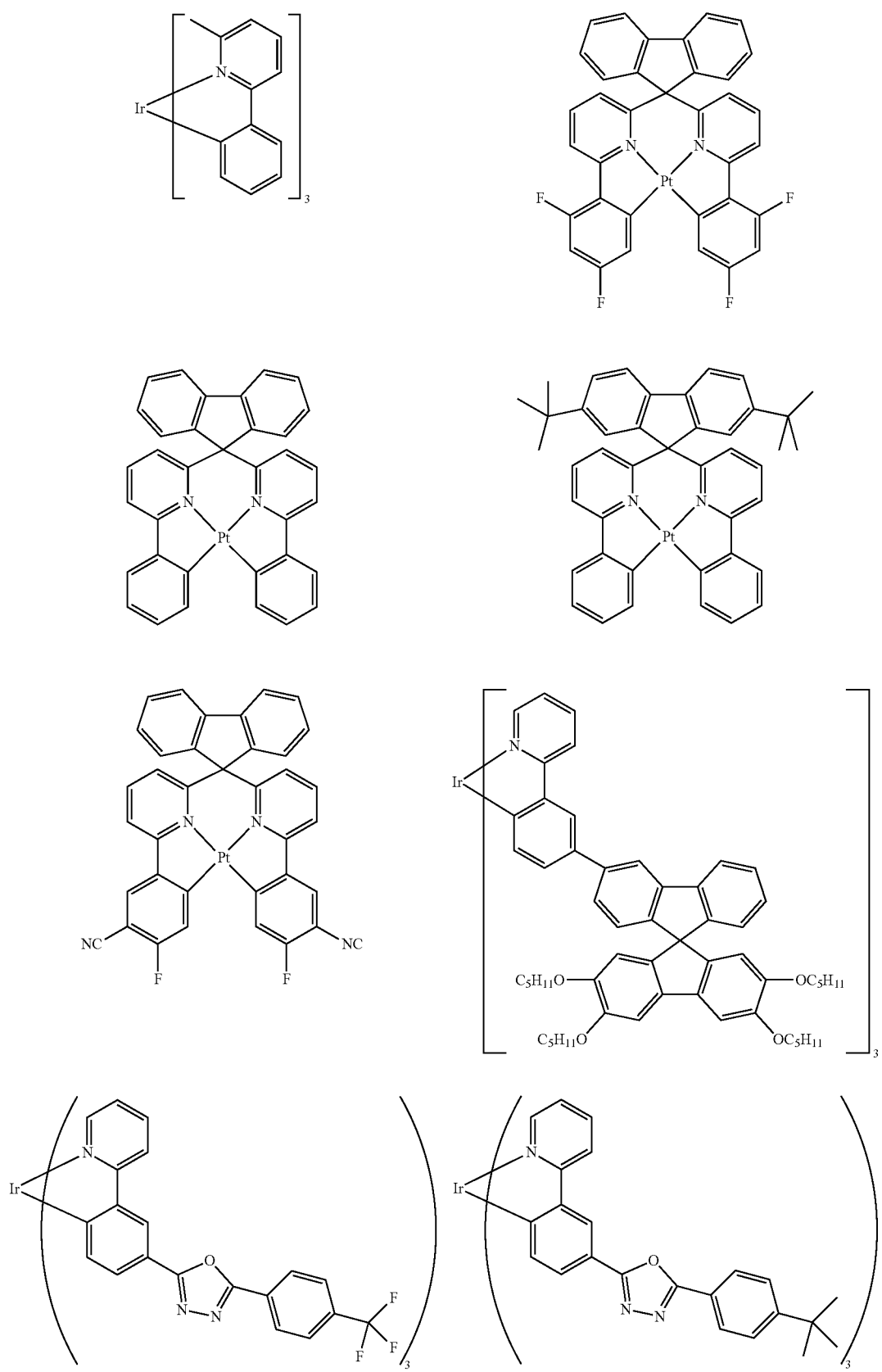

-continued
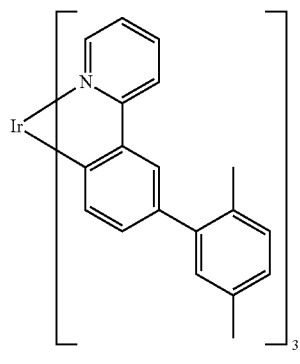
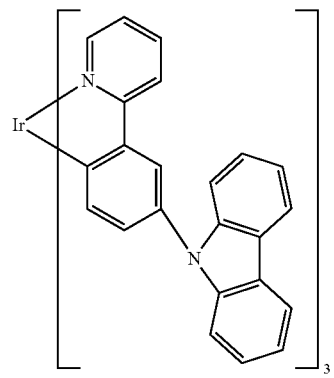
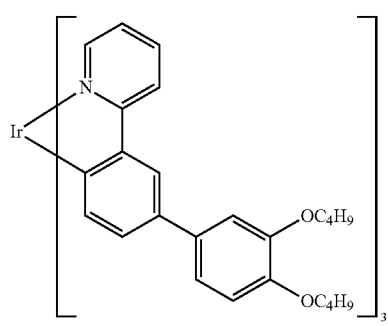
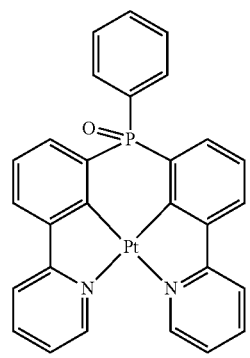
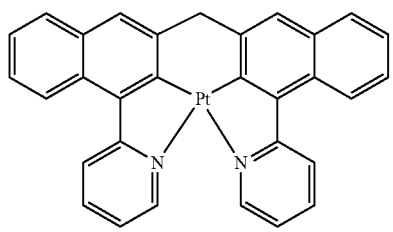
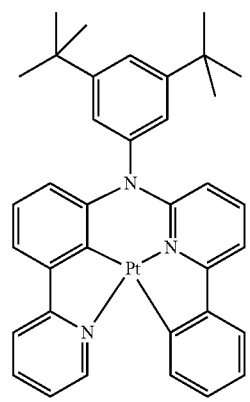
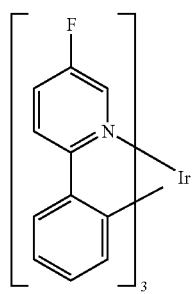
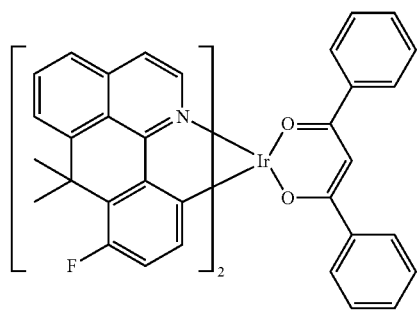

-continued
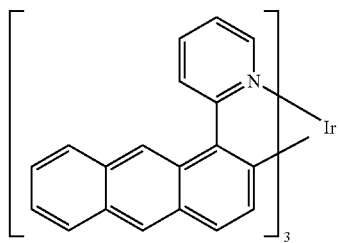
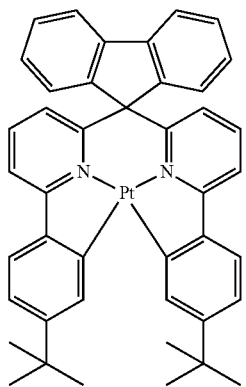
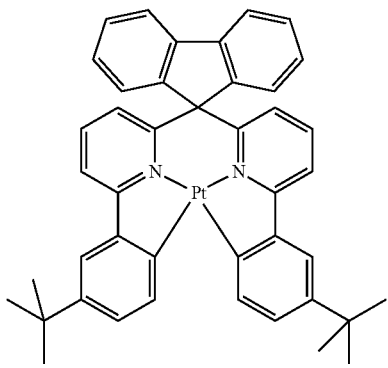
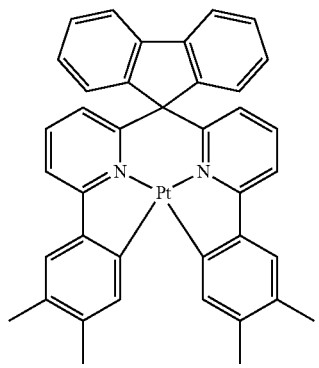
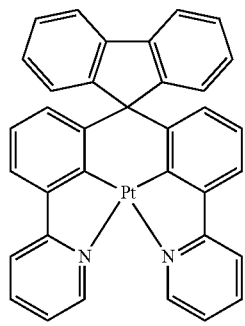
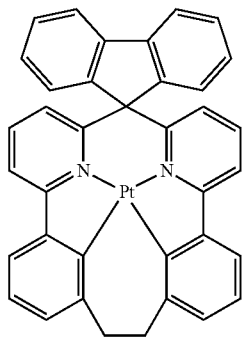
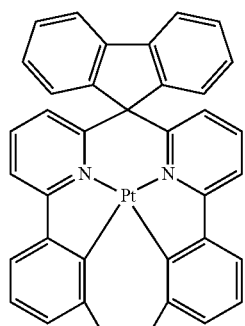
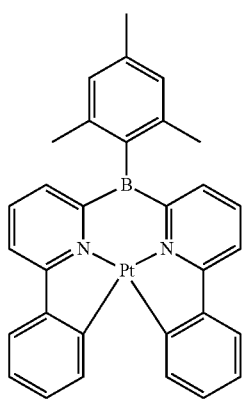

-continued
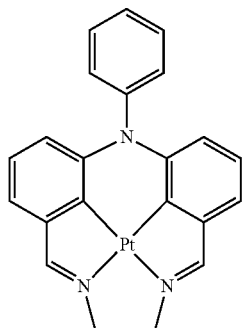
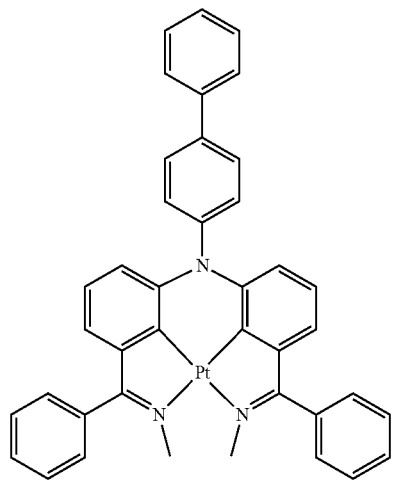
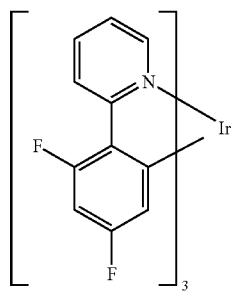
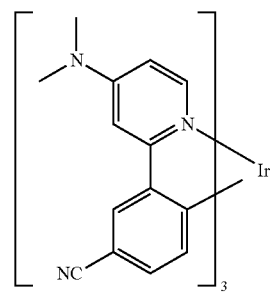
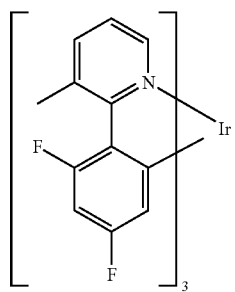
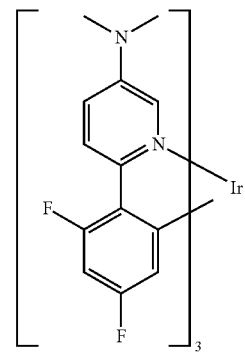
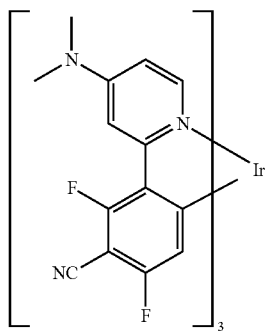
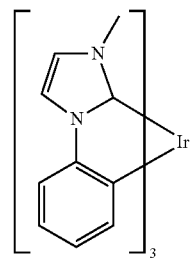

-continued
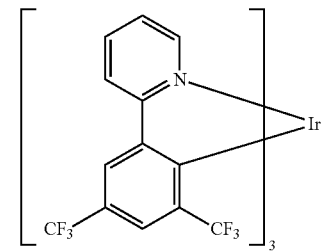
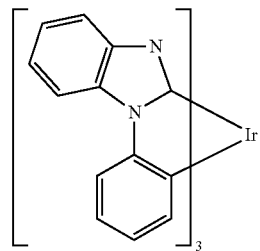
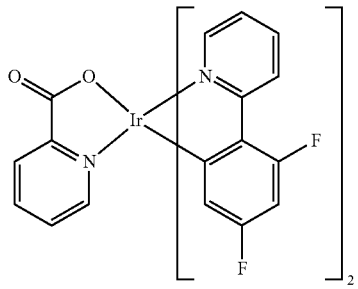
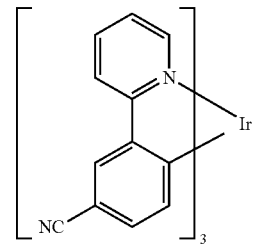
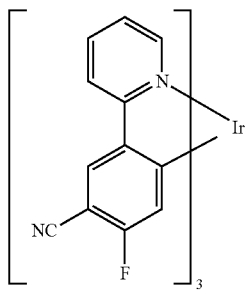
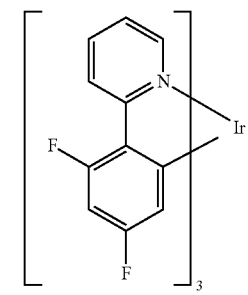
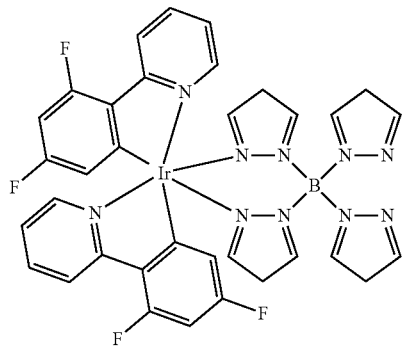
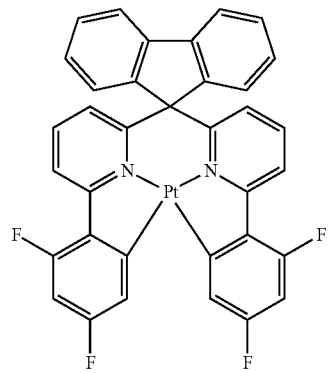
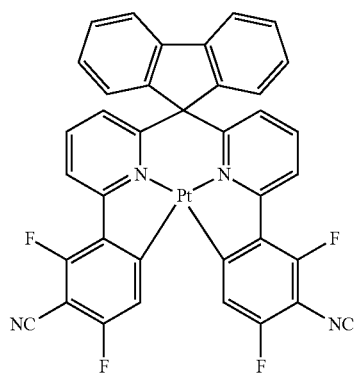
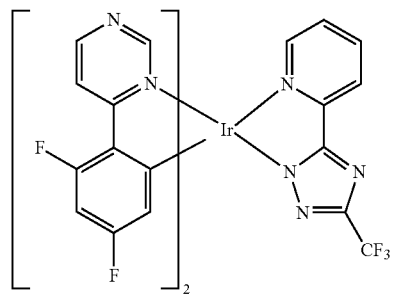

-continued
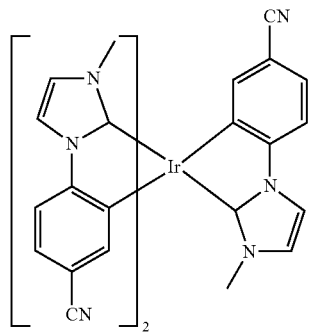
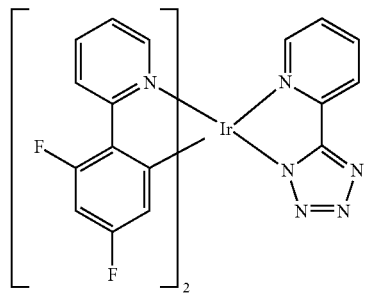
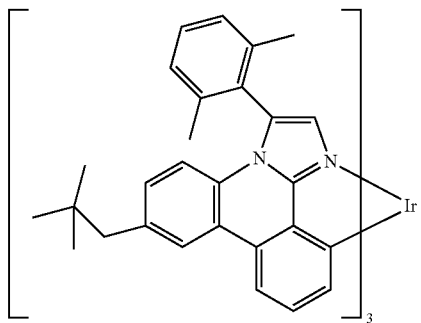
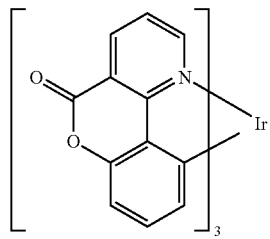
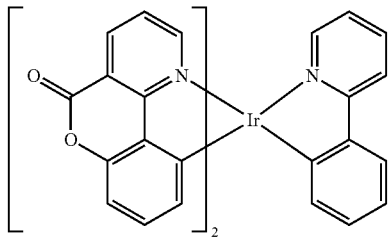
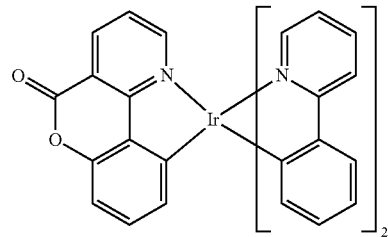
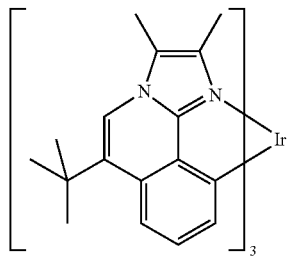
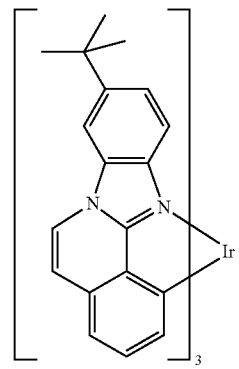
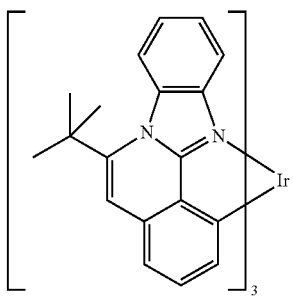
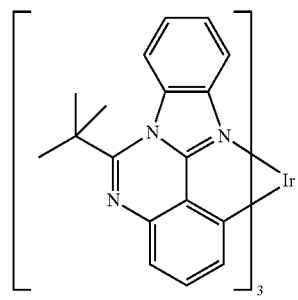

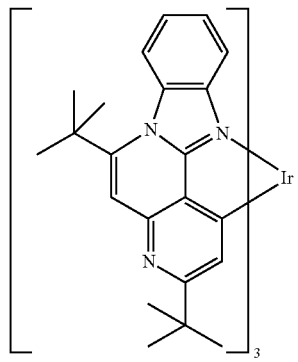 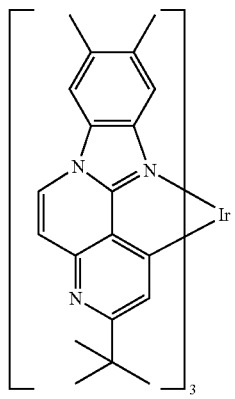

The above-described compound comprising structures of the formula (I) or the above-detailed preferred embodiments can preferably be used as active component in an electronic device. An electronic device is understood to mean any device comprising anode, cathode and at least one layer, said layer comprising at least one organic or organometallic compound. The electronic device of the invention thus comprises anode, cathode and at least one layer containing at least one compound comprising structures of the formula (I), or the preferred embodiments detailed above or below. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs) and organic laser diodes (O-lasers), containing at least one compound comprising structures of the formula (I) in at least one layer. Particular preference is given to organic electroluminescent devices. Active components are generally the organic or inorganic materials introduced between the anode and cathode, for example charge injection, charge transport or charge blocker materials, but especially emission materials and matrix materials. A preferred embodiment of the invention is organic electroluminescent devices. The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per) fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (I) or the above-detailed preferred embodiments as matrix material, preferably as electron-conducting matrix material, in one or more emitting layers, preferably in combination with a further matrix material, preferably a hole-conducting matrix material. An emitting layer comprises at least one emitting compound.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulphoxides and sulphones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture, especially of at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (I) or the preferred embodiments detailed above and below, in a preferred embodiment, as matrix material in an emission layer of an organic electronic device, especially in an organic electroluminescent device, for example in an OLED or OLEC. In this case, the matrix material containing compound comprising structures of formula (I) or the preferred embodiments detailed above and below is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (I) or the preferred embodiments detailed above and below is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapour deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device can also be produced as a hybrid system by applying one or more layers from solution and applying one or more other layers by vapour deposition. For example, it is possible to apply an emitting layer comprising a compound of the invention comprising structures of formula (I) or the preferred embodiments detailed above and below and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formula (I) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (I) or the preferred embodiments detailed above and below, especially as electron-conducting materials and/or as hole-conducting materials, have a very good lifetime.
2. Electronic devices, especially organic electroluminescent devices, comprising compounds, oligomers, polymers or dendrimers having structures of formula (I) or the preferred embodiments detailed above and below, as electron-conducting materials and/or as hole-conducting materials, have an excellent efficiency. More particularly, efficiency is much higher compared to analogous compounds containing no structural unit of formula (I).
3. The compounds, oligomers, polymers and dendrimers of the invention having structures of formula (I) or the preferred embodiments detailed above and below exhibit very high stability and lead to compounds having a very long lifetime.
4. With compounds, oligomers, polymers or dendrimers having structures of formula (I) or the preferred embodiments detailed above and below, it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (I) or the preferred embodiments detailed above and below in layers of electronic devices, especially organic electroluminescent devices, leads to a high mobility of the electron conductor structures and/or the hole conductor structures.
6. Compounds, oligomers, polymers and dendrimers having structures of formula (I) or the preferred embodiments detailed above and below feature excellent thermal stability, and compounds having a molar mass of less than about 1200 g/mol have good sublimability.
7. Compounds, oligomers, polymers and dendrimers having structures of formula (I) or the preferred embodiments detailed above and below have excellent glass film formation.
8. Compounds, oligomers, polymers and dendrimers having structures of formula (I) or the preferred embodiments detailed above and below form very good films from solutions.
9. The compounds, oligomers, polymers and dendrimers comprising structures of formula (I) or the preferred embodiments detailed above and below have a surprisingly high triplet level $T_1$, this being particularly true of compounds which are used as electron-conducting materials.

These abovementioned advantages are not accompanied by a deterioration in the further electronic properties.

The present invention further provides for the use of a compound of the invention and/or an oligomer, polymer or dendrimer of the invention in an electronic device as hole transport material, hole injection material, hole blocker material, electron injection material, electron blocker material and/or electron transport material.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

Synthesis Examples a) 3-Dibenzofuran-4-yl-9H-carbazole

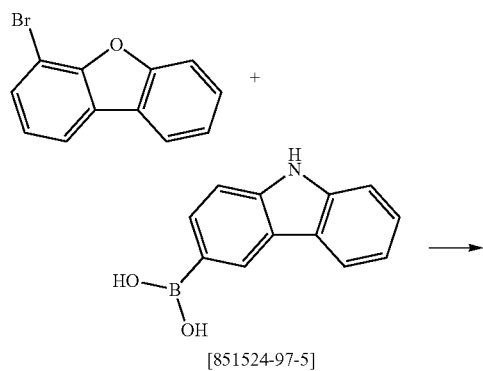

[851524-97-5]

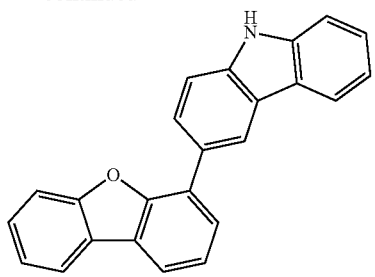

6.75 g (32 mmol) of B-(9H-carbazol-3-yl)boronic acid, 7.8 g (31.6 mmol) of 4-bromodibenzofuran, 31 ml (63 mmol) of $Na_2CO_3$ (2 M solution) are suspended in 120 ml of toluene and 120 ml of ethanol. 0.73 g (0.63 mmol) of $Pd(PPh_3)_4$ is added to this suspension, and the reaction mixture is heated under reflux for 16 h. After cooling, the organic phase is removed, filtered through silica gel, washed three times with 200 ml of water and then concentrated to dryness. The residue is recrystallized from toluene. The yield is 7.66 g (23 mmol), corresponding to 73% of theory.

In an analogous manner, it is possible to obtain the following compounds:

| | Reactant 1 | Reactant 2 |
|---|---|---|
| a1 | [22439-61-8] | [851524-97-5] |
| a2 | [65642-94-6] | [851524-97-5] |
| a3 | [955959-84-9] | [851524-97-5] | a4 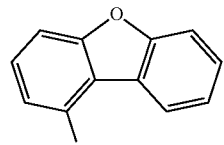
[50548-45-3]
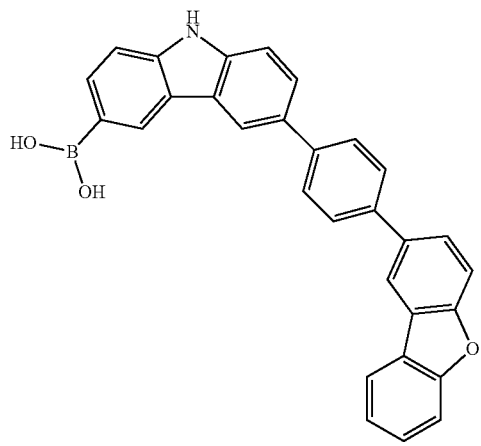
[1446005-05-3]
a5 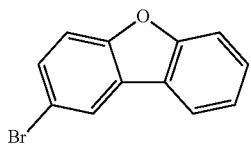
22439-61-8]
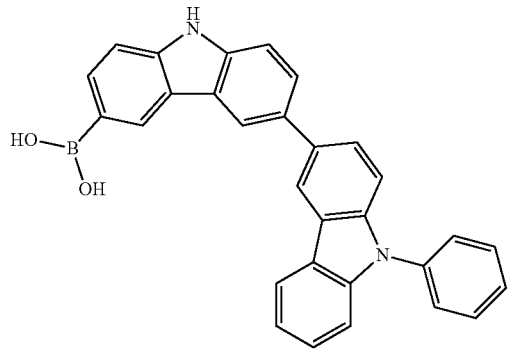
[1440005-92-0]
a6 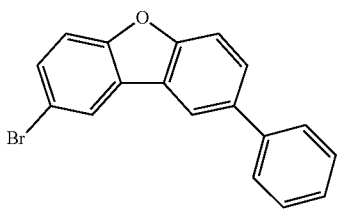
[1338446-67-5]
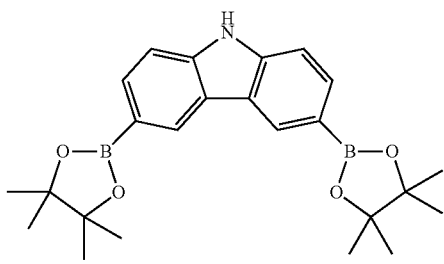
1487428-49-8]
a7 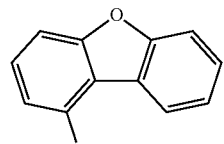
[50548-45-3]
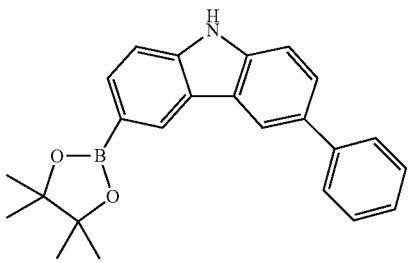
[1303472-74-3]

-continued
a8 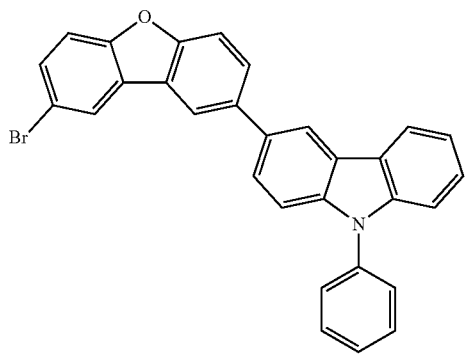
[1177264-86-6]
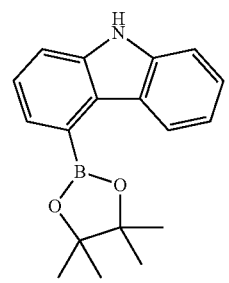
[1255309-13-7]
a9 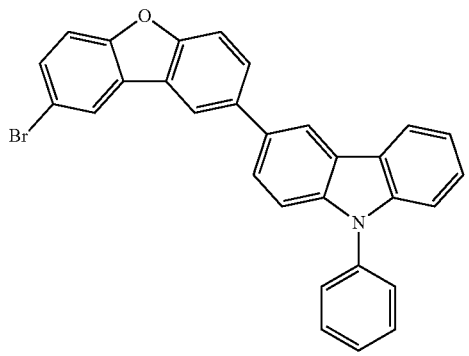
[1177264-86-6]
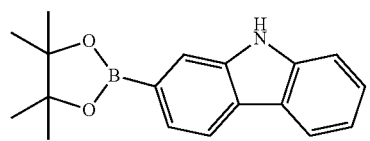
[1242412-60-7]
a10 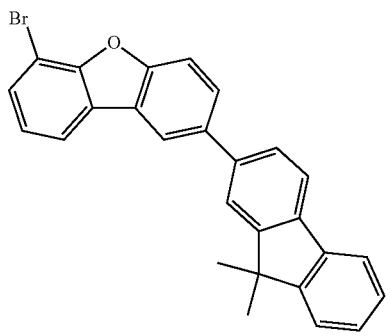
[1010060-04-1]
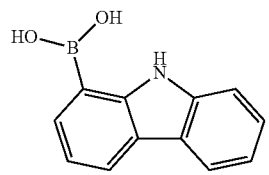
[869642-36-4]
a11 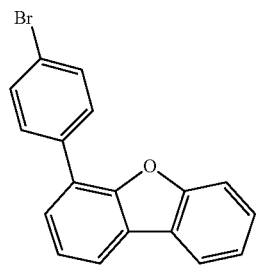
[955959-84-9]
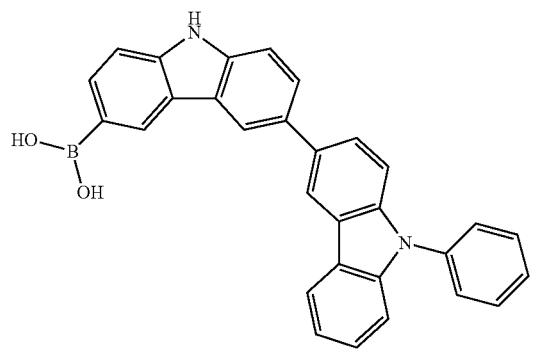
[1440005-02-0]

| | | | |
|---|---|---|---|
| a12 | 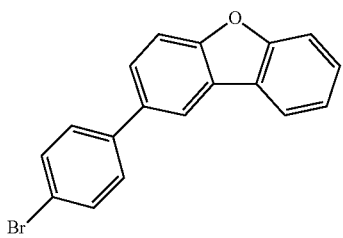<br>[955959-86-1] | 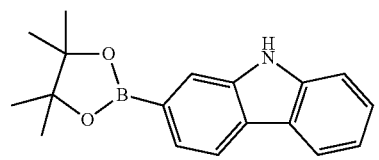<br>[1242412-80-7] | |
| a13 | 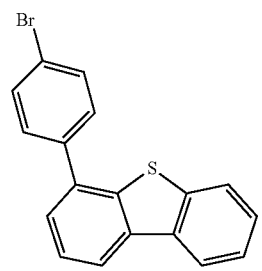<br>[530402-77-8] | 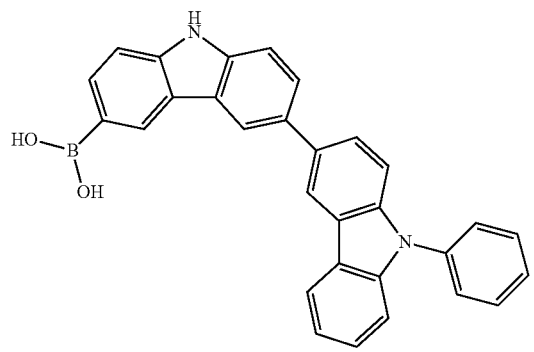<br>[1440005-92-0] | |
| a14 | 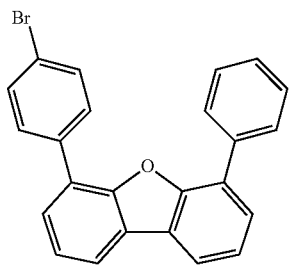<br>[1556069-46-5] | 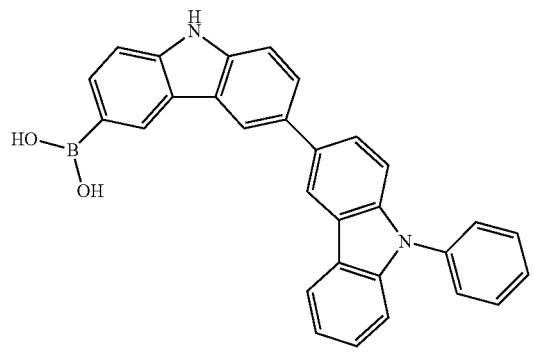<br>[1446005-92-0] | |
| a15 | 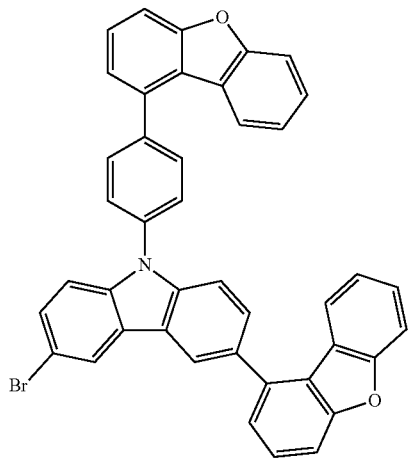 [SMILES: Brc1ccc2c(c1)c1cc(-c3cccc4oc5ccccc5c34)ccc1n2-c1ccc(-c2cccc3oc4ccccc4c23)cc1] | 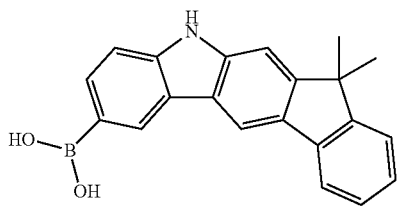<br>[1357286-77-1] | |

-continued
| | Product | Yield |
|---|---|---|
| a1 | 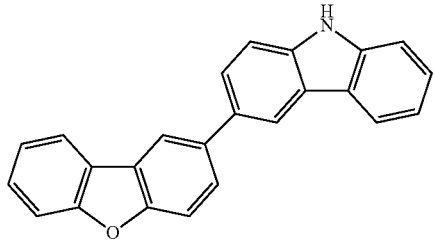 [SMILES: c1ccc2c(c1)[nH]c1ccc(-c3ccc4oc5ccccc5c4c3)cc12] | 67% |
| a2 | 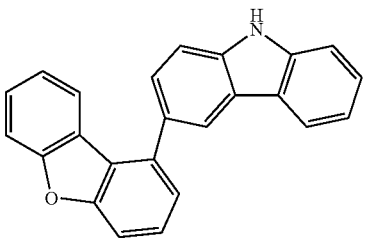 [SMILES: c1ccc2c(c1)[nH]c1ccc(-c3cccc4oc5ccccc5c34)cc12] | 72% |
| a3 | 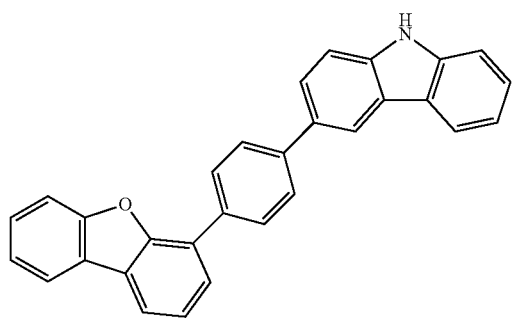 [SMILES: c1ccc2c(c1)[nH]c1ccc(-c3ccc(-c4cccc5c4oc4ccccc45)cc3)cc12] | 79% |
| a4 | 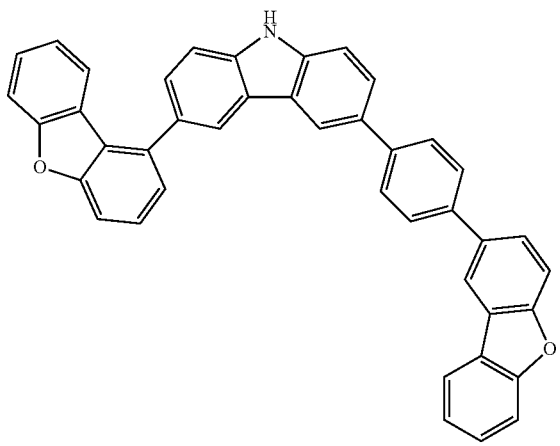 [SMILES: c1ccc2c(c1)oc1ccc(-c3ccc(-c4ccc5[nH]c6ccc(-c7cccc8oc9ccccc9c78)cc6c5c4)cc3)cc12] | 81% |

-continued
a5 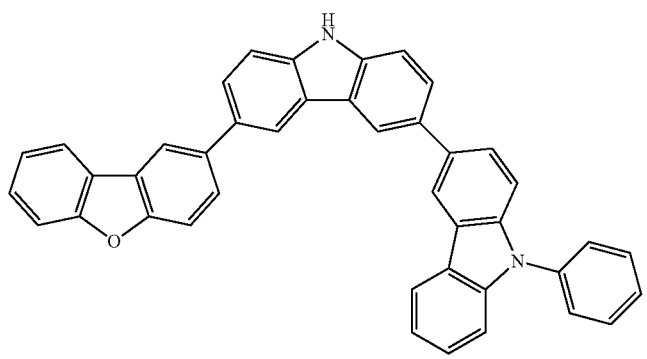 [SMILES: c1ccc(-n2c3ccccc3c3cc(-c4ccc5[nH]c6ccc(-c7ccc8oc9ccccc9c8c7)cc6c5c4)ccc32)cc1] 79%
a6 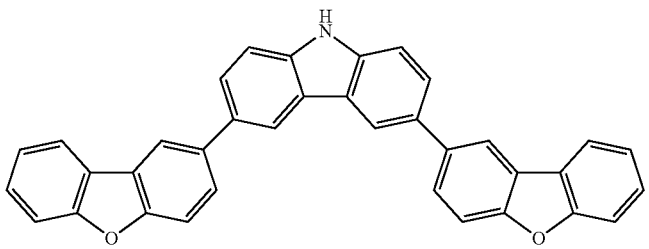 [SMILES: c1ccc2c(c1)oc1ccc(-c3ccc4[nH]c5ccc(-c6ccc7oc8ccccc8c7c6)cc5c4c3)cc12] 79%
a7 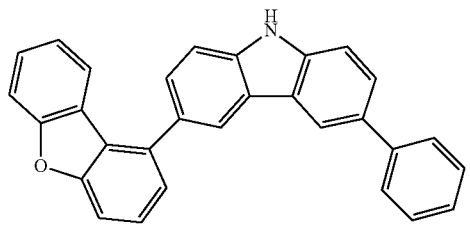 [SMILES: c1ccc(-c2ccc3[nH]c4ccc(-c5cccc6oc7ccccc7c56)cc4c3c2)cc1] 82%
a8 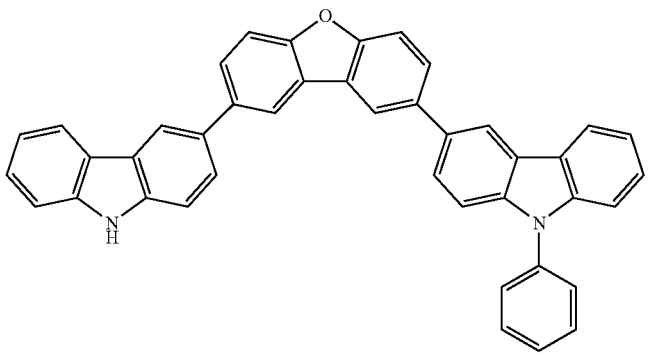 [SMILES: c1ccc(-n2c3ccccc3c3cc(-c4ccc5oc6ccc(-c7ccc8[nH]c9ccccc9c8c7)cc6c5c4)ccc32)cc1] 69%
a9 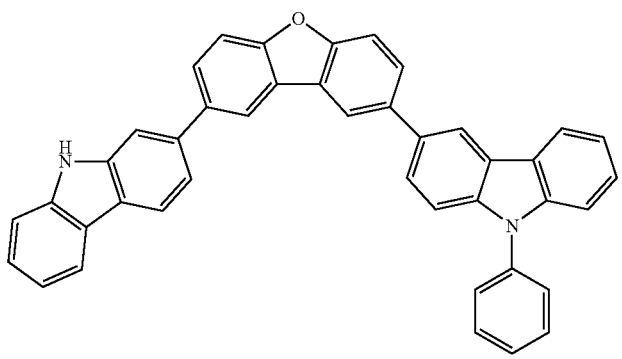 [SMILES: c1ccc(-n2c3ccccc3c3cc(-c4ccc5oc6ccc(-c7ccc8c(c7)[nH]c7ccccc78)cc6c5c4)ccc32)cc1] 74%

-continued
| | | |
|---|---|---|
| a10 | 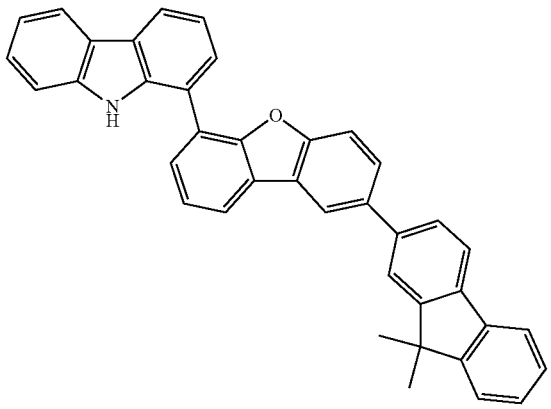 [SMILES: CC1(C)c2ccccc2-c2ccc(-c3ccc4oc5c(-c6cccc7c6[nH]c6ccccc67)cccc5c4c3)cc21] | 76% |
| a11 | 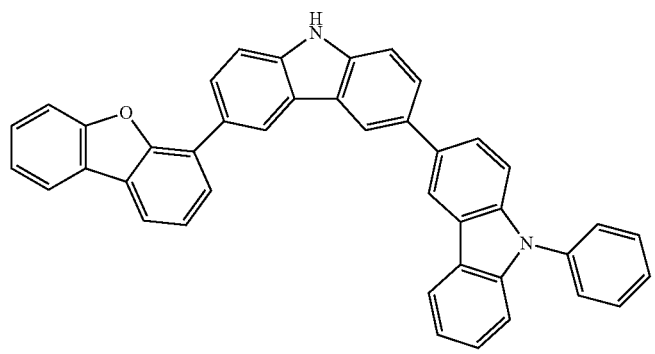 [SMILES: c1ccc(-n2c3ccccc3c3cc(-c4ccc5[nH]c6ccc(-c7cccc8c7oc7ccccc78)cc6c5c4)ccc32)cc1] | 68% |
| a12 | 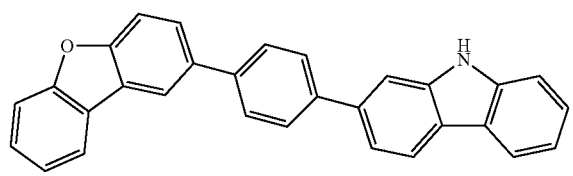 [SMILES: c1ccc2c(c1)[nH]c1cc(-c3ccc(-c4ccc5oc6ccccc6c5c4)cc3)ccc12] | 75% |
| a13 | 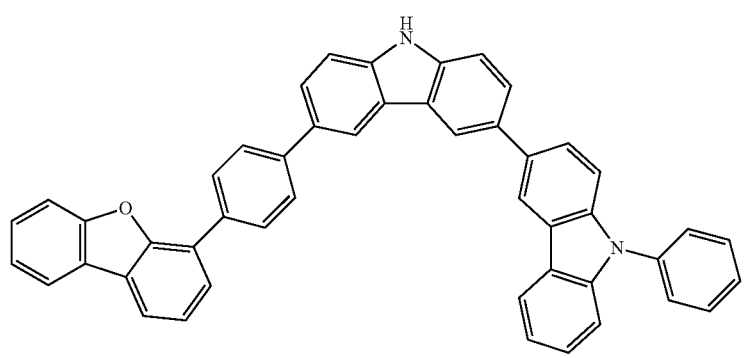 [SMILES: c1ccc(-n2c3ccccc3c3cc(-c4ccc5[nH]c6ccc(-c7ccc(-c8cccc9c8oc8ccccc89)cc7)cc6c5c4)ccc32)cc1] | 67% |
| a14 | 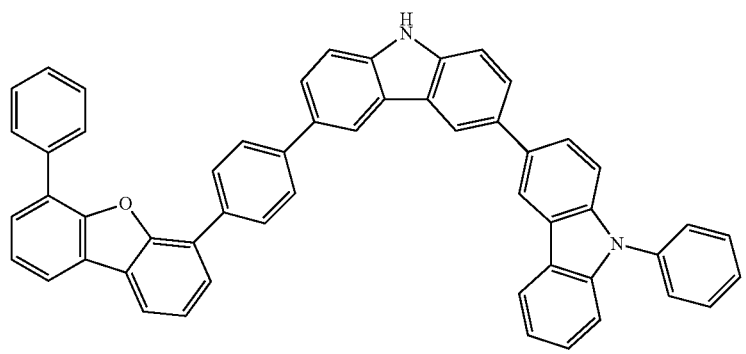 [SMILES: c1ccc(-c2cccc3c2oc2c(-c4ccc(-c5ccc6[nH]c7ccc(-c8ccc9c(c8)c8ccccc8n9-c8ccccc8)cc7c6c5)cc4)cccc23)cc1] | 77% |

| | | |
|---|---|---|
| a15 | 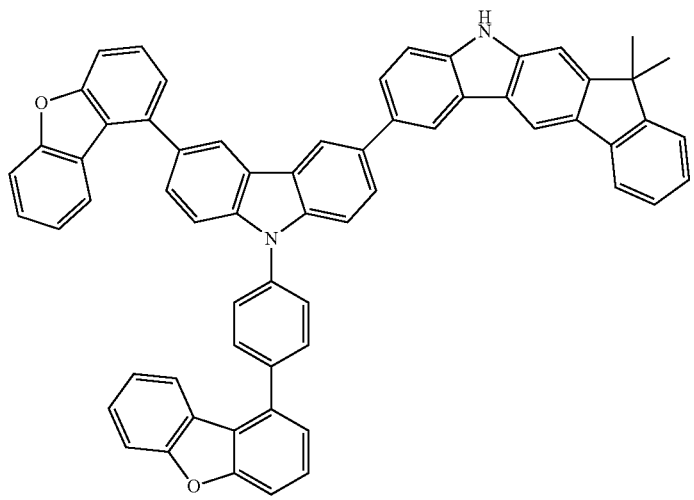 [SMILES: CC1(C)c2ccccc2-c2cc3c(cc21)[nH]c1ccc(-c2ccc4c(c2)c2cc(-c5cccc6oc7ccccc7c56)ccc2n4-c2ccc(-c4cccc5oc6ccccc6c45)cc2)cc13] | 76% |
In the case of the compounds which follow, the residue is subjected to hot extraction with toluene, recrystallized from toluene and finally sublimed under high vacuum. HPLC purity is greater than 99.9%.
| | Reactant 1 | Reactant 2 |
|---|---|---|
| a16 | 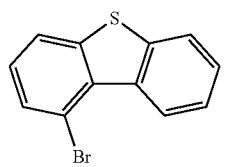<br>[65642-94-6] | 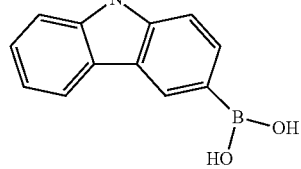<br>[1257324-73-4] |
| a17 | 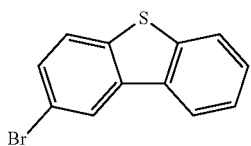<br>[82024-22-4] | 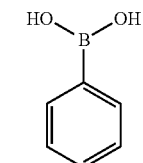<br>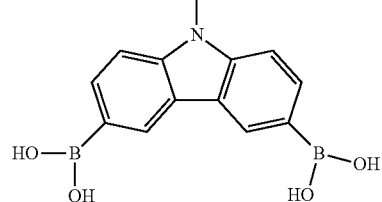<br>[1416368-44-9] |

-continued
a18 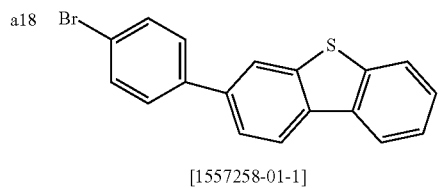
[1557258-01-1]
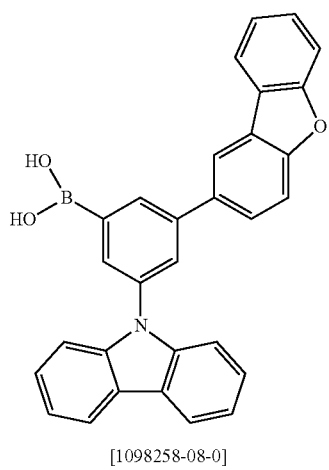 [SMILES: OB(O)c1cc(-c2ccc3oc4ccccc4c3c2)cc(-n2c3ccccc3c3ccccc32)c1]
[1098258-08-0]
a19 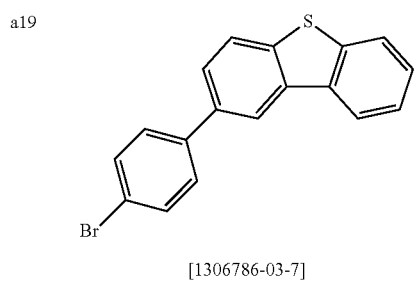
[1306786-03-7]
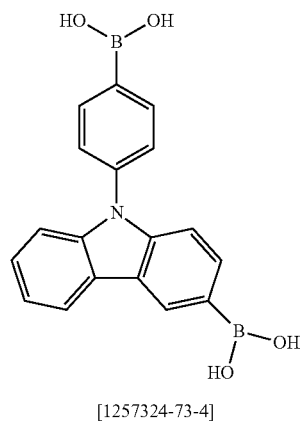 [SMILES: OB(O)c1ccc(-n2c3ccccc3c3cc(B(O)O)ccc32)cc1]
[1257324-73-4]
a20 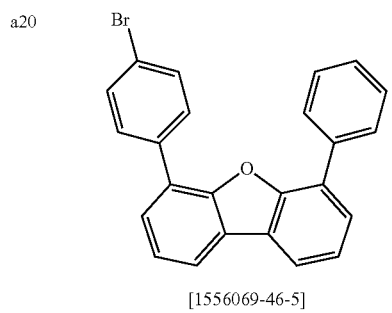
[1556069-46-5]
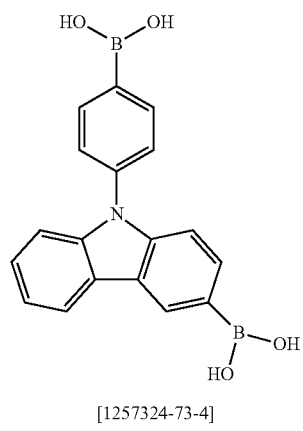 [SMILES: OB(O)c1ccc(-n2c3ccccc3c3cc(B(O)O)ccc32)cc1]
[1257324-73-4]

a21 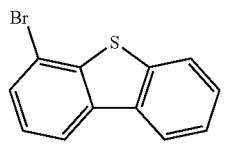
[97511-05-2]
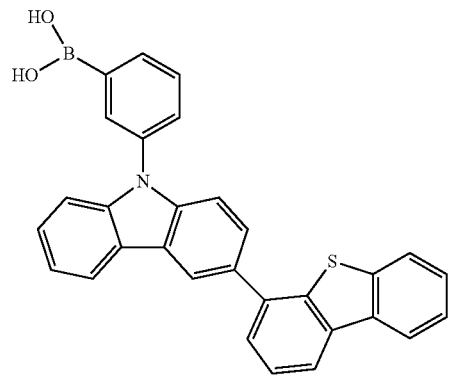
1420067-45-3]
a22 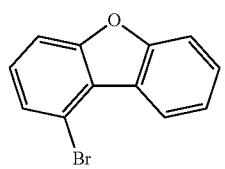
[50548-45-3]
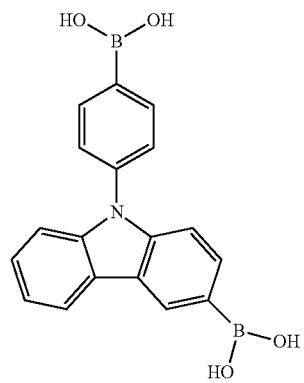
[1257324-73-4]
| | Product | Yield |
|---|---|---|
| a16 | 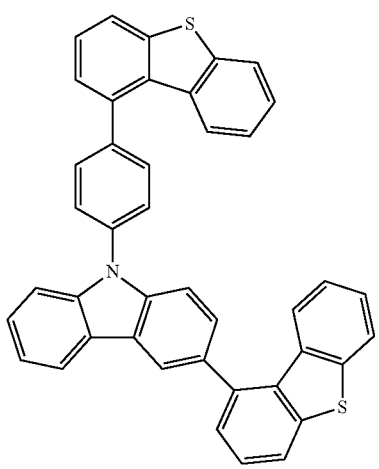 | 63% | a17 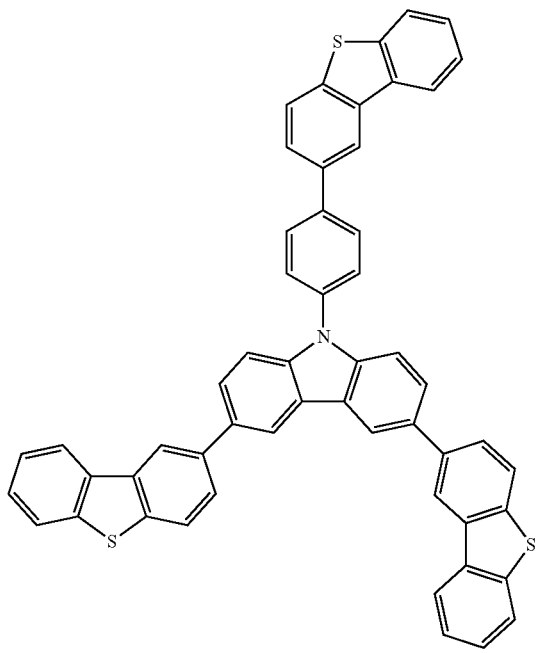 [SMILES: c1ccc2c(c1)sc1ccc(-c3ccc(-n4c5ccc(-c6ccc7sc8ccccc8c7c6)cc5c5cc(-c6ccc7sc8ccccc8c7c6)ccc54)cc3)cc12] 64%
a18 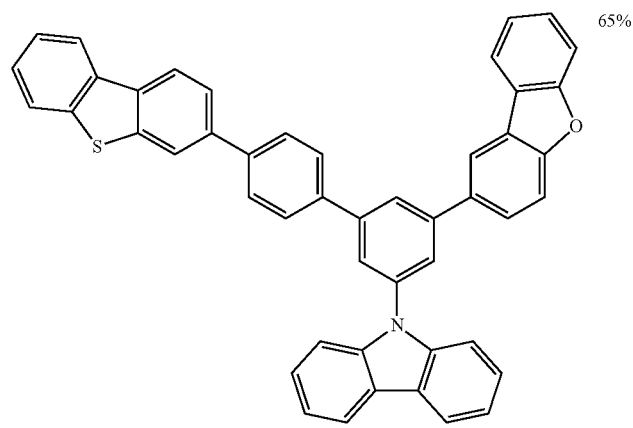 65%

| a19 | 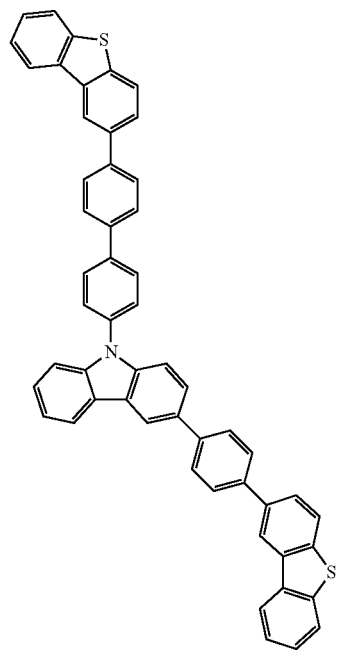 [SMILES: c1ccc2c(c1)sc1ccc(-c3ccc(-c4ccc(-n5c6ccccc6c6cc(-c7ccc(-c8ccc9sc%10ccccc%10c9c8)cc7)ccc65)cc4)cc3)cc12] | 60% |
| a20 | 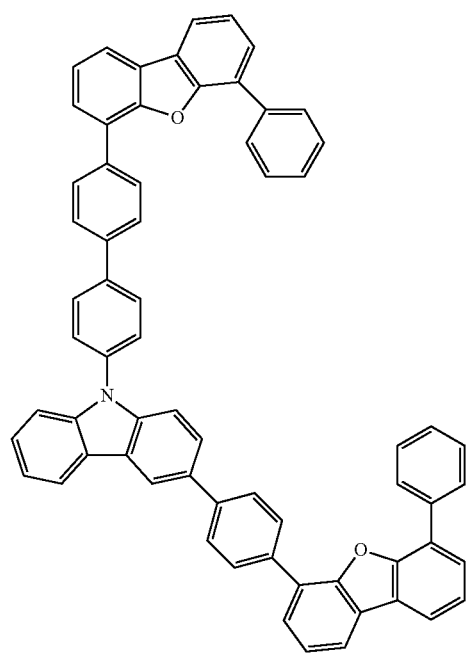 [SMILES: c1ccc(-c2cccc3c2oc2c(-c4ccc(-c5ccc(-n6c7ccccc7c7cc(-c8ccc(-c9cccc%10c9oc9c(-c%11ccccc%11)cccc9%10)cc8)ccc76)cc5)cc4)cccc23)cc1] | 63% |

| | |
|---|---|
| a21 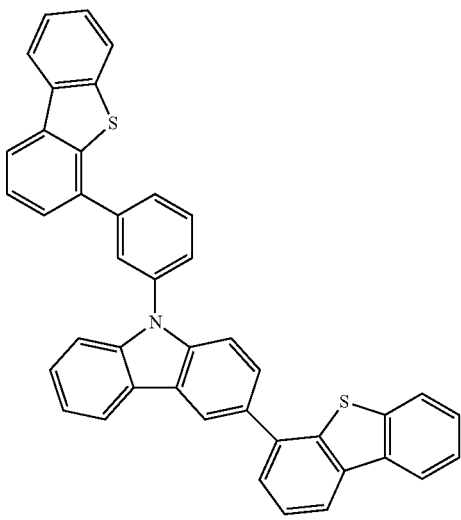 [SMILES: c1cc(-c2cccc3c2sc2ccccc23)cc(-n2c3ccccc3c3cc(-c4cccc5c4sc4ccccc45)ccc32)c1] | 67% |
| a22 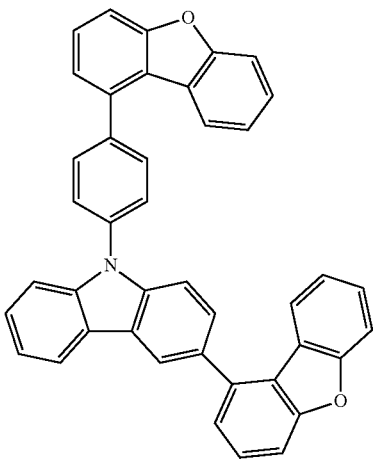 [SMILES: c1ccc2c(c1)oc1cccc(-c3ccc(-n4c5ccccc5c5cc(-c6cccc7oc8ccccc8c67)ccc54)cc3)c12] | 77% | b) 7-Bromo-10-(3-dibenzothiophen-4-yl-phenyl)-12,12-dimethyl-10,12-dihydro-10-azaindeno[2,1-b]fluorene

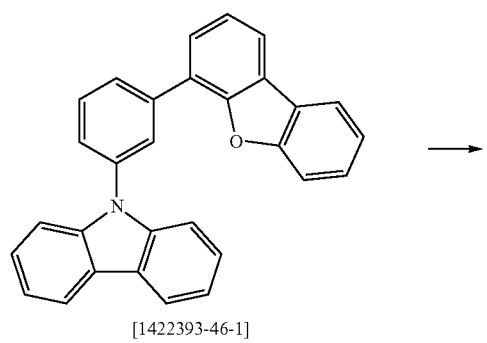

[1422393-46-1]

→

-continued

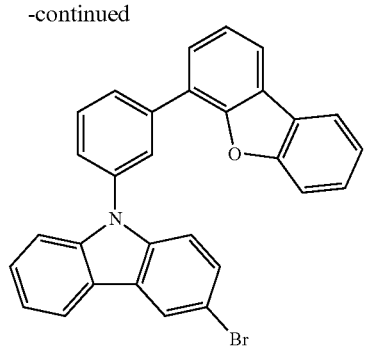

15.2 g (37.3 mmol) of 9-(3-dibenzofuran-4-yl-phenyl)-9H-carbazole are initially charged in 80 ml of DMF. Subsequently, 13.3 g (74.6 mmol) of NBS are added in portions and stirring is continued at this temperature for 4 h. Subsequently, 15 ml of water are added to the mixture and extraction is effected with $CH_2Cl_2$. The organic phase is dried over $MgSO_4$ and the solvents are removed under reduced pressure. The product is subjected to extractive stirring with hot hexane and filtered off with suction. Yield: 14.6 g (29 mmol), 78% of theory, purity by 1H NMR about 97%.

| Reactant 1 | Product | Yield |
|---|---|---|
| b1 | | 68% |
| b2 | | 64% |
| b3 | | 63% |

-continued
| | Reactant 1 | Product | Yield |
|---|---|---|---|
| b4 | 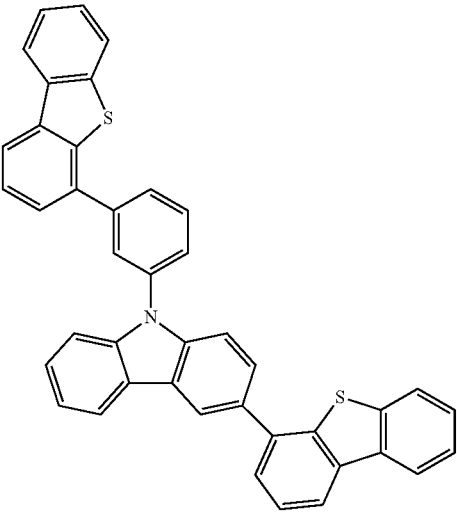 [SMILES: c1cc(-c2cccc3c2sc2ccccc23)cc(-n2c3ccccc3c3cc(-c4cccc5c4sc4ccccc45)ccc32)c1] | 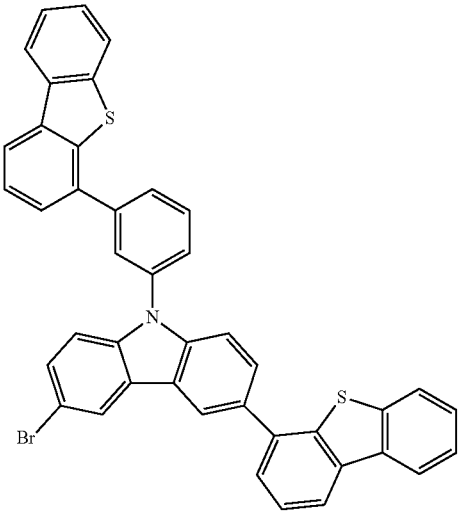 [SMILES: Brc1ccc2c(c1)c1cc(-c3cccc4c3sc3ccccc34)ccc1n2-c1cccc(-c2cccc3c2sc2ccccc23)c1] | 67% |
| b5 | 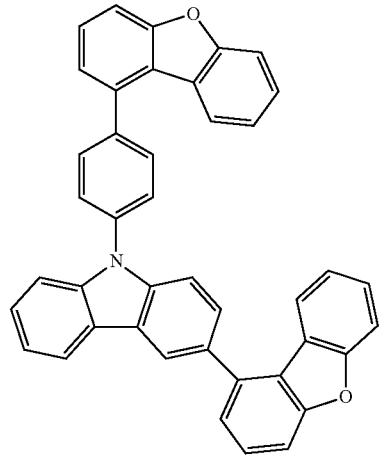 | 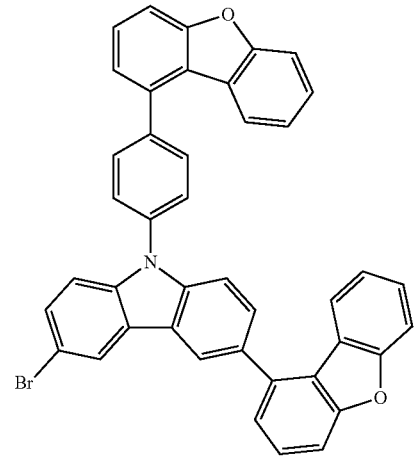 [SMILES: Brc1ccc2c(c1)c1cc(-c3cccc4sc5ccccc5c34)ccc1n2-c1ccc(-c2cccc3sc4ccccc4c23)cc1] | 65% |
| b6 | 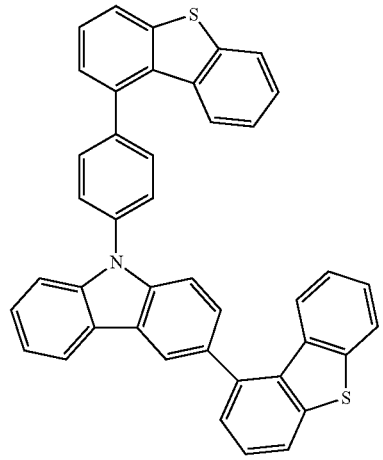 | 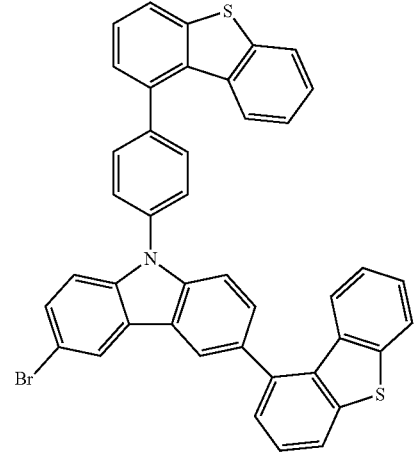 | 66% | c) 3-Dibenzofuran-4-yl-9-(4-dibenzofuran-4-ylphenyl)-9H-carbazole

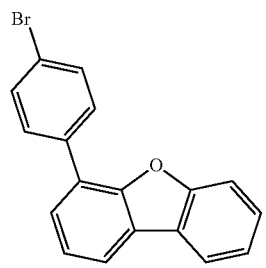

+

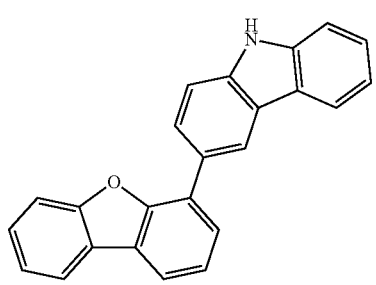

→

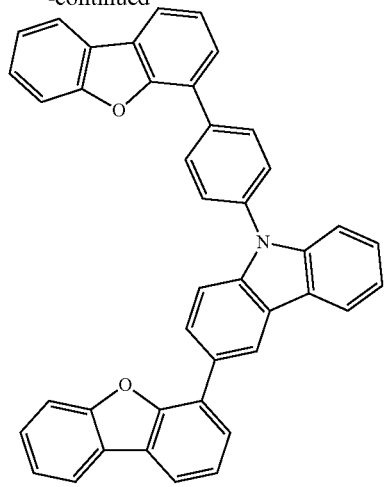

Under protective gas, 23.6 g (71 mmol) of 3-(dibenzofuran-4-yl)-9H-carbazole and 25 g (74 mmol) of 4-(4-bromophenyl)dibenzofuran, 8 g (84 mmol) of sodium tert-butoxide, 3.5 ml of tris-tert-butylphosphine (1 M in toluene) and 0.393 mg (1.7 mmol) palladium acetate are suspended in 300 ml of p-xylene. The reaction mixture is heated under reflux at 110° C. for 12 h. After cooling, the organic phase is removed, washed three times with 200 ml of water and then concentrated to dryness. The product is purified via column chromatography on silica gel with toluene/heptane (1:2). The residue is subjected to hot extraction with toluene, recrystallized from toluene and finally sublimed under high vacuum. HPLC purity is greater than 99.9%.

The yield is 33.7 g (658 mmol), 80% of theory, purity by $^1$H NMR about 94%.

In an analogous manner, the following compounds are prepared:

| | Reactant 1 | Reactant 2 |
|---|---|---|
| C1 | [carbazole-dibenzofuran structure] | [4-bromophenyl-6-phenyl-dibenzofuran structure] [1556069-46-5] |
| C2 | [carbazole-phenyl-dibenzofuran structure] | [4-(4-bromophenyl)dibenzofuran structure] [955959-84-9] |

-continued
C3 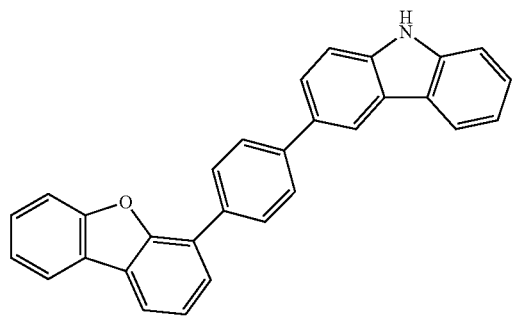 [SMILES: c1ccc2c(c1)[nH]c1ccc(-c3ccc(-c4cccc5c4oc4ccccc45)cc3)cc12] 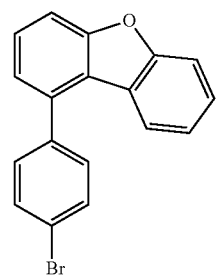
[17864-89-4]
C4 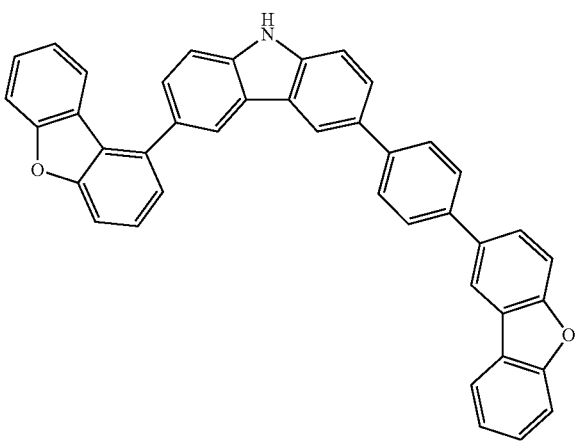 [SMILES: c1ccc2c(c1)oc1ccc(-c3ccc(-c4ccc5[nH]c6ccc(-c7cccc8oc9ccccc9c78)cc6c5c4)cc3)cc12] 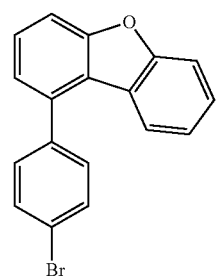
[1766416-89-4]
C5 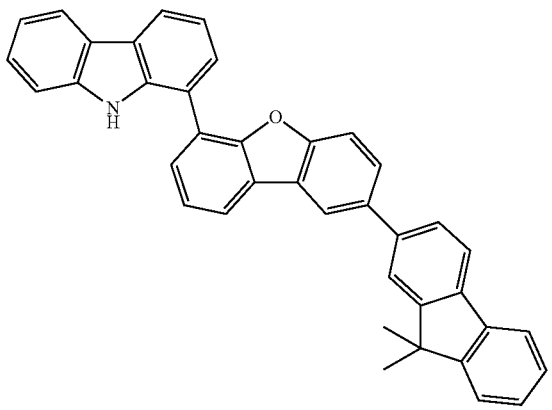 [SMILES: CC1(C)c2ccccc2-c2ccc(-c3ccc4oc5c(-c6cccc7c6[nH]c6ccccc67)cccc5c4c3)cc21] 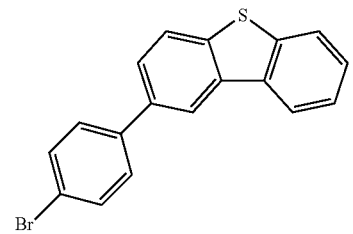
[1306786-03-7]
C6 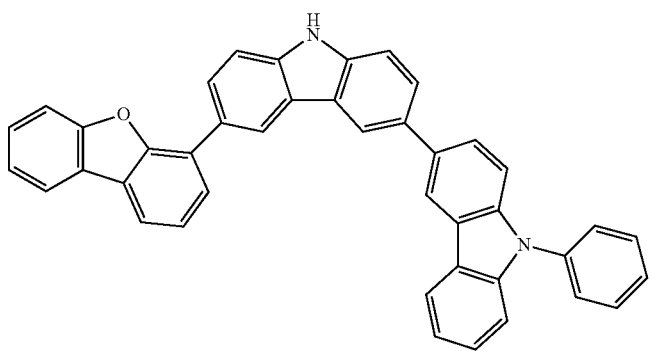 [SMILES: c1ccc(-n2c3ccccc3c3cc(-c4ccc5[nH]c6ccc(-c7cccc8c7oc7ccccc78)cc6c5c4)ccc32)cc1] 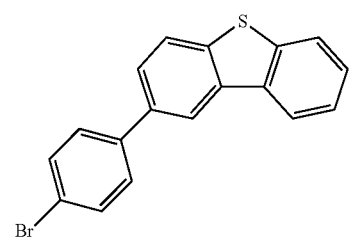
[1306786-03-7]

-continued
C7 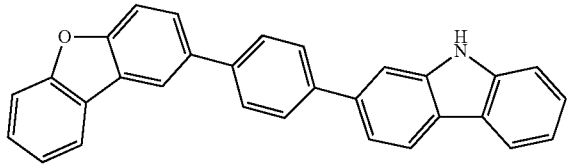 [SMILES: c1ccc2c(c1)[nH]c1cc(-c3ccc(-c4ccc5oc6ccccc6c5c4)cc3)ccc12] 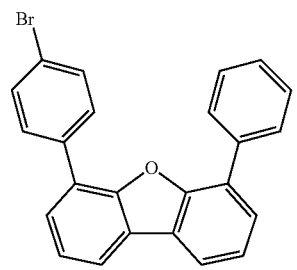
[1556069-46-5]
C8 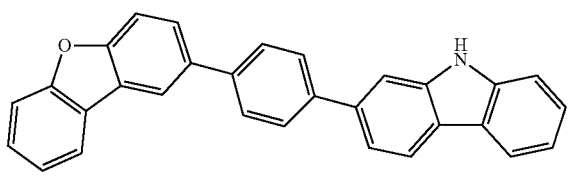 [SMILES: c1ccc2c(c1)[nH]c1cc(-c3ccc(-c4ccc5oc6ccccc6c5c4)cc3)ccc12] 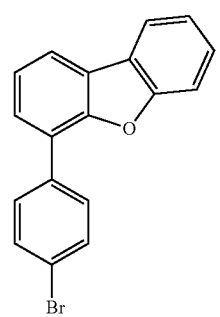
[955959-84-9]
C9 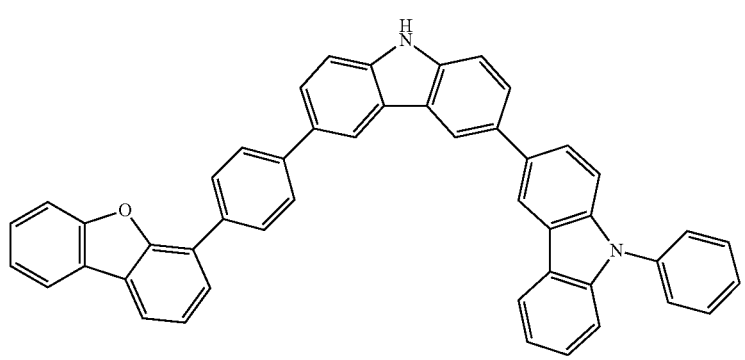 [SMILES: c1ccc(-n2c3ccccc3c3cc(-c4ccc5[nH]c6ccc(-c7ccc(-c8cccc9c8oc8ccccc89)cc7)cc6c5c4)ccc32)cc1] 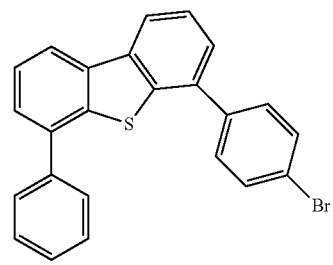
[1357081-21-0]
C10 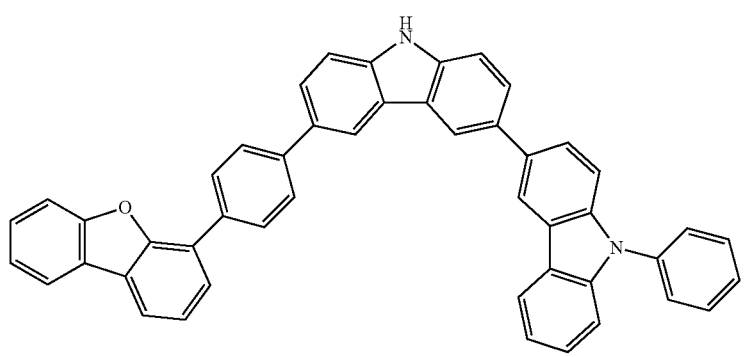 [SMILES: c1ccc(-n2c3ccccc3c3cc(-c4ccc5[nH]c6ccc(-c7ccc(-c8cccc9c8oc8ccccc89)cc7)cc6c5c4)ccc32)cc1] 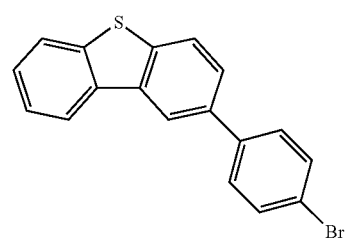
[1306786-03-7]

C11
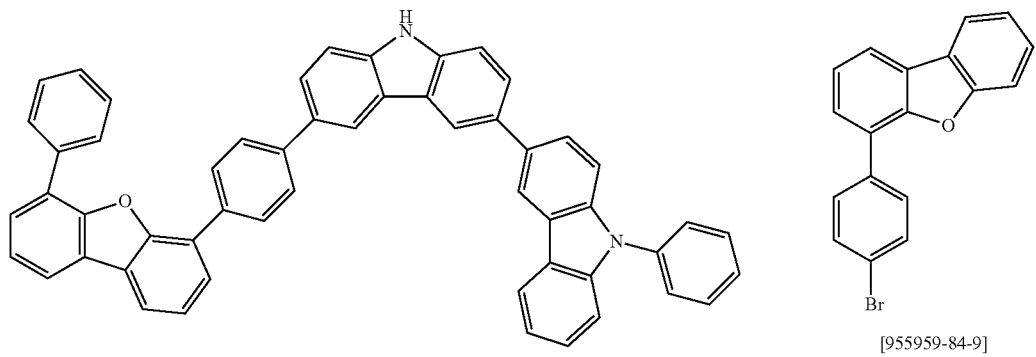
[955959-84-9]
C12
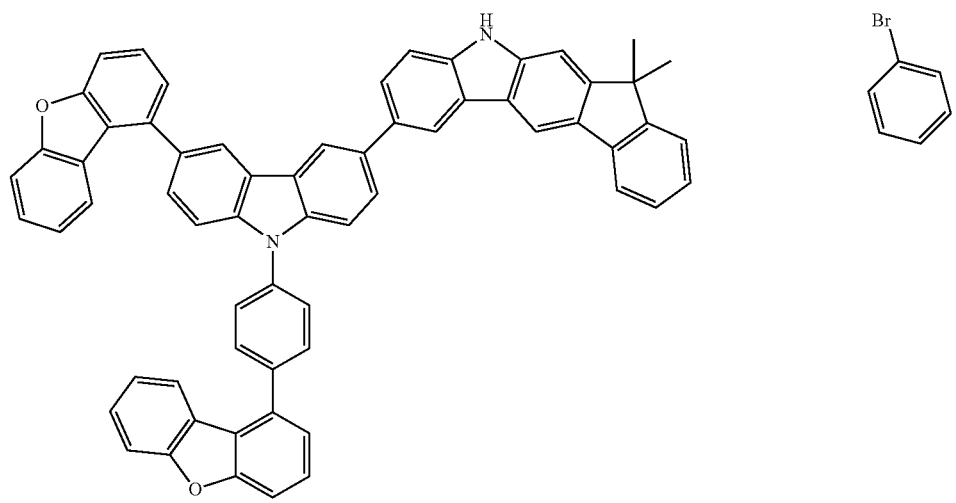
| | Product | Yield |
|---|---|---|
| C1 | 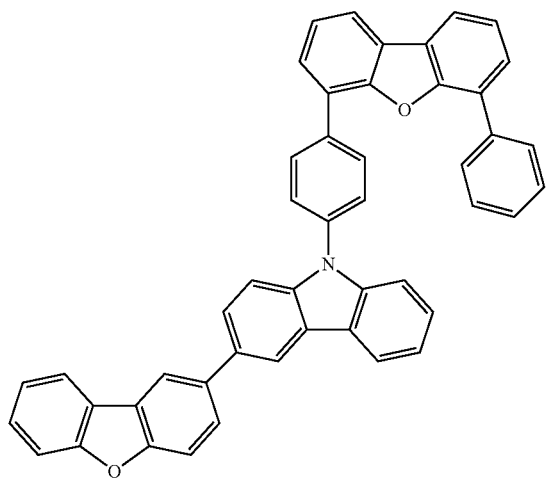 [SMILES: c1ccc(-c2cccc3c2oc2c(-c4ccc(-n5c6ccccc6c6cc(-c7ccc8oc9ccccc9c8c7)ccc65)cc4)cccc23)cc1] | 85% |

C2 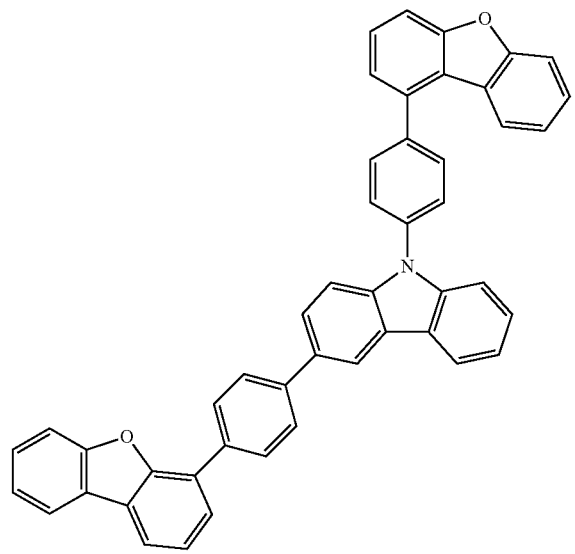 [SMILES: c1ccc2c(c1)oc1c(-c3ccc(-c4ccc5c(c4)c4ccccc4n5-c4ccc(-c5cccc6oc7ccccc7c56)cc4)cc3)cccc12] 80%
C3 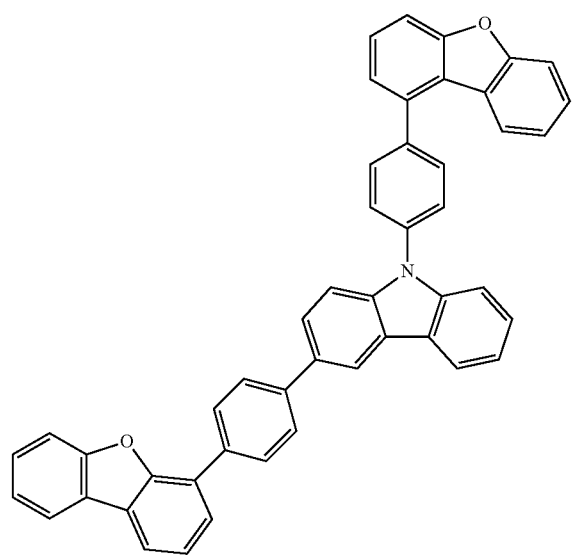 [SMILES: c1ccc2c(c1)oc1c(-c3ccc(-c4ccc5c(c4)c4ccccc4n5-c4ccc(-c5cccc6oc7ccccc7c56)cc4)cc3)cccc12] 79%

-continued
C4 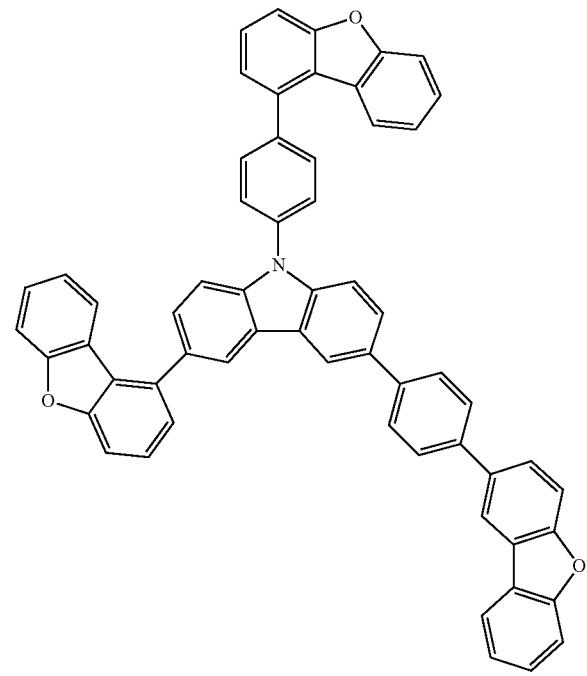 [SMILES: c1ccc2c(c1)oc1ccc(-c3ccc(-c4ccc5c(c4)c4cc(-c6cccc7oc8ccccc8c67)ccc4n5-c4ccc(-c5cccc6oc7ccccc7c56)cc4)cc3)cc12] 77%
C5 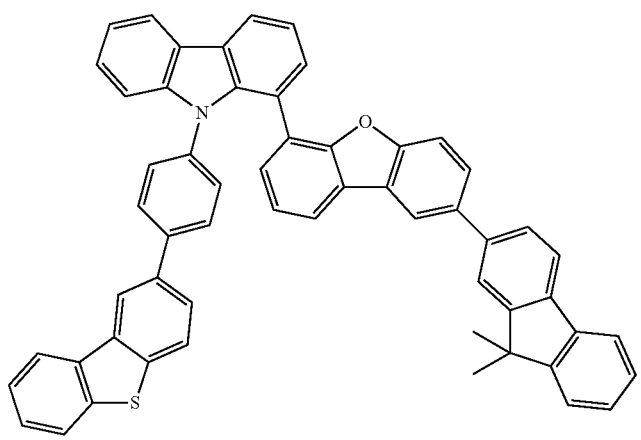 [SMILES: CC1(C)c2ccccc2-c2ccc(-c3ccc4oc5c(-c6cccc7c8ccccc8n(-c8ccc(-c9ccc%10sc%11ccccc%11c%10c9)cc8)c67)cccc5c4c3)cc21] 88%

| | | |
|---|---|---|
| C6 | 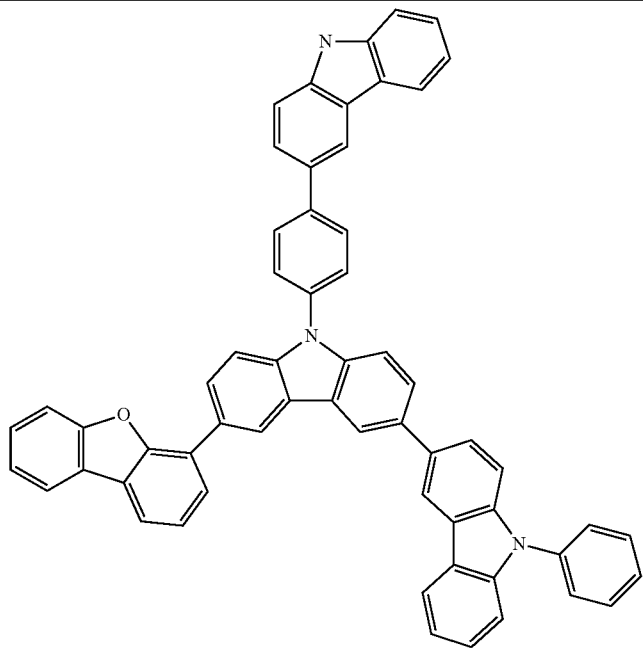 | 82% |
| C7 | 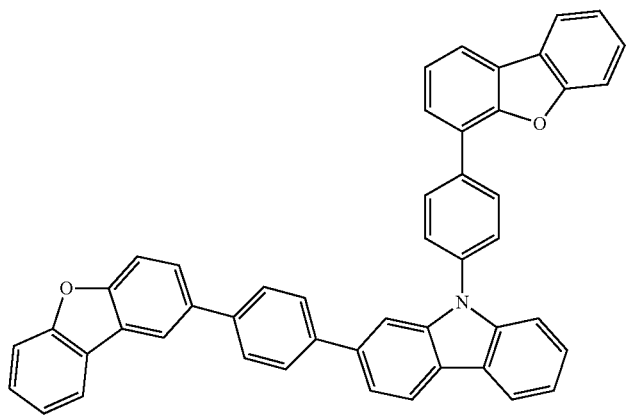 [SMILES: c1ccc2c(c1)oc1ccc(-c3ccc(-c4ccc5c6ccccc6n(-c6ccc(-c7cccc8c7oc7ccccc78)cc6)c5c4)cc3)cc12] | 81% |
| C8 | 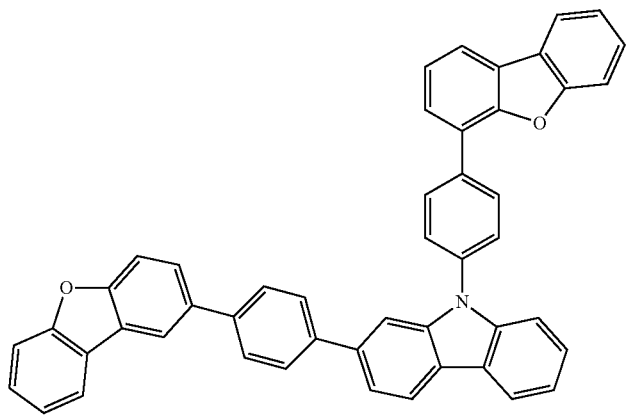 [SMILES: c1ccc2c(c1)oc1ccc(-c3ccc(-c4ccc5c6ccccc6n(-c6ccc(-c7cccc8c7oc7ccccc78)cc6)c5c4)cc3)cc12] | 75% |

C9 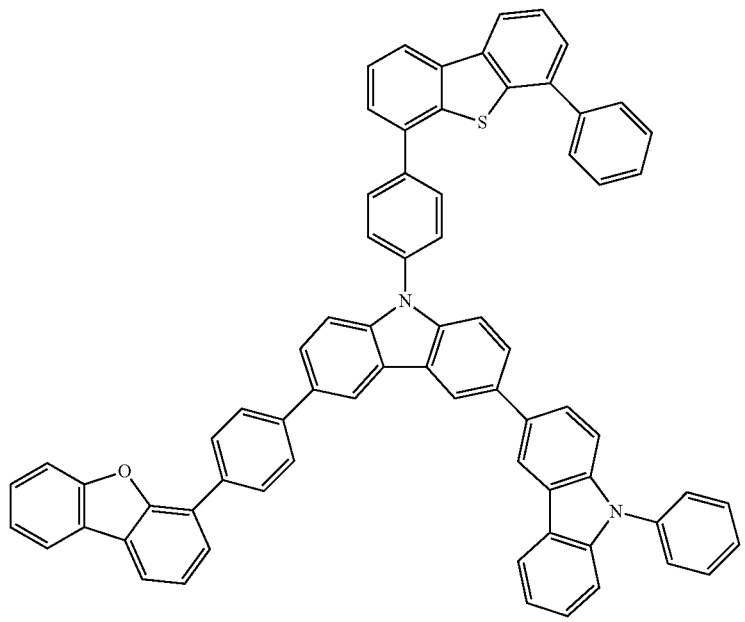 [SMILES: c1ccc(-c2cccc3c2sc2c(-c4ccc(-n5c6ccc(-c7ccc(-c8cccc9c8oc8ccccc89)cc7)cc6c6cc(-c7ccc8c(c7)c7ccccc7n8-c7ccccc7)ccc65)cc4)cccc23)cc1] 84%
C10 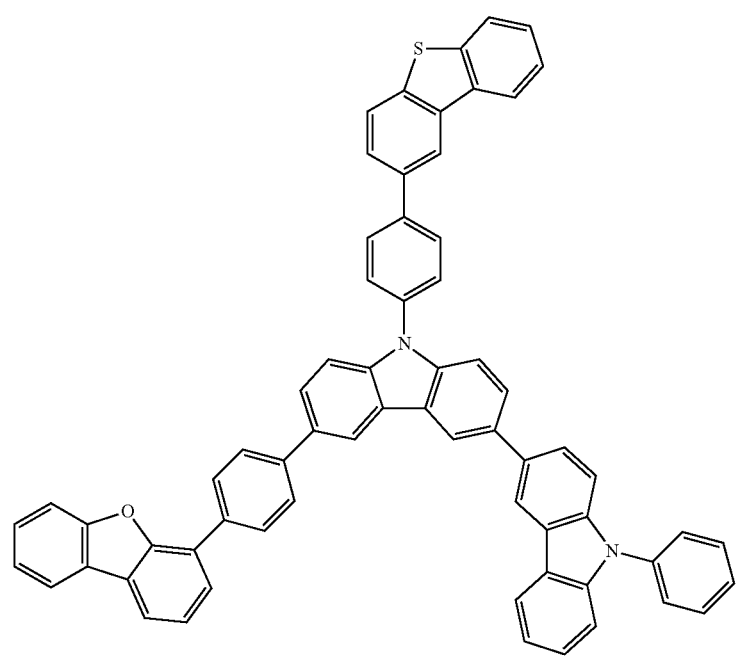 [SMILES: c1ccc(-n2c3ccccc3c3cc(-c4ccc5c(c4)c4cc(-c6ccc(-c7cccc8c7oc7ccccc78)cc6)ccc4n5-c4ccc(-c5ccc6sc7ccccc7c6c5)cc4)ccc32)cc1] 76%

-continued
C11 69%
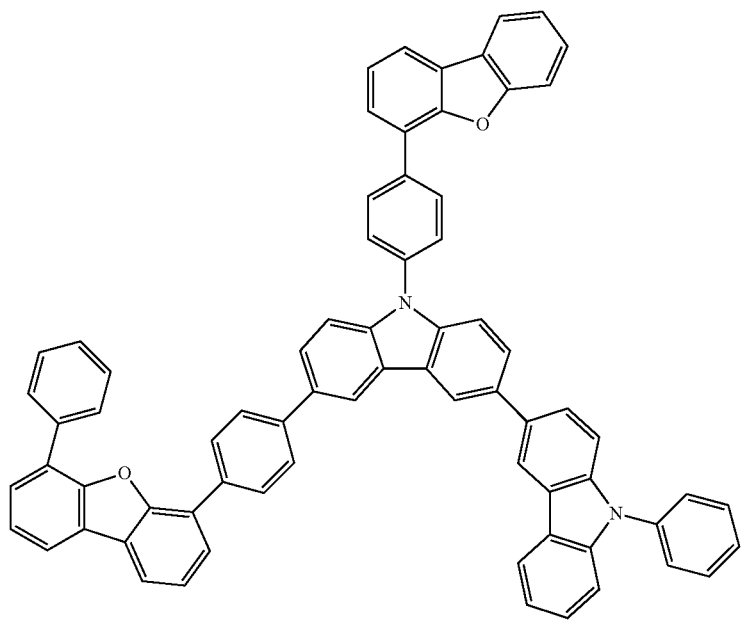 [SMILES: c1ccc(-c2cccc3c2oc2c(-c4ccc(-c5ccc6c(c5)c5cc(-c7ccc8c(c7)c7ccccc7n8-c7ccccc7)ccc5n6-c5ccc(-c6cccc7c6oc6ccccc67)cc5)cc4)cccc23)cc1]
C12 73%
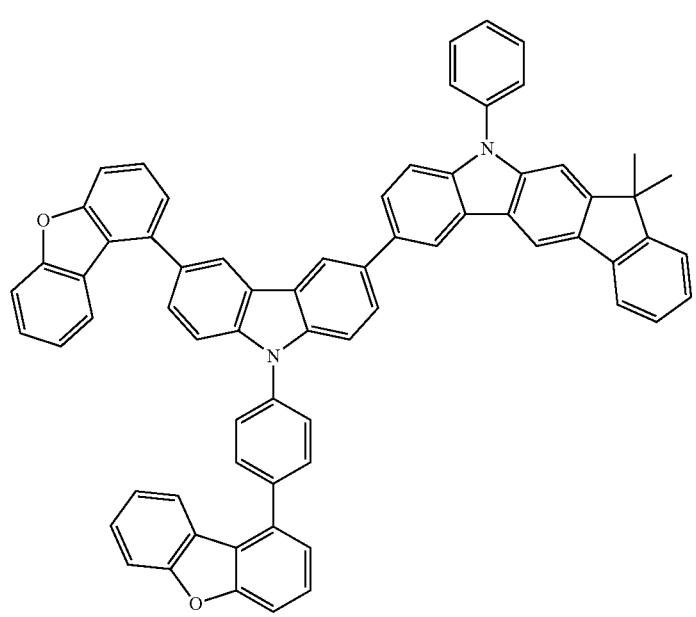 [SMILES: CC1(C)c2ccccc2-c2cc3c4cc(-c5ccc6c(c5)c5cc(-c7cccc8oc9ccccc9c78)ccc5n6-c5ccc(-c6cccc7oc8ccccc8c67)cc5)ccc4n(-c4ccccc4)c3cc21]

Analogously to the synthesis of A9, it is possible to prepare the following compounds:
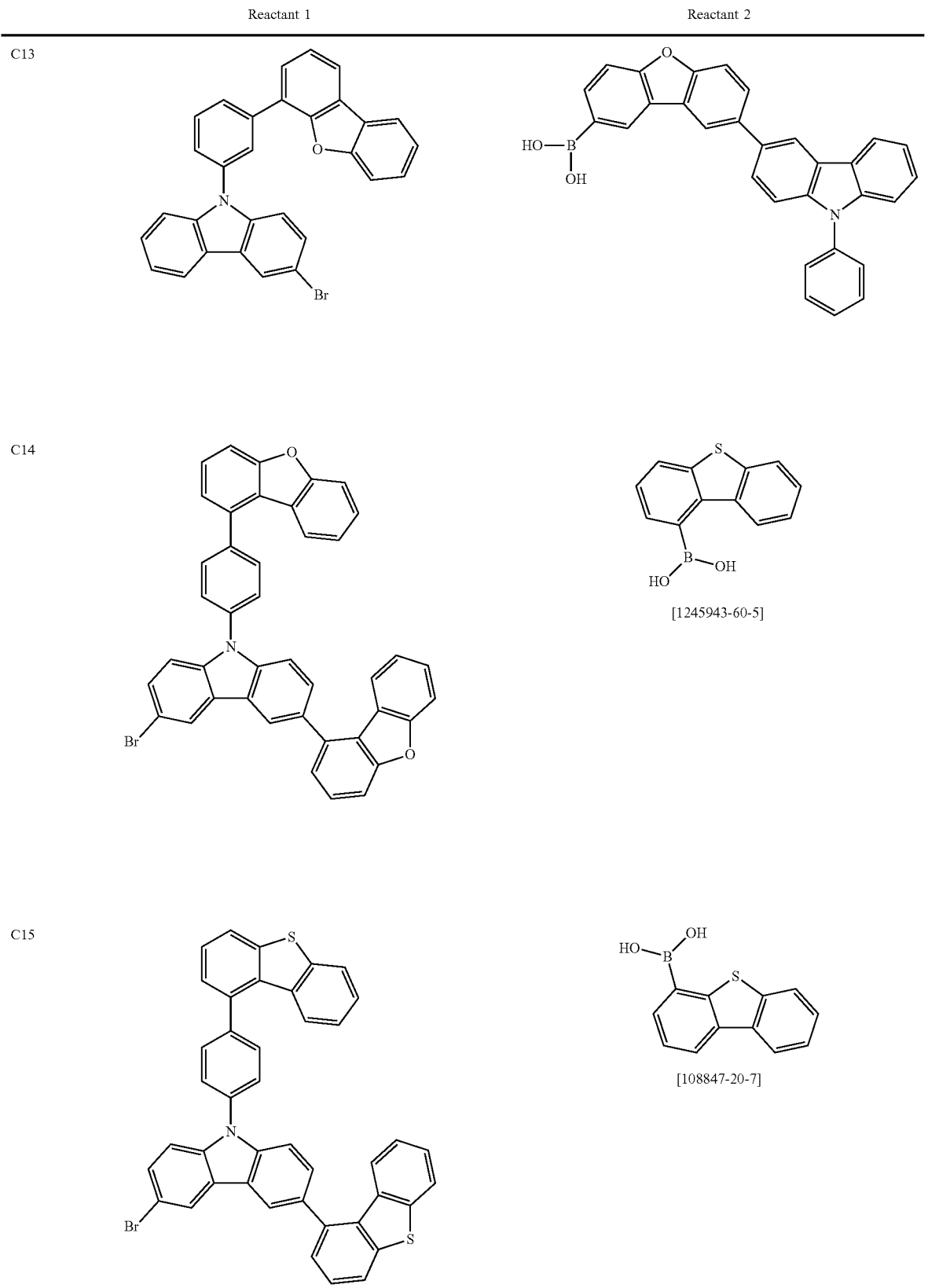

-continued
C16 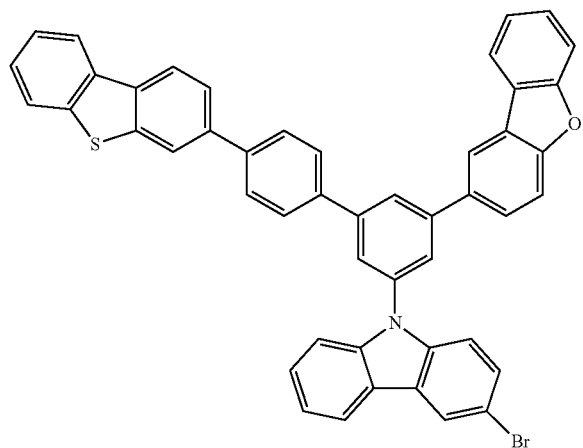 [SMILES: Brc1ccc2c(c1)c1ccccc1n2-c1cc(-c2ccc(-c3ccc4c(c3)sc3ccccc34)cc2)cc(-c2ccc3oc4ccccc4c3c2)c1] 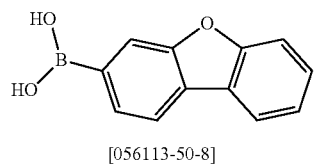 [SMILES: OB(O)c1ccc2c(c1)oc1ccccc12]
[056113-50-8]
C17 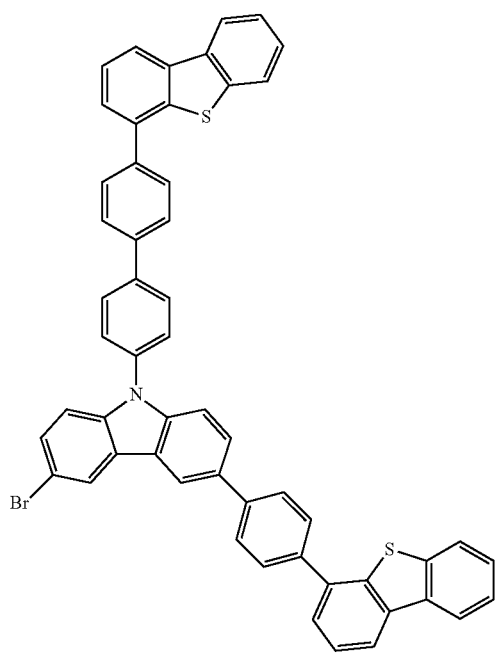 [SMILES: Brc1ccc2c(c1)c1cc(-c3ccc(-c4cccc5c4sc4ccccc45)cc3)ccc1n2-c1ccc(-c2ccc(-c3cccc4c3sc3ccccc34)cc2)cc1] 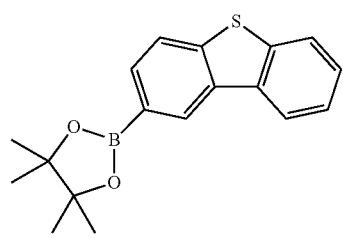
[890042-21-4]
C18 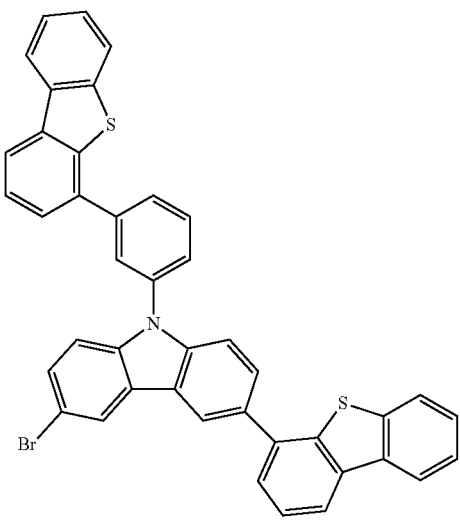 [SMILES: Brc1ccc2c(c1)c1cc(-c3cccc4c3sc3ccccc34)ccc1n2-c1cccc(-c2cccc3c2sc2ccccc23)c1] 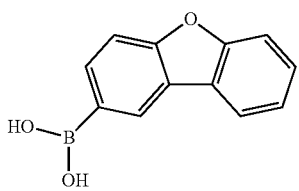
[402936-15-6]

-continued
| | | |
|---|---|---|
| C19 | 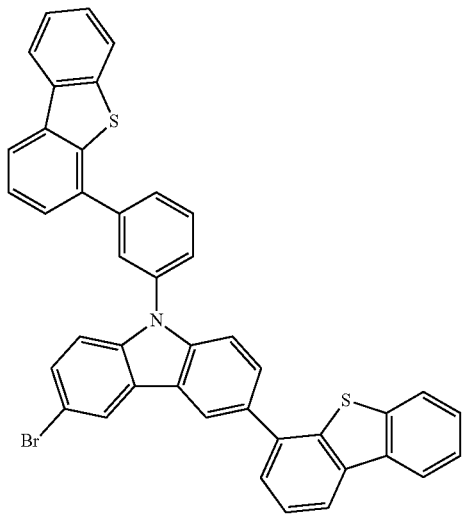 [SMILES: Brc1ccc2c(c1)c1cc(-c3cccc4c3sc3ccccc34)ccc1n2-c1cccc(-c2cccc3c2sc2ccccc23)c1] | 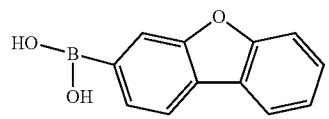
395087-89-5] |
| C20 | 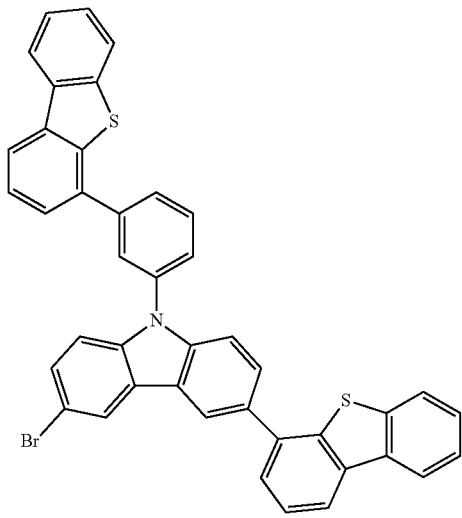 [SMILES: Brc1ccc2c(c1)c1cc(-c3cccc4c3sc3ccccc34)ccc1n2-c1cccc(-c2cccc3c2sc2ccccc23)c1] | 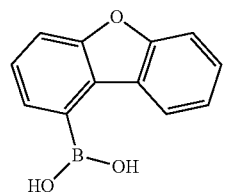
[162607-19-4] |
| C21 | 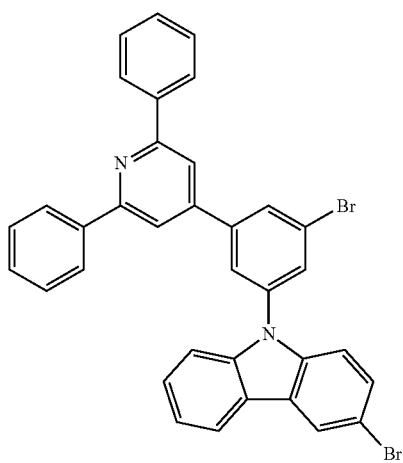 [SMILES: Brc1cc(-c2cc(-c3ccccc3)nc(-c3ccccc3)c2)cc(-n2c3ccccc3c3cc(Br)ccc32)c1] | 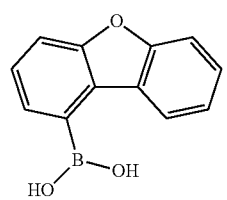
[162607-19-4] |

-continued
C22 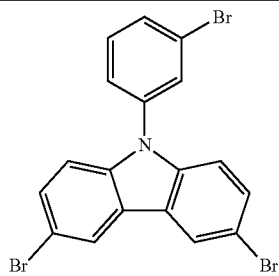
[085596-55-0]
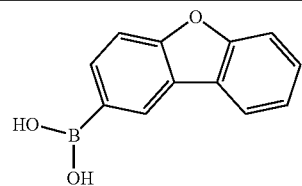
[402936-15-6]
C23 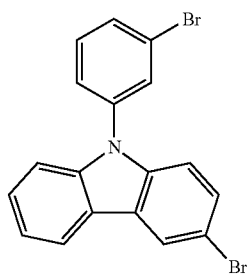
[1345415-06-5]
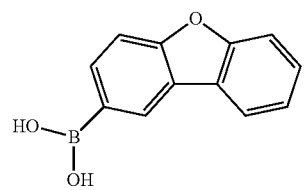
[402936-15-6]
C24 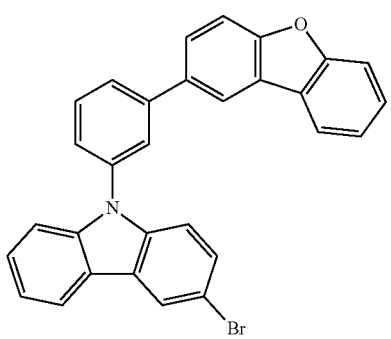
[1476799-03-7]
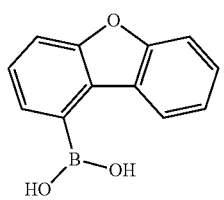
[162607-19-4]
C25 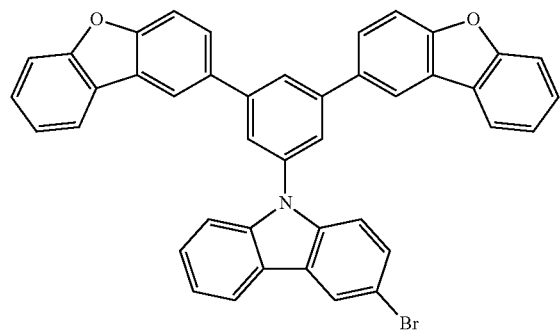 [SMILES: Brc1ccc2c(c1)c1ccccc1n2-c1cc(-c2ccc3oc4ccccc4c3c2)cc(-c2ccc3oc4ccccc4c3c2)c1]
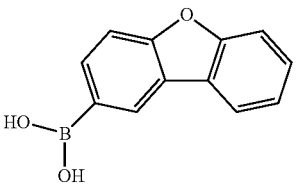
[402936-15-6]

| | | |
|---|---|---|
| C27 | 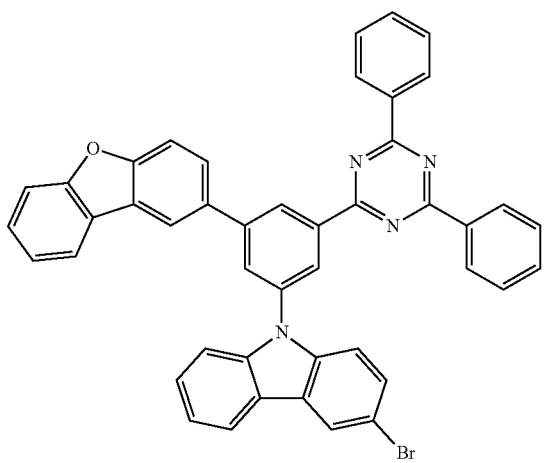 [SMILES: Brc1ccc2c(c1)c1ccccc1n2-c1cc(-c2ccc3oc4ccccc4c3c2)cc(-c2nc(-c3ccccc3)nc(-c3ccccc3)n2)c1] | 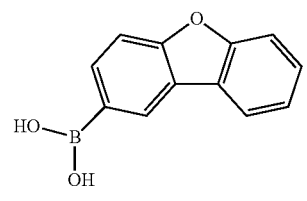
[402936-15-6] |
| | Product | Yield |
|---|---|---|
| C13 | 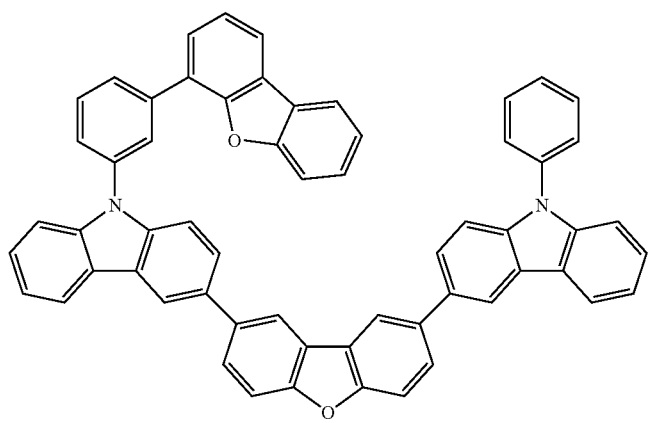 [SMILES: c1ccc(-n2c3ccccc3c3cc(-c4ccc5oc6ccc(-c7ccc8c(c7)c7ccccc7n8-c7cccc(-c8cccc9c8oc8ccccc89)c7)cc6c5c4)ccc32)cc1] | 71% |
| C14 | 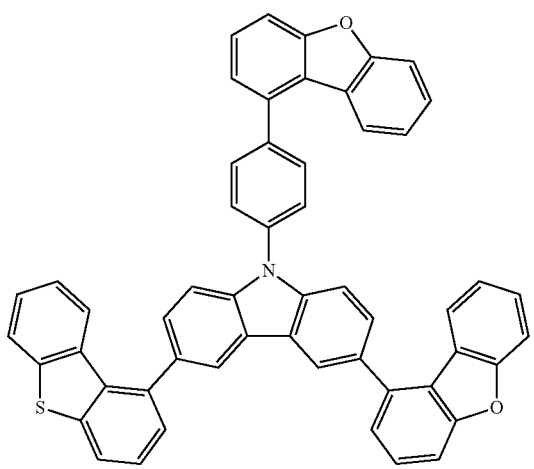 [SMILES: c1ccc2c(c1)oc1cccc(-c3ccc(-n4c5ccc(-c6cccc7oc8ccccc8c67)cc5c5cc(-c6cccc7sc8ccccc8c67)ccc54)cc3)c12] | 73% |

C15 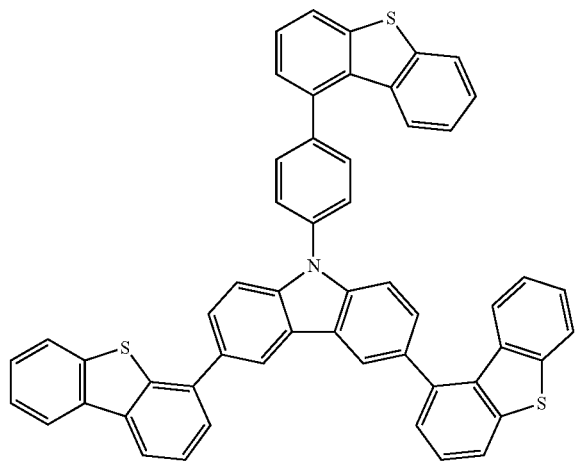 [SMILES: c1ccc2c(c1)sc1c(-c3ccc4c(c3)c3cc(-c5cccc6sc7ccccc7c56)ccc3n4-c3ccc(-c4cccc5sc6ccccc6c45)cc3)cccc12] 74%
C16 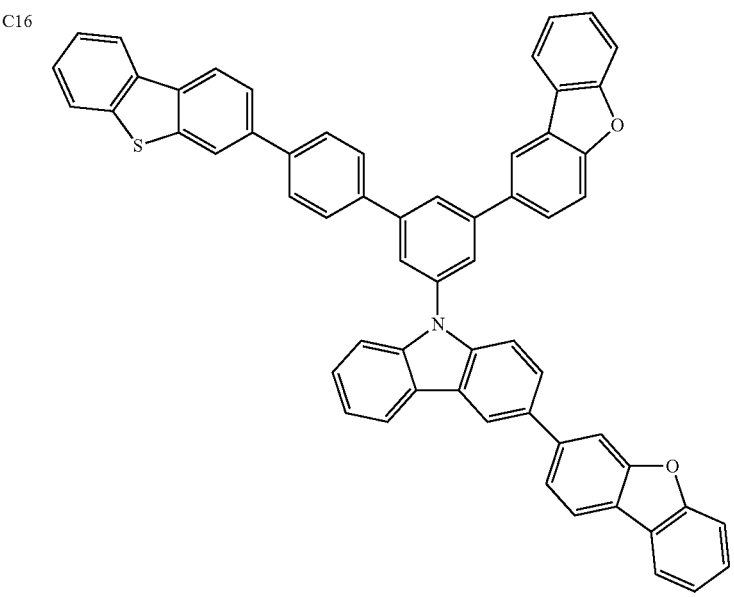 72%

| C17 | 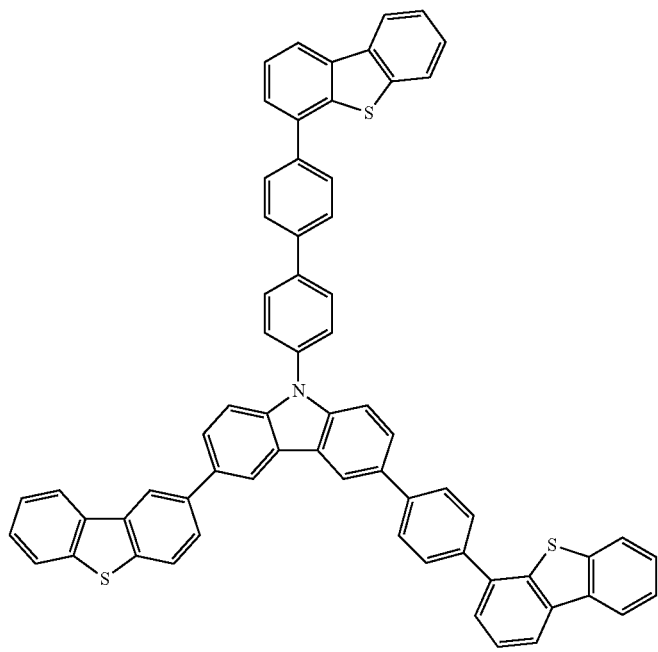 [SMILES: c1ccc2c(c1)sc1ccc(-c3ccc4c(c3)c3cc(-c5ccc(-c6cccc7c6sc6ccccc67)cc5)ccc3n4-c3ccc(-c4ccc(-c5cccc6c5sc5ccccc56)cc4)cc3)cc12] | 70% |
| C18 | 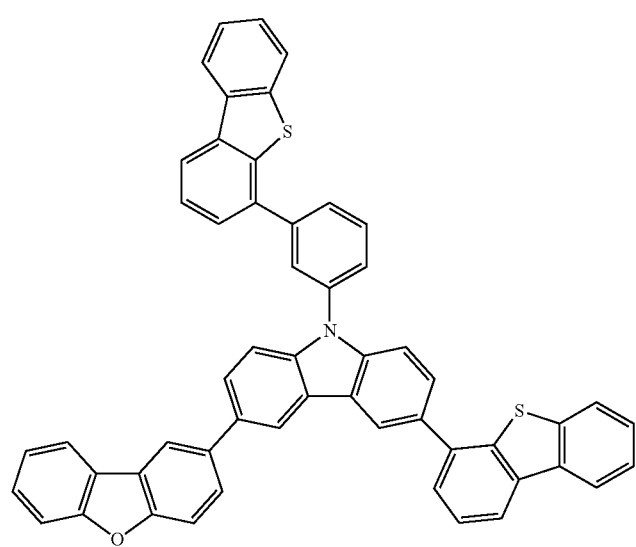 [SMILES: c1cc(-c2cccc3c2sc2ccccc23)cc(-n2c3ccc(-c4ccc5oc6ccccc6c5c4)cc3c3cc(-c4cccc5c4sc4ccccc45)ccc32)c1] | 65% |

C19 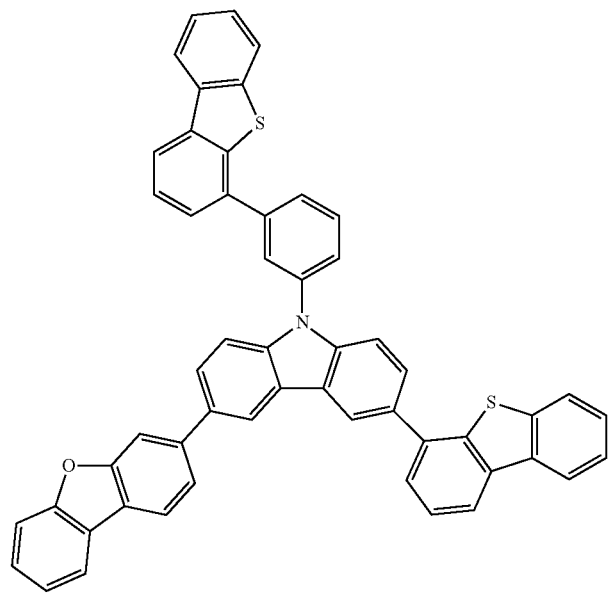 [SMILES: c1cc(-c2cccc3c2sc2ccccc23)cc(-n2c3ccc(-c4ccc5c(c4)oc4ccccc45)cc3c3cc(-c4cccc5c4sc4ccccc45)ccc32)c1] 72%
C20 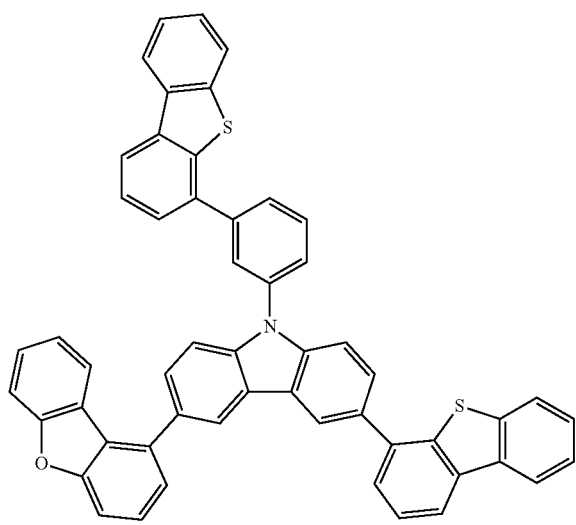 [SMILES: c1cc(-c2cccc3c2sc2ccccc23)cc(-n2c3ccc(-c4cccc5c4sc4ccccc45)cc3c3cc(-c4cccc5oc6ccccc6c45)ccc32)c1] 75%

-continued
| | | |
|---|---|---|
| C21 | 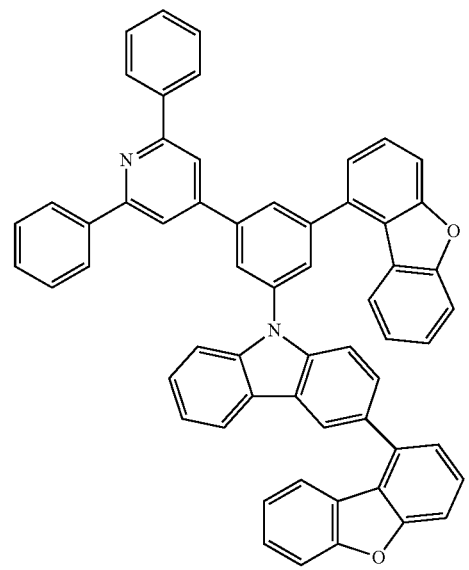 [SMILES: c1ccc(-c2cc(-c3cc(-c4cccc5oc6ccccc6c45)cc(-n4c5ccccc5c5cc(-c6cccc7oc8ccccc8c67)ccc54)c3)cc(-c3ccccc3)n2)cc1] | 78% |
| C22 | 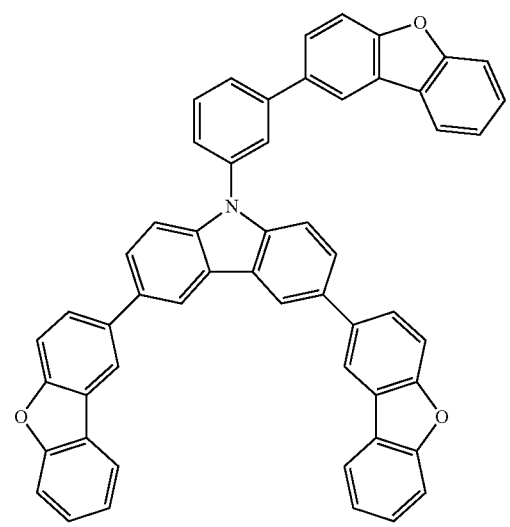 [SMILES: c1cc(-c2ccc3oc4ccccc4c3c2)cc(-n2c3ccc(-c4ccc5oc6ccccc6c5c4)cc3c3cc(-c4ccc5oc6ccccc6c5c4)ccc32)c1] | 81% |
| C23 | 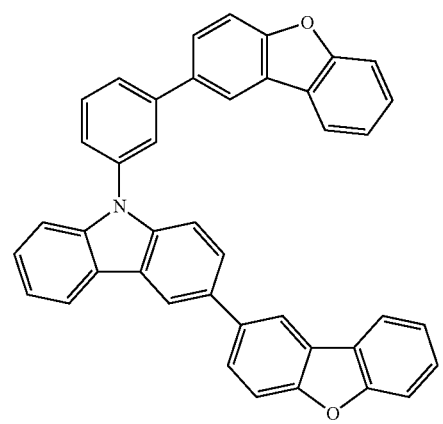 [SMILES: c1cc(-c2ccc3oc4ccccc4c3c2)cc(-n2c3ccccc3c3cc(-c4ccc5oc6ccccc6c5c4)ccc32)c1] | 82% |

-continued
C24 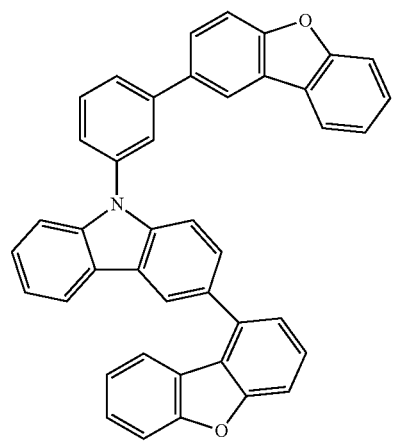 [SMILES: c1cc(-c2ccc3oc4ccccc4c3c2)cc(-n2c3ccccc3c3cc(-c4cccc5oc6ccccc6c45)ccc32)c1] 84%
C25 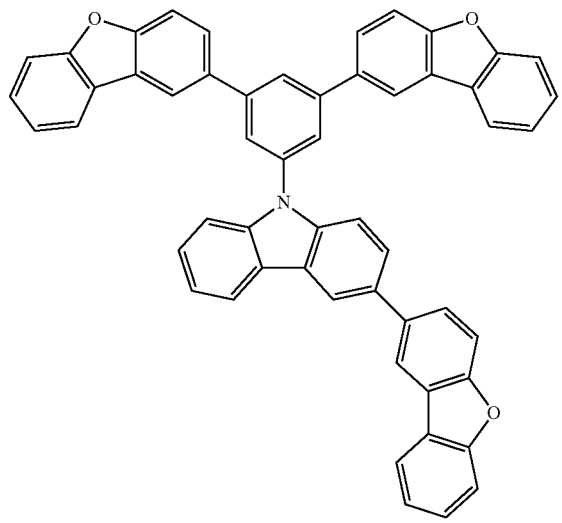 [SMILES: c1ccc2c(c1)oc1ccc(-c3cc(-c4ccc5oc6ccccc6c5c4)cc(-n4c5ccccc5c5cc(-c6ccc7oc8ccccc8c7c6)ccc54)c3)cc12] 81%
C27 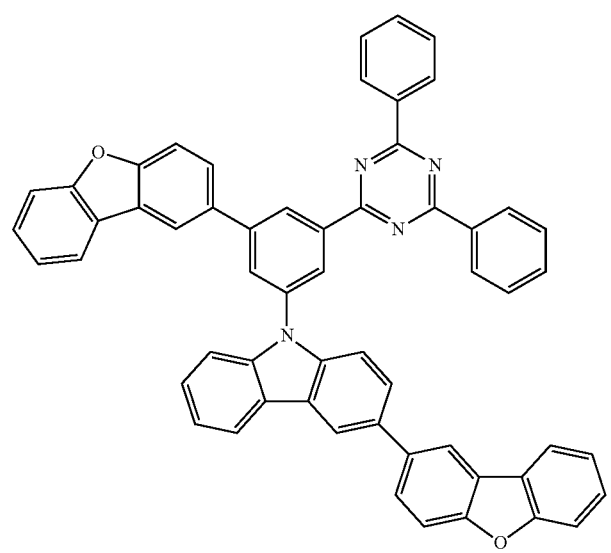 [SMILES: c1ccc(-c2nc(-c3ccccc3)nc(-c3cc(-c4ccc5oc6ccccc6c5c4)cc(-n4c5ccccc5c5cc(-c6ccc7oc8ccccc8c7c6)ccc54)c3)n2)cc1] 72%

Production of the OLEDs

OLEDs of the invention and OLEDs according to the prior art are produced by a general method according to WO 2004/058911, which is adapted to the circumstances described here (variation in layer thickness, materials).

In examples C1 to I10 which follow (see Tables 1 and 2), the data of various OLEDs are presented. Cleaned glass plaques (cleaning in laboratory glass washer, Merck Extran detergent) coated with structured ITO (indium tin oxide) of thickness 50 nm, for improved processing, are coated with 20 nm of PEDOT:PSS (poly(3,4-ethylenedioxythiophene) poly(styrenesulphonate), purchased as CLEVIOS™ P VP AI 4083 from Heraeus Precious Metals GmbH Deutschland, spun on from aqueous solution). These coated glass plaques form the substrates to which the OLEDs are applied.

The OLEDs basically have the following layer structure: substrate/optional hole injection layer (HIL)/hole transport layer (HTL)/optional interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as ST1:CBP:TER1 (55%:35%:10%) mean here that the material ST1 is present in the layer in a proportion by volume of 55%, CBP in a proportion of 35% and TER1 in a proportion of 10%. Analogously, the electron transport layer may also consist of a mixture of two materials.

The OLEDs are characterized in a standard manner. For this purpose, the electroluminescence spectra, the current efficiency (measured in cd/A) as a function of luminance, calculated from current-voltage-luminance characteristics (IUL characteristics) assuming Lambertian radiation characteristics, and the lifetime are measured. The electroluminescence spectra are determined at a luminance of 1000 cd/m$^2$, and the CIE 1931 x and y colour coordinates are calculated therefrom. The parameter U1000 in Table 2 refers to the voltage which is required for a luminance of 1000 cd/m$^2$. SE1000 denotes the current efficiency which is achieved at 1000 cd/m$^2$.

The lifetime LT is defined as the time after which the luminance drops from the starting luminance to a certain proportion L1 in the course of operation with constant current. A figure of L0; j0=4000 cd/m$^2$ and L1=80% in Table 2 means that the lifetime reported in the LT column corresponds to the time after which the starting luminance falls from 4000 cd/m$^2$ to 3200 cd/m$^2$. Analogously, L0; j0=20 mA/cm$^2$, L1=80% means that the starting luminance in the course of operation at 20 mA/cm$^2$ falls to 80% of its starting value after the time LT.

The values for the lifetime can be converted to a figure for other starting luminances with the aid of conversion formulae known to those skilled in the art. In this context, the lifetime for a starting luminance of 1000 cd/m$^2$ is a standard figure.

The data for the various OLEDs are collated in Table 2. Examples C1-C6 are comparative examples according to the prior art; examples I1-I10 show data of OLEDs comprising inventive materials.

Some of the examples are elucidated in detail hereinafter, in order to illustrate the advantages of the inventive compounds. However, it should be pointed out that this is merely a selection of the data shown in table 2. As can be inferred from the table, even when the compounds of the invention that have not been specifically detailed are used, distinct improvement over the prior art are achieved, in some cases in all parameters, but in some cases only an improvement in efficiency or voltage or lifetime is observed. However, improvement in one of the parameters mentioned is already a significant advance because various applications require optimization with regard to different parameters.

Through the use of compounds of the invention in the electron transport layer of OLEDs, it is thus possible to achieve distinct increases in terms of operating voltage, external quantum efficiency and hence in particular power efficiency as well. In addition, improved lifetimes are obtained in the case of phosphorescent dopants.

The use of compounds of the invention on the hole transport side of OLEDs thus gives significant improvements with regard to operating voltage, power efficiency, lifetime and processing complexity.

The materials of the invention, when used as matrix materials in phosphorescent OLEDs, give significant improvements over the prior art in all parameters, particularly with regard to lifetime and in some cases also in power efficiency.

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 90 nm | PA1:IC1:TEG1 (45%:45%:10%) 30 nm | ST2 10 nm | ST2:LiQ (50%:50%) 30 nm | — |
| C2 | SpA1 70 nm | HATCN 5 nm | SpMA1 90 nm | PA2:IC1:TEG1 (45%:45%:10%) 30 nm | ST2 10 nm | ST2:LiQ (50%:50%) 30 nm | — |
| C3 | SpA1 70 nm | HATCN 5 nm | SpMA1 90 nm | PA3:IC1:TEG1 (45%:45%:10%) 30 nm | ST2 10 nm | ST2:LiQ (50%:50%) 30 nm | — |
| C4 | SpA1 70 nm | HATCN 5 nm | SpMA1 90 nm | PA4:IC1:TEG1 (45%:45%:10%) 30 nm | ST2 10 nm | ST2:LiQ (50%:50%) 30 nm | — |
| C5 | SpA1 70 nm | HATCN 5 nm | SpMA1 90 nm | PA5:IC1:TEG1 (45%:45%:10%) 30 nm | ST2 10 nm | ST2:LiQ (50%:50%) 30 nm | — |
| C6 | SpA1 70 nm | HATCN 5 nm | SpMA1 90 nm | PA6:IC1:TEG1 (45%:45%:10%) 30 nm | ST2 10 nm | ST2:LiQ (50%:50%) 30 nm | — |

TABLE 1-continued

Structure of the OLEDs

| Ex. | HTL thickness | IL thickness | EBL thickness | EML thickness | HBL thickness | ETL thickness | EIL thickness |
|---|---|---|---|---|---|---|---|
| C7 | SpA1 70 nm | HATCN 5 nm | SpMA1 90 nm | PA7:IC1:TEG1 (45%:45%:10%) 30 nm | ST2 10 nm | ST2:LiQ (50%:50%) 30 nm | — |
| I1 | SpA1 70 nm | HATCN 5 nm | SpMA1 90 nm | EG1:IC1:TEG1 (45%:45%:10%) 30 nm | ST2 10 nm | ST2:LiQ (50%:50%) 30 nm | — |
| I2 | SpA1 70 nm | HATCN 5 nm | SpMA1 90 nm | EG2:IC1:TEG1 (45%:45%:10%) 30 nm | ST2 10 nm | ST2:LiQ (50%:50%) 30 nm | — |
| I3 | SpA1 70 nm | HATCN 5 nm | SpMA1 90 nm | EG3:IC1:TEG1 (45%:45%:10%) 30 nm | ST2 10 nm | ST2:LiQ (50%:50%) 30 nm | — |
| I4 | SpA1 70 nm | HATCN 5 nm | SpMA1 90 nm | EG4:IC1:TEG1 (45%:45%:10%) 30 nm | ST2 10 nm | ST2:LiQ (50%:50%) 30 nm | — |
| I1-1 | SpA1 90 nm | HATCN 5 nm | SpMA1 130 nm | EG1:IC1:TER1 (32%:60%:8%) 30 nm | — | ST2:LiQ (50%:50%) 40 nm | — |
| I5 | SpA1 70 nm | HATCN 5 nm | SpMA1 90 nm | EG5:IC1:TEG1 (45%:45%:10%) 30 nm | ST2 10 nm | ST2:LiQ (50%:50%) 30 nm | — |
| I7 | SpA1 70 nm | HATCN 5 nm | SpMA1 90 nm | EG7:IC1:TEG1 (45%:45%:10%) 30 nm | ST2 10 nm | ST2:LiQ (50%:50%) 30 nm | — |
| I8 | SpA1 70 nm | HATCN 5 nm | SpMA1 90 nm | EG8:IC1:TEG1 (45%:45%:10%) 30 nm | ST2 10 nm | ST2:LiQ (50%:50%) 30 nm | — |
| I9 | SpA1 70 nm | HATCN 5 nm | SpMA1 90 nm | EG9:IC1:TEG1 (45%:45%:10%) 30 nm | ST2 10 nm | ST2:LiQ (50%:50%) 30 nm | — |
| I10 | HATCN 5 nm | SpMA1 70 nm | SpMA2 15 nm | EG8:L1:TEY1 (45%:45%:10%) 25 nm | — | ST1 45 nm | LiQ 3 nm |

TABLE 2

Data of the OLEDs

| Ex. | U1000 (V) | CE1000 (cd/A) | CIE x/y at 1000 cd/m² | $L_0; j_0$ | L1 % | LT (h) |
|---|---|---|---|---|---|---|
| C1 | 3.9 | 55 | 0.33/0.63 | 20 mA/cm² | 80 | 290 |
| C2 | 3.6 | 57 | 0.33/0.63 | 20 mA/cm² | 80 | 250 |
| C3 | 3.9 | 55 | 0.33/0.63 | 20 mA/cm² | 80 | 230 |
| C4 | 4.1 | 54 | 0.32/0.63 | 20 mA/cm² | 80 | 200 |
| C5 | 3.8 | 52 | 0.33/0.63 | 20 mA/cm² | 80 | 150 |
| C6 | 3.6 | 55 | 0.33/0.63 | 20 mA/cm² | 80 | 190 |
| C7 | 3.5 | 57 | 0.33/0.63 | 20 mA/cm² | 80 | 300 |
| I1 | 3.5 | 60 | 0.33/0.62 | 20 mA/cm² | 80 | 350 |
| I2 | 3.8 | 58 | 0.33/0.62 | 20 mA/cm² | 80 | 280 |
| I3 | 4.1 | 55 | 0.33/0.63 | 20 mA/cm² | 80 | 230 |
| I4 | 3.7 | 54 | 0.32/0.63 | 20 mA/cm² | 80 | 230 |
| E1-1 | 4.5 | 11.5 | 0.67/0.34 | 4000 cd/m² | 80 | 390 |
| I5 | 3.6 | 58 | 0.33/0.63 | 20 mA/cm² | 80 | 350 |
| I7 | 3.5 | 57 | 0.33/0.63 | 20 mA/cm² | 80 | 340 |
| I8 | 3.7 | 59 | 0.33/0.63 | 20 mA/cm² | 80 | 380 |
| I9 | 3.6 | 58 | 0.33/0.63 | 20 mA/cm² | 80 | 370 |
| I10 | 30 | 77 | 0.44/0.55 | 50 mA/cm² | 90 | 75 |

TABLE 3

Structural formulae of the materials for the OLEDs

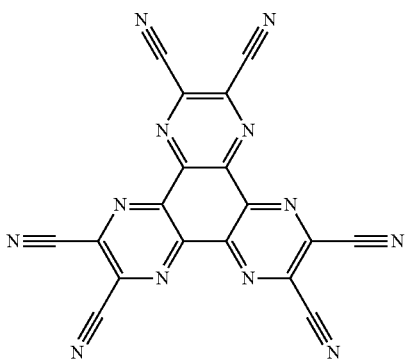 [SMILES: N#Cc1nc2c3nc(C#N)c(C#N)nc3c3nc(C#N)c(C#N)nc3c2nc1C#N]

HATCN

TABLE 3-continued
Structural formulae of the materials for the OLEDs
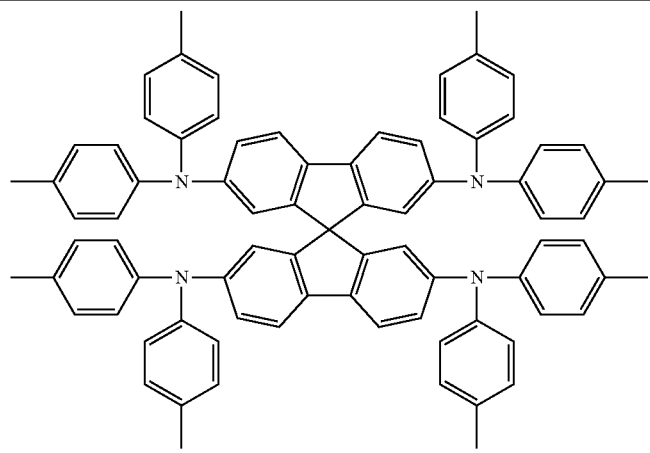
SpA1
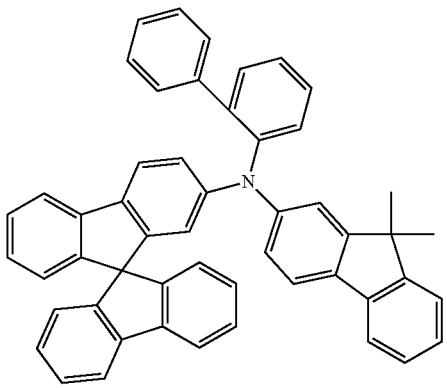 [SMILES: CC1(C)c2ccccc2-c2ccc(N(c3ccc4c(c3)C3(c5ccccc5-c5ccccc53)c3ccccc3-4)c3ccccc3-c3ccccc3)cc21]
SpMA1
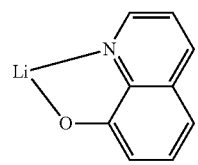
LiQ
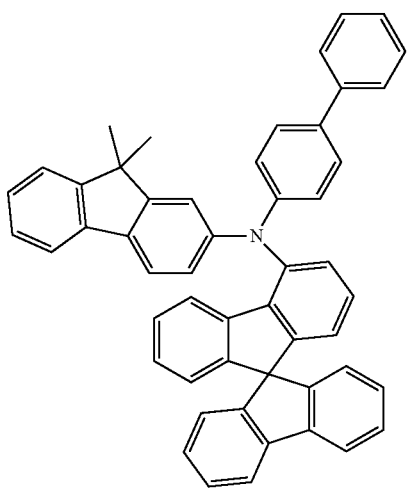 [SMILES: CC1(C)c2ccccc2-c2ccc(N(c3ccc(-c4ccccc4)cc3)c3cccc4c3-c3ccccc3C43c4ccccc4-c4ccccc43)cc21]

TABLE 3-continued
Structural formulae of the materials for the OLEDs
SpMA2
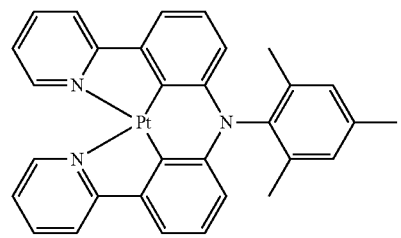
TER1
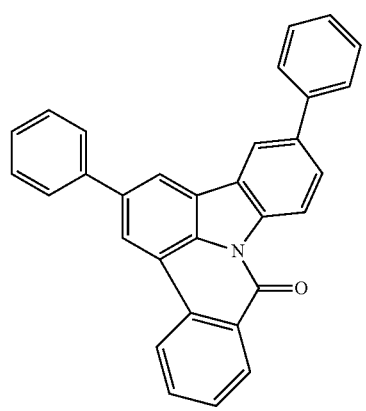 [SMILES: O=c1c2ccccc2c2cc(-c3ccccc3)cc3c4cc(-c5ccccc5)ccc4n1c23]
L1
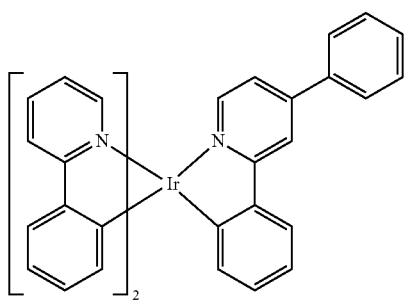
TEY1
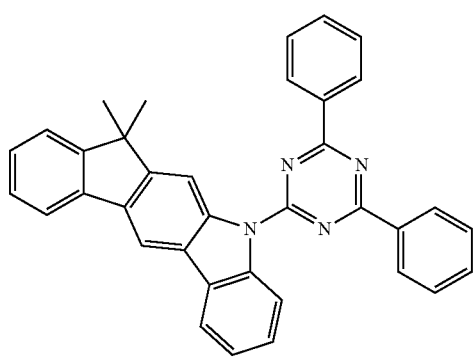 [SMILES: CC1(C)c2ccccc2-c2cc3c4ccccc4n(-c4nc(-c5ccccc5)nc(-c5ccccc5)n4)c3cc21]
IC1

TABLE 3-continued
Structural formulae of the materials for the OLEDs
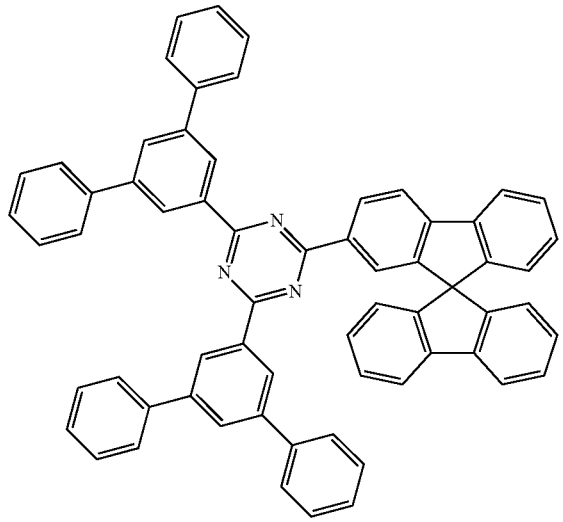 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ST2
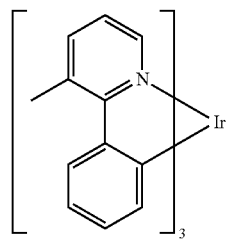
TEG1
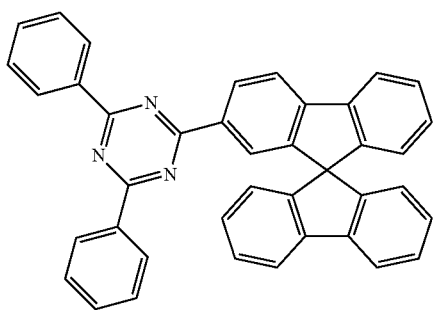 [SMILES: c1ccc(-c2nc(-c3ccccc3)nc(-c3ccc4c(c3)C3(c5ccccc5-c5ccccc53)c3ccccc3-4)n2)cc1]
ST1

TABLE 3-continued
Structural formulae of the materials for the OLEDs
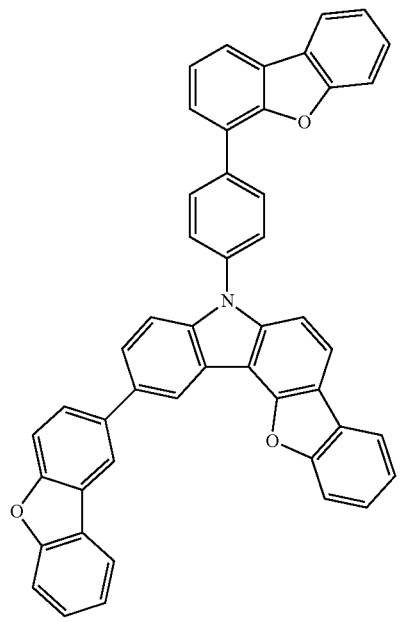 [SMILES: c1ccc2c(c1)oc1ccc(-c3ccc4c(c3)c3c5oc6ccccc6c5ccc3n4-c3ccc(-c4cccc5c4oc4ccccc45)cc3)cc12]
PA1
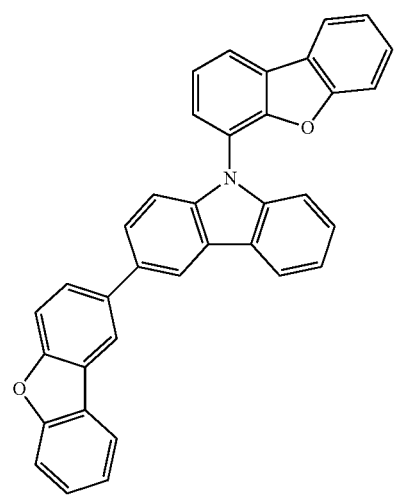 [SMILES: c1ccc2c(c1)oc1ccc(-c3ccc4c(c3)c3ccccc3n4-c3cccc4c3oc3ccccc34)cc12]
PA2

TABLE 3-continued
Structural formulae of the materials for the OLEDs
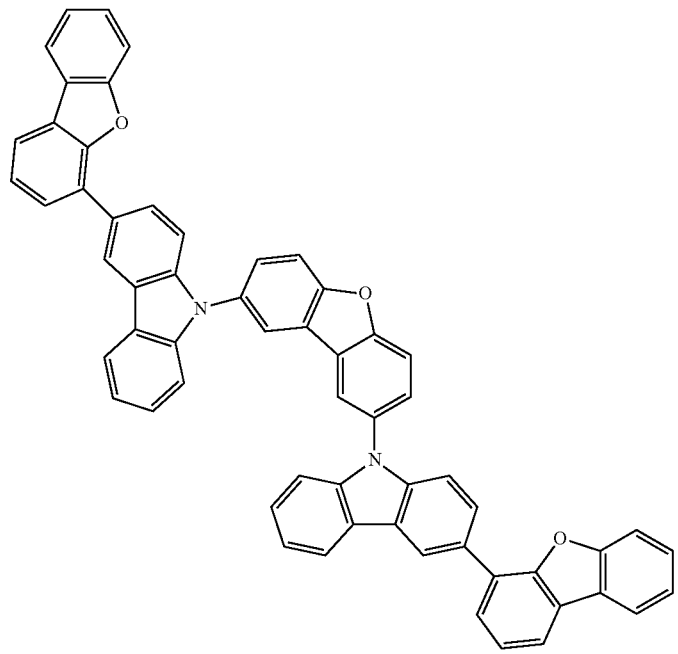 [SMILES: c1ccc2c(c1)oc1c(-c3ccc4c(c3)c3ccccc3n4-c3ccc4oc5ccc(-n6c7ccccc7c7cc(-c8cccc9c8oc8ccccc89)ccc76)cc5c4c3)cccc12]
PA3
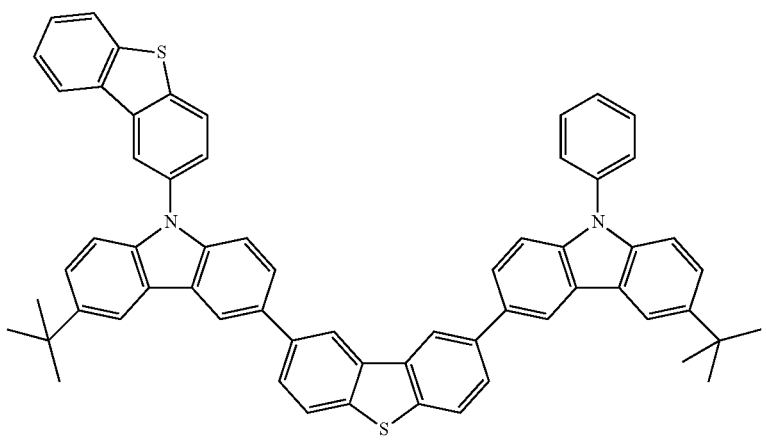 [SMILES: CC(C)(C)c1ccc2c(c1)c1cc(-c3ccc4sc5ccc(-c6ccc7c(c6)c6cc(C(C)(C)C)ccc6n7-c6ccc7sc8ccccc8c7c6)cc5c4c3)ccc1n2-c1ccccc1]
PA4

TABLE 3-continued
Structural formulae of the materials for the OLEDs
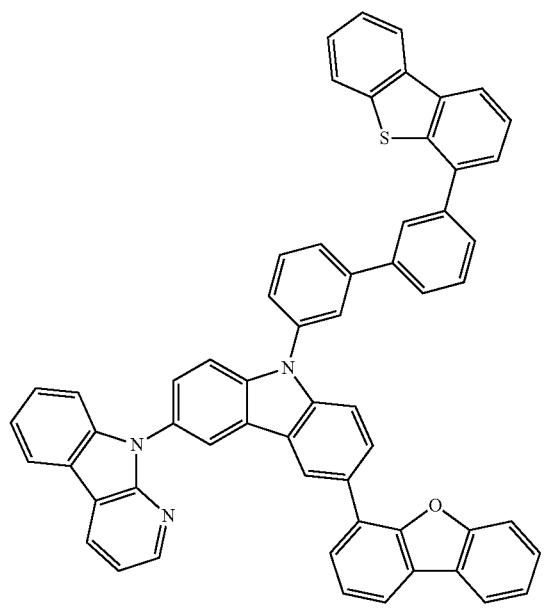 [SMILES: c1cc(-c2cccc(-n3c4ccc(-c5cccc6c5oc5ccccc56)cc4c4cc(-n5c6ccccc6c6cccnc65)ccc43)c2)cc(-c2cccc3c2sc2ccccc23)c1]
PA5
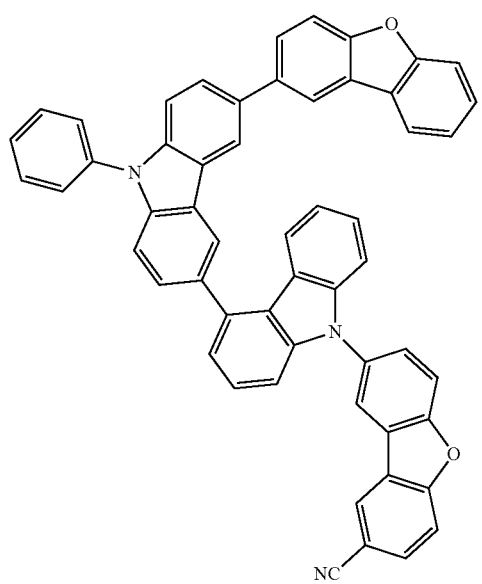 [SMILES: N#Cc1ccc2oc3ccc(-n4c5ccccc5c5c(-c6ccc7c(c6)c6cc(-c8ccc9oc%10ccccc%10c9c8)ccc6n7-c6ccccc6)cccc54)cc3c2c1]
PA6

TABLE 3-continued
Structural formulae of the materials for the OLEDs
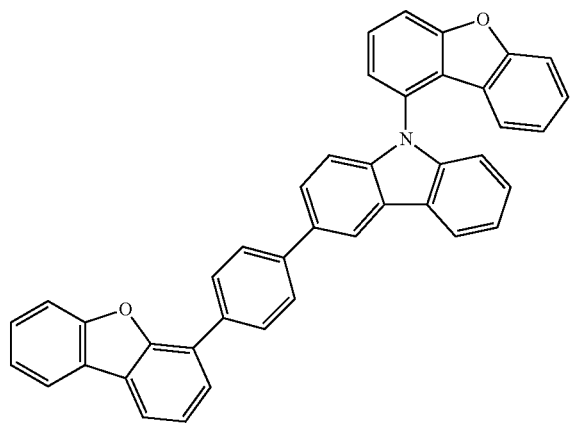 [SMILES: c1ccc2c(c1)oc1c(-c3ccc(-c4ccc5c(c4)c4ccccc4n5-c4cccc5oc6ccccc6c45)cc3)cccc12]
PA7
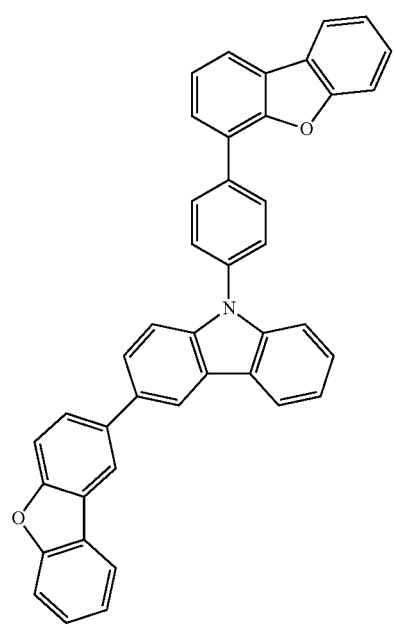 [SMILES: c1ccc2c(c1)oc1ccc(-c3ccc4c(c3)c3ccccc3n4-c3ccc(-c4cccc5c4oc4ccccc45)cc3)cc12]
EG1

229
230
TABLE 3-continued
Structural formulae of the materials for the OLEDs
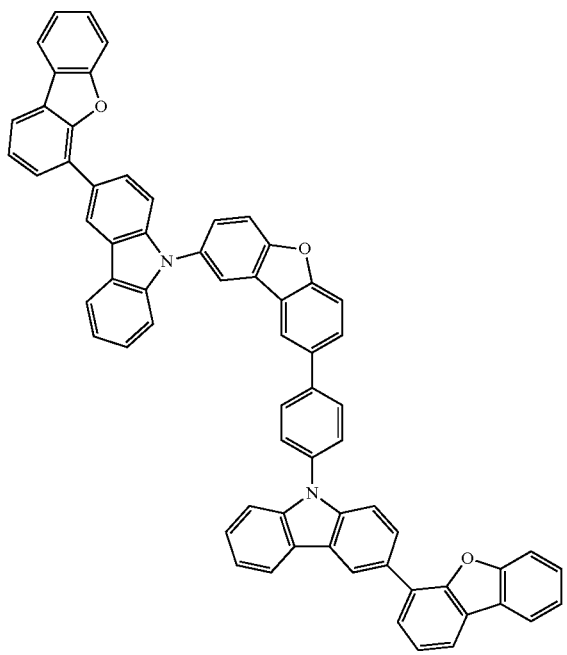 [SMILES: c1ccc2c(c1)oc1c(-c3ccc4c(c3)c3ccccc3n4-c3ccc(-c4ccc5oc6ccc(-n7c8ccccc8c8cc(-c9cccc%10c9oc9ccccc9%10)ccc87)cc6c5c4)cc3)cccc12]
EG2
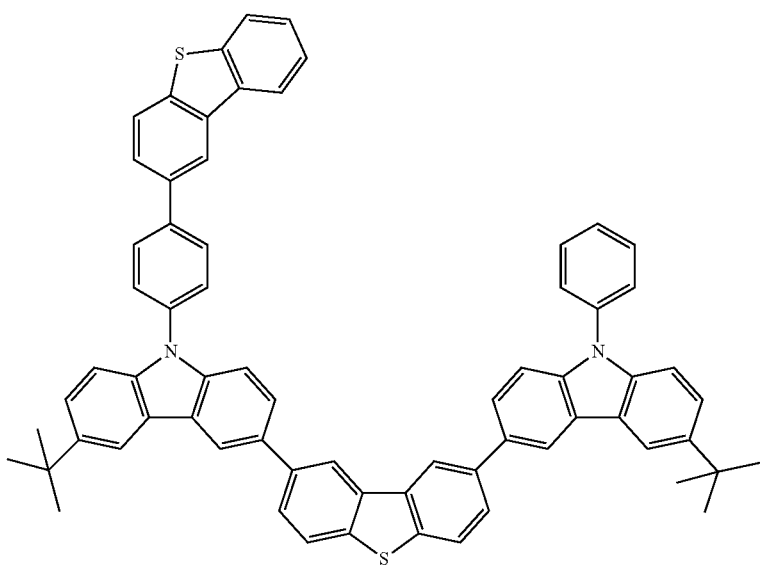 [SMILES: CC(C)(C)c1ccc2c(c1)c1cc(-c3ccc4sc5ccc(-c6ccc7c(c6)c6cc(C(C)(C)C)ccc6n7-c6ccc(-c7ccc8sc9ccccc9c8c7)cc6)cc5c4c3)ccc1n2-c1ccccc1]
EG3

TABLE 3-continued
Structural formulae of the materials for the OLEDs
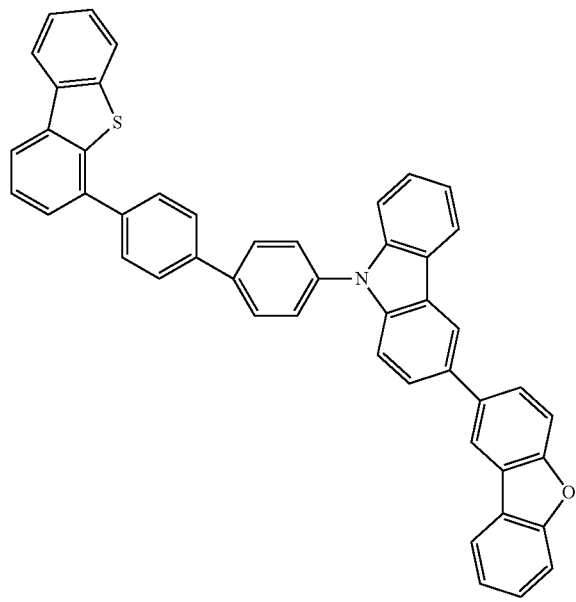 [SMILES: c1ccc2c(c1)oc1ccc(-c3ccc4c(c3)c3ccccc3n4-c3ccc(-c4ccc(-c5cccc6c5sc5ccccc56)cc4)cc3)cc12]
EG4
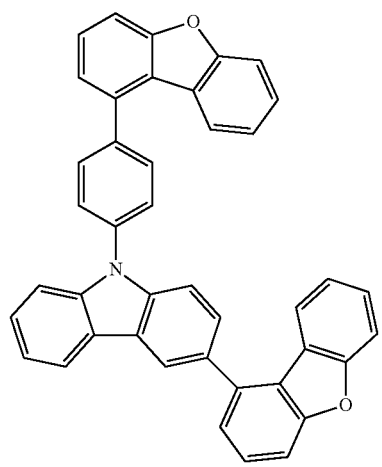 [SMILES: c1ccc2c(c1)oc1cccc(-c3ccc(-n4c5ccccc5c5cc(-c6cccc7oc8ccccc8c67)ccc54)cc3)c12]
EG5
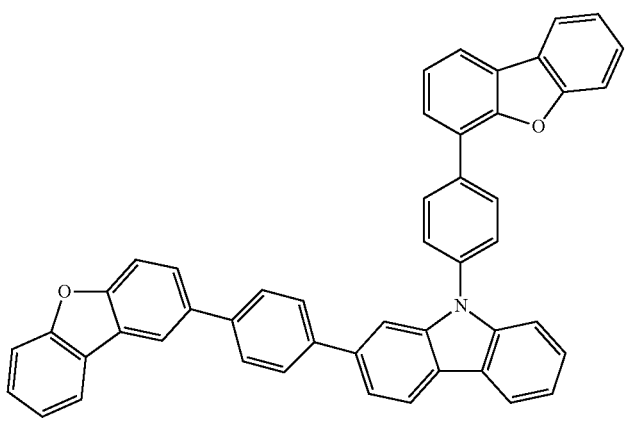 [SMILES: c1ccc2c(c1)oc1ccc(-c3ccc(-c4ccc5c6ccccc6n(-c6ccc(-c7cccc8c7oc7ccccc78)cc6)c5c4)cc3)cc12]
EG7

TABLE 3-continued

Structural formulae of the materials for the OLEDs

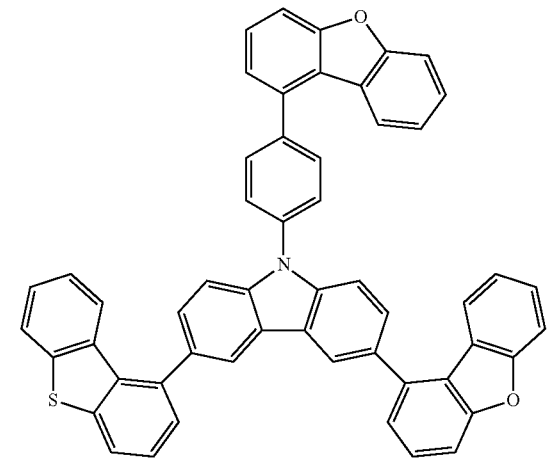 [SMILES: c1ccc2c(c1)oc1cccc(-c3ccc(-n4c5ccc(-c6cccc7oc8ccccc8c67)cc5c5cc(-c6cccc7sc8ccccc8c67)ccc54)cc3)c12]

EG8

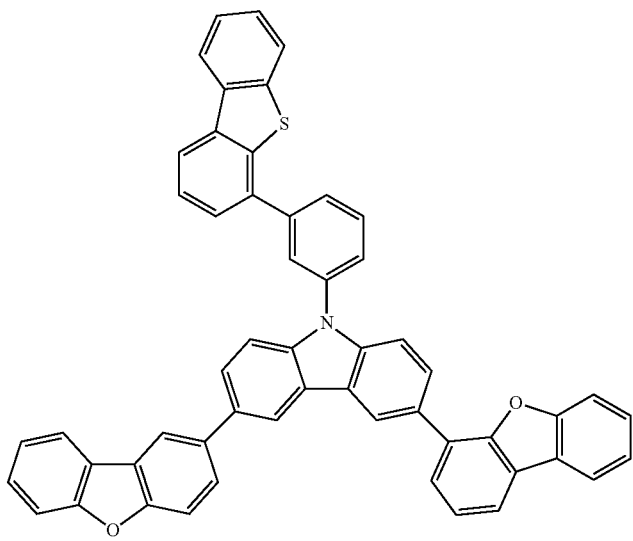 [SMILES: c1cc(-c2cccc3c2sc2ccccc23)cc(-n2c3ccc(-c4ccc5oc6ccccc6c5c4)cc3c3cc(-c4cccc5c4oc4ccccc45)ccc32)c1]

EG9 where the compounds of the invention can be prepared entirely analogously to the abovementioned compounds.

The invention claimed is:

1. A compound comprising structures of the formula (I)

Formula (I)

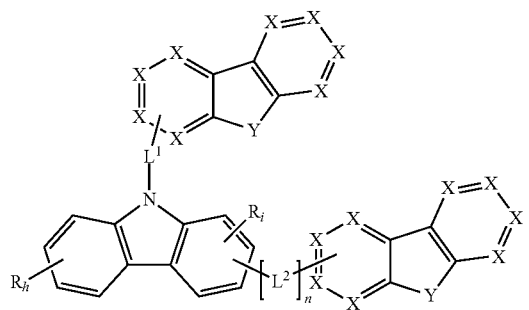

where the symbols used are as follows:

X is N or $CR^1$, with the proviso that not more than one of the X groups in one cycle is N, or C is the attachment site of the $L^1$, $L^2$ radicals or the carbazole group;

Y is the same or different at each instance and is O or S;

$L^1$, $L^2$ is an aromatic ring system which has 6 to 40 carbon atoms and does not have any fused aromatic rings, where the aromatic ring system may be substituted by one or more $R^4$ radicals;

R is H except one of the R radicals in the compound of the formula (I) is a carbazole group not bonded via the nitrogen of the carbazole group;

$R^4$ is the same or different at each instance and is H, D, F, Cl, Br, I, CHO, C(=O)$Ar^2$, P(=O)($Ar^2$)$_2$, S(=O)$Ar^2$, S(=O)$_2Ar^2$, CN, $NO_2$, Si($R^5$)$_3$, B(O$R^5$)$_2$, OS$O_2R^5$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more $R^5$ radicals, where one or more nonadjacent CH$_2$ groups may be replaced by C≡C, Si(R$^5$)$_2$, Ge(R$^5$)$_2$, Sn(R$^5$)$_2$, C=O, C=S, C=Se, P(=O)(R$^5$), SO, SO$_2$, O, S or CONR$^5$ and where one or more hydrogen atoms may be replaced by D, F, Cl, Br, I, CN or NO$_2$, or an aromatic ring system which has 5 to 40 carbon atoms, which does not have any fused aromatic rings and which may be substituted in each case by one or more R$^5$ radicals, or an aryloxy group which has 5 to 40 aromatic ring atoms and may be substituted by one or more R$^5$ radicals, or a combination of these systems; at the same time, two or more adjacent R$^4$ substituents may also form a mono- or polycyclic aliphatic ring system with one another, but one which does not have any fused aromatic rings;

R$^1$ is H, h at each instance is 0, 1, 2, 3 or 4;

i at each instance is independently 0, 1, 2 or 3;

h+i is at least 1; and n is 0 or 1.

2. The compound according to claim 1, wherein n=0.

3. The compound according to claim 1, wherein at least one of the L$^1$ or L$^2$ groups in formula (I) comprises at least one phenylene, biphenylene, fluorenyl and/or spirobifluorenyl group, preferably a phenylene group.

4. The compound according to claim 1, wherein the L$^1$ or L$^2$ groups in formula (I) have a total of not more than 36 carbon atoms.

5. The compound according to claim 1, wherein the L$^1$ or L$^2$ groups in formula (I) have no nitrogen atoms.

6. The compound according to claim 1, wherein at least one Y in the structure of formula (I) is O.

7. The compound according to claim 1, wherein at least one Y in the structure of formula (I) is S.

8. The compound according to claim 1, wherein, in the structure of formula (I), not more than one X is N.

9. The compound according to claim 1, wherein, in the structure of formula (I), at least one group selected from L$^1$, L$^2$ is a group selected from the formulae (L-1) to (L-14)

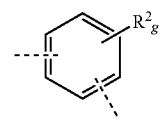

Formula (L-1)

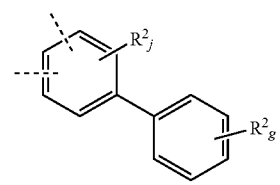

Formula (L-2)

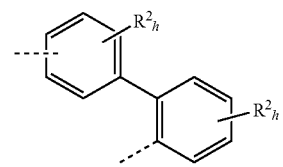

Formula (L-3)

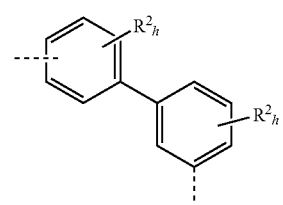

Formula (L-4)

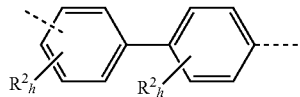

Formula (L-5)

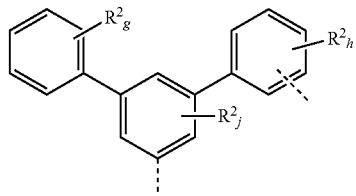

Formula (L-6)

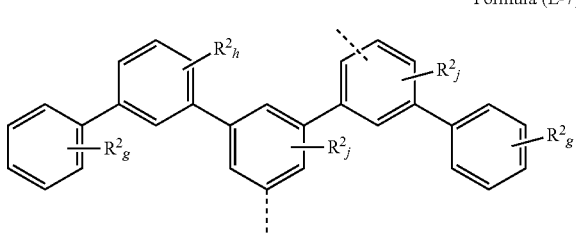

Formula (L-7)

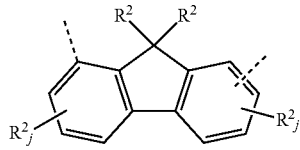

Formula (L-8)

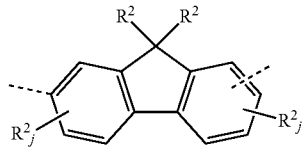

Formula (L-9)

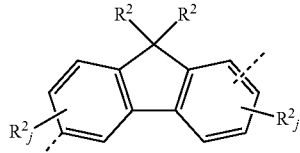

Formula (L-10)

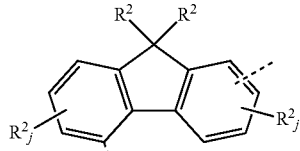

Formula (L-11)

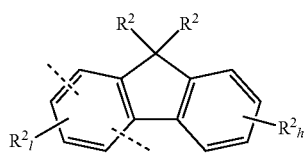

Formula (L-12)

-continued

Formula (L-13)

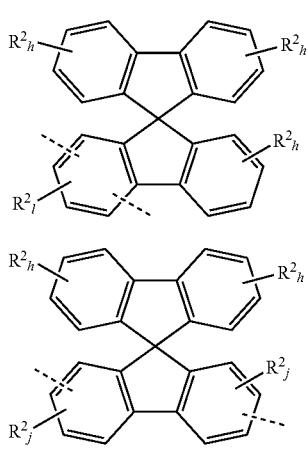

Formula (L-14)

where the dotted bonds each mark the attachment positions, the index l is 0, 1 or 2, the index g is 0, 1, 2, 3, 4 or 5, the index h is 0, 1, 2, 3 or 4, the index j is 0, 1, 2 or 3, and $R^2$ is the same or different at each instance and is H, D, F, Cl, Br, I, CHO, C(=O)Ar$^1$, P(=O)(Ar$^1$)$_2$, S(=O)Ar$^1$, S(=O)$_2$Ar$^1$, CN, NO$_2$, Si(R$^3$)$_3$, B(OR$^3$)$_2$, OSO$_2$R$^3$, a straight-chain alkyl, alkoxy or thioalkoxy group having 1 to 40 carbon atoms or a branched or cyclic alkyl, alkoxy or thioalkoxy group having 3 to 40 carbon atoms, each of which may be substituted by one or more R$^3$ radicals, where one or more nonadjacent CH$_2$ groups may be replaced by C≡C, Si(R$^3$)$_2$, Ge(R$^3$)$_2$, Sn(R$^3$)$_2$, C=O, C=S, C=Se, P(=O)(R$^3$), SO, SO$_2$, O, S or CONR$^3$ and where one or more hydrogen atoms may be replaced by D, F, Cl, Br, I, CN or NO$_2$, or an aromatic or heteroaromatic ring system which has 5 to 40 aromatic ring atoms, each of which may be substituted by one or more R$^3$ radicals, or an aryloxy or heteroaryloxy group which has 5 to 40 aromatic ring atoms and may be substituted by one or more R$^3$ radicals, or a combination of these systems; at the same time, two or more adjacent R$^2$ substituents may also form a mono- or polycyclic aliphatic or aromatic ring system with one another.

10. The compound according to claim 9, wherein the sum total of the indices l, g, h and j in the structures of the formula (L-1) to (L-14) is not more than 3 in each case.

11. The compound according to claim 1, wherein the compound comprises structures of the formulae (II), (III), (IV), (V)

Formula (II)

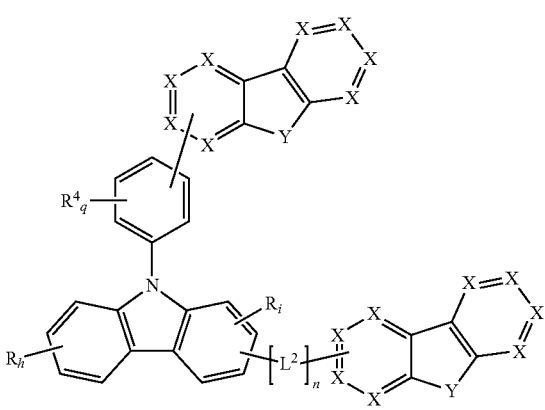

Formula (III)

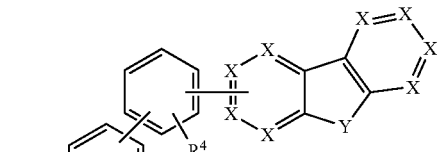

Formula (IV)

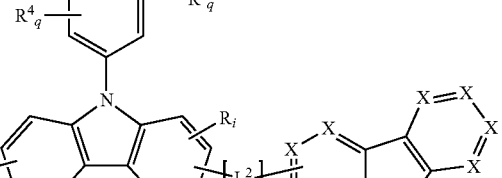

Formula (IV)

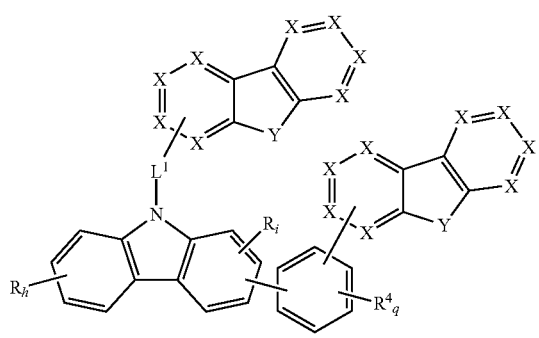

Formula (V)

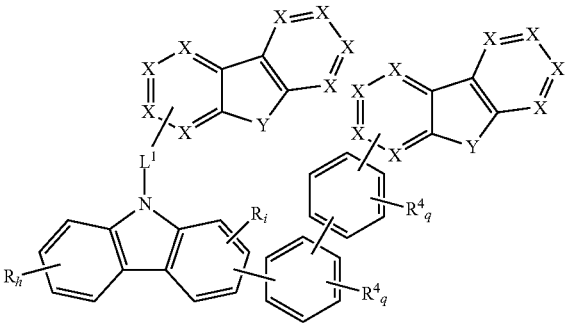

where the symbols X, Y, R, R$^4$, L$^1$, L$^2$ shown and the indices h, i and n are each as defined in claim 1, and the index q is 0, 1, 2, 3 or 4.

12. The compound according to claim 11, wherein the ring closure of two or more adjacent substituents R$^4$ to form a mono- or polycyclic, aliphatic or aromatic ring system is ruled out.

13. The compound according to claim 11, wherein the R, R$^1$, R$^2$, R$^3$ and R$^4$ radicals and the L$^1$, L$^2$ groups have a total of not more than 4 nitrogen atom(s).

14. A composition comprising at least one compound according to claim 1 and at least one further compound selected from the group consisting of fluorescent emitters, phosphorescent emitters, host materials, matrix materials, electron transport materials, electron injection materials, hole conductor materials, hole injection materials, electron blocker materials and hole blocker materials.

15. A formulation comprising at least one compound according to claim 1 and at least one solvent.

16. A process for preparing a compound as claimed in claim 1, wherein, in a coupling reaction, a group comprising at least one carbazole radical is joined to a group comprising at least one benzofuran and/or one benzothiophene radical.

17. A method comprising utilizing the compound according to claim 1 in an electronic device as hole blocker material, electron injection material and/or electron transport material.

18. An electronic device comprising at least one compound according to claim 1.

19. The compound according to claim 1, wherein X is $CR^1$.

20. The compound according to claim 1, wherein, in the structure of formula (I), no X is N.

21. The electronic device according to claim 18, wherein the electronic device is selected from the group consisting of organic electroluminescent devices, organic integrated circuits, organic field-effect transistors, organic thin-film transistors, organic light-emitting transistors, organic solar cells, organic optical detectors, organic photoreceptors, organic field quench devices, light-emitting electrochemical cells and organic laser diodes.

* * * * *